United States Patent
Groebke Zbinden et al.

(10) Patent No.: US 7,820,699 B2
(45) Date of Patent: Oct. 26, 2010

(54) CYCLIC AMINES

(75) Inventors: Katrin Groebke Zbinden, Liestal (CH); Wolfgang Haap, Loerrach (DE); Hans Hilpert, Muenchenstein (CH); Narendra Panday, Basel (CH); Fabienne Ricklin, Hombourg (FR); Beat Wirz, Reinach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 1226 days.

(21) Appl. No.: 11/403,973

(22) Filed: Apr. 13, 2006

(65) Prior Publication Data

US 2006/0247238 A1    Nov. 2, 2006

(30) Foreign Application Priority Data

Apr. 27, 2005   (EP) .................................. 05103452

(51) Int. Cl.
- *A61K 31/4436* (2006.01)
- *A61K 31/4439* (2006.01)
- *C07D 409/14* (2006.01)
- *C07D 401/14* (2006.01)

(52) U.S. Cl. .................. 514/343; 546/278.4; 546/279.1

(58) Field of Classification Search .............. 546/278.4, 546/279.1; 514/343
See application file for complete search history.

(56) References Cited

FOREIGN PATENT DOCUMENTS

| WO | WO 2004/087646 | 10/2004 |
|---|---|---|
| WO | WO 2005/032472 | 4/2005 |
| WO | WO 2006/012226 A2 | 2/2006 |
| WO | WO 2006/032342 A2 | 3/2006 |
| WO | WO 2006/066896 A2 | 6/2006 |

OTHER PUBLICATIONS

Balant et al., "Metabolic Considerations, etc.," Burger's Medicinal Chemistry, 5th ed. , 1, Wolff ed. NY: John Wiley & Sons, 1995, pp. 949-982.*
Schaus et al., J. Org. Chem., 62, pp. 4197-4199 (1997).
Bouzard et al., J. Med. Chem., 33, pp. 1344-1352 (1990).
Sarmiento et al., Tetrahedron Asymmetry, 14, pp. 1547-1551 (2003).
Lee et al., Bioorg. Med. Chem. Lett., 13, pp. 4399-4403 (2003).
Kim et al., J. Med. Chem., 40, pp. 3584-3593 (1997).
Hansen et al., Acta Chemica Scandinavica, 52, pp. 1214-1222 (1997).

* cited by examiner

*Primary Examiner*—Patricia L Morris
(74) *Attorney, Agent, or Firm*—George W. Johnston; Dennis P. Tramaloni; Brian C. Remy

(57) ABSTRACT

The invention is concerned with cyclic amines of formula (I)

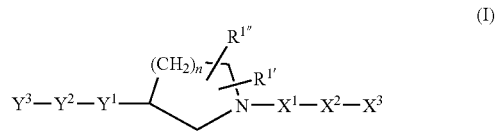

wherein $X^1$ to $X^3$, $Y^1$ to $Y^3$, $R^{1'}$, $R^{1''}$ and n are as defined in the description and in the claims, as well as physiologically acceptable salts thereof. These compounds inhibit coagulation factor Xa and can be used as medicaments and for treating diseases associated with coagulation factor Xa.

15 Claims, No Drawings

CYCLIC AMINES

PRIORITY TO RELATED APPLICATIONS

This application claims the benefit of European Application No. 05103452.8, filed Apr. 27, 2005, which is hereby incorporated by reference in its entirety.

The invention is concerned with novel cyclic amines of formula (I), Compounds of formula (I)

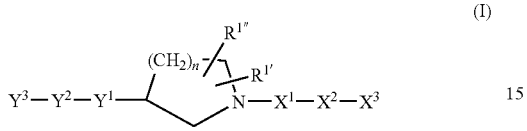

where $X^1$ is —CHR$^2$—C(O)—NH—, —C(O)—CH$_2$—NH—, —C(O)—NH— or —C(O)—C(O)—NH—;

$X^2$ is phenylene, heteroarylene or heterocyclylene, where the phenylene, heteroarylene and heterocyclylene are optionally substituted by one or more substituents independently selected from the group consisting of $C_{1-6}$ alkyl, $C_{3-7}$ cycloalkyl, $C_{3-7}$ cycloalkyl-$C_{1-6}$ alkylene, $C_{1-6}$ alkoxy, halogen, cyano, nitro, amino, —CO—NH—$C_{1-6}$ alkyl, —CO—N($C_{1-6}$ alkyl)$_2$, —CO—NR'R" wherein R' and R", together with the nitrogen atom to which they are attached, form heterocycyl,

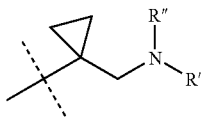

where R' and R" are independently $C_{1-6}$ alkyl or R' and R", together with the nitrogen atom to which they are attached, form heterocyclyl, and

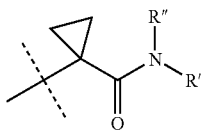

wherein R' and R" are independently $C_{1-6}$ alkyl or R' and R", together with the nitrogen atom to which they are attached, form heterocyclyl;

$X^3$ is hydrogen, phenyl, heteroaryl or heterocyclyl, where the phenyl, heteroaryl and heterocyclyl are optionally substituted by one or more substituents independently selected from the group consisting of $C_{1-6}$ alkyl, $C_{1-6}$ alkoxy, halogen, cyano, nitro, amino, mono-$C_{1-6}$ alkyl-substituted amino, di-$C_{1-6}$ alkyl-substituted amino, mono-$C_{1-16}$ alkyl-substituted amino-$C_{1-6}$ alkylene, di-$C_{1-6}$ alkyl substituted amino-$C_{1-6}$ alkylene, —SO$_2$—$C_{1-6}$ alkyl, —SO$_2$—NH$_2$, —SO$_2$—NH—$C_{1-6}$ alkyl and —SO$_2$—N($C_{1-6}$ alkyl)$_2$, where one or two carbon atoms of sthe phenyl, heteroaryl and heterocyclyl are optionally replaced with a carbonyl group;

$R^2$ is hydrogen or $C_{1-6}$ alkyl;

$Y^1$ is —C(O)—NH—, —C(O)—NH—CH$_2$— or —NH—C(O)—;

$Y^2$ is phenylene, heteroarylene or heterocyclylene, where the phenylene, heteroarylene and heterocyclylene are optionally substituted by one or more substituents independently selected from the group consisting of $C_{1-6}$ alkyl, $C_{3-7}$ cycloalkyl, $C_{3-7}$ cycloalkyl-$C_{1-6}$ alkylene, $C_{1-6}$ alkoxy, halogen, cyano, nitro, amino, —CO—NH—$C_{1-6}$ alkyl, —CO—N($C_{1-6}$ alkyl)$_2$, —CO—NR'R" wherein R' and R", together with the nitrogen atom to which they are attached, form heterocycyl,

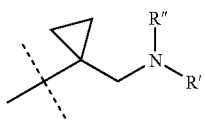

where R' and R" are independently $C_{1-6}$ alkyl or R' and R", together with the nitrogen atom to which they are attached, form heterocyclyl and

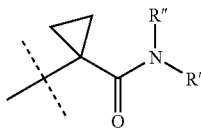

where R' and R" are independently $C_{1-6}$ alkyl or R' and R", together with the nitrogen atom to which they are attached, form heterocyclyl;

$Y^3$ is hydrogen, phenyl, heteroaryl or heterocyclyl, where the phenyl, heteroaryl and heterocyclyl are optionally substituted by one or more substituents independently selected from the group consisting of $C_{1-6}$ alkyl, $C_{1-6}$ alkoxy, halogen, cyano, nitro, amino, mono-$C_{1-6}$ alkyl substituted amino, di-$C_{1-6}$ alkyl substituted amino, mono-$C_{1-6}$ alkyl substituted amino-$C_{1-6}$ alkylene, di-$C_{1-6}$ alkyl substituted amino-$C_{1-6}$ alkylene, —SO$_2$—$C_{1-6}$ alkyl, —SO$_2$—NH$_2$, —SO$_2$—NH—$C_{1-6}$ alkyl and —SO$_2$—N($C_{1-6}$ alkyl)$_2$, where one or two carbon atoms of the phenyl, heteroaryl and heterocyclyl are optionally replaced with a carbonyl group;

$R^{1'}$ is halogen, carboxyl, $C_{1-6}$ alkoxycarbonyl, hydroxy $C_{1-6}$ alkyl-NH—C(O)—, N($C_{1-6}$ alkyl)(hydroxy $C_{1-6}$ alkyl)-C(O)—, $C_{1-6}$ alkyl-NH—C(O)—, halo $C_{1-6}$ alkyl-NH—C(O)—, $C_{3-7}$ cycloalkyl-$C_{1-6}$ alkylene-NH—C(O)—, hydroxy $C_{1-6}$ alkyl-, hydroxy, $C_{1-6}$ alkoxy, $C_{1-6}$ alkoxy-$C_{1-6}$ alkylene, haloC$_{1-6}$ alkoxy-$C_{1-6}$ alkylene, halo $C_{1-6}$ alkyl, halo $C_{1-6}$ alkoxy, heterocyclyl-$C_{1-6}$ alkylene, $C_{1-6}$ alkyl-sulfonylamino-$C_{1-6}$ alkylene, ($C_{1-6}$ alkyl-sulfonyl)($C_{1-6}$ alkyl)amino-$C_{1-6}$ alkylene, $C_{1-6}$ alkyl-carbonylamino-$C_{1-6}$ alkylene, hydroxy-$C_{1-6}$ alkoxy-, amino, di-$C_{1-6}$ alkyl substituted amino, mono-$C_{1-6}$ alkyl substituted amino, di-$C_{1-6}$ alkyl substituted amino-$C_{1-6}$ alkylene, mono-$C_{1-6}$ alkyl substituted amino-$C_{1-6}$ alkylene, di-halo$C_{1-6}$ alkyl substituted amino, mono-halo$C_{1-6}$ alkyl substituted amino, $C_{3-7}$ cycloalkylamino-$C_{1-6}$ alkylene, heterocyclyl-amino-$C_{1-6}$ alkylene, ($C_{3-7}$ cycloalkyl)($C_{1-6}$ alkyl)amino-$C_{1-6}$ alkylene, (heterocyclyl)($C_{1-6}$ alkyl)amino-$C_{1-6}$ alkylene, $C_{1-6}$ alkylcarbonyl-$C_{1-6}$ alkylene, $C_{1-6}$ alkyl-sulfonylamino-, $C_{1-6}$ alkyl-carbonylamino-, ($C_{1-6}$ alkylcarbonyl)($C_{1-6}$ alkyl)amino-, ($C_{1-6}$ alkoxy-carbonyl)($C_{1-6}$ alkyl)amino-, ($C_{1-6}$ alkylsulfonyl)($C_{1-6}$ alkyl)amino-, heterocyclyl, halogenated heterocyclyl, $C_{1-6}$ alkylsulfonyloxy-$C_{1-6}$ alkylene, ($C_{1-6}$ alkylcarbonyl)($C_{1-6}$ alkyl)amino-$C_{1-6}$ alkylene or NR'R"—$C_{1-6}$ alkylene, where R' and R", together with the nitrogen atom to which they are attached, form a lactam containing one to six carbon atoms, where one or two carbon atoms of the heterocyclyl in heterocyclyl-$C_{1-6}$ alkylene, heterocyclyl-amino-$C_{1-6}$ alkylene, heterocyclyl)($C_{1-6}$ alkyl)amino-$C_{1-6}$ alkylene, heterocyclyl, and halogenated heterocycly are optionally replaced with a carbonyl group;

or $R^{1'}$ is halogenated heterocyclyl-$C_{1-6}$ alkylene, di-halo$C_{1-6}$ alkyl substituted amino-$C_{1-6}$ alkylene, mono-halo$C_{1-6}$ alkyl substituted amino-$C_{1-6}$ alkylene, $C_{1-6}$ alkyl, phenyl optionally substituted by one, two or three of the same or different halogen atoms, $C_{3-7}$ cycloalkyl optionally substituted by one, two or three of the same or different halogen atoms or Z-carbonyl-$C_{1-6}$ alkoxy-, in which Z is hydroxy, $C_{1-6}$ alkoxy or NR'R", where R' and R" are independently hydrogen, $C_{1-6}$ alkyl optionally substituted by one, two or three of the same or different halogen atoms, $C_{3-7}$ cycloalkyl optionally substituted by one, two or three of the same or different halogen atoms or $C_{3-7}$ cycloalkyl-$C_{1-6}$ alkylene optionally substituted by one, two or three of the same or different halogen atoms, where one or two carbon atoms of the heterocyclyl in halogenated heterocyclyl-$C_{1-6}$ alkylene, one or two carbon atoms of the phenyl in phenyl optionally substituted by one, two or three of the same or different halogen atoms, and one or two carbon atoms of the $C_{3-7}$ cycloalkyl in the $C_{3-7}$ cycloalkyl optionally substituted by one, two or three of the same or different halogen atoms and $C_{3-7}$ cycloalkyl-$C_{1-6}$ alkylene optionally substituted by one, two or three of the same or different halogen atoms are optionally replaced with a carbonyl group;

$R^{1'''}$ is hydrogen; or $R^{1'}$ and $R^{1'''}$ form, together with the carbon atoms to which they are attached, —C(=O)—, —C(=CH$_2$)—, $C_{3-7}$ cycloalkyl or heterocyclyl, where one or two carbon atoms of the heterocyclyl may be optionally replaced with a carbonyl group;

n is 1 or 2;

provided that when $X^1$ is —C(O)—CH$_2$—NH—, —C(O)—NH— or

—C(O)—, then $X^3$ is not hydrogen, and when $Y^1$ is —NH—C(O)—, then $Y^3$ is not hydrogen; and provided that when $X^1$ is —C(O)—NH—, then $Y^1$ is —C(O)—NH—CH$_2$—, and when $Y^1$ is —C(O)—NH— or —NH—C(O)—, then $X^1$ is —CHR$^2$—C(O)—NH— or —C(O)—CH$_2$—NH—; and prodrugs and pharmaceutically acceptable salts thereof.

$X^2$ is preferably phenylene, heteroarylene or heterocyclylene, where the phenylene, heteroarylene and heterocyclylen are optionally substituted by one or more substituents independently selected from the group consisting of $C_{1-6}$alkyl, $C_{1-6}$ alkoxy, halogen, cyano, nitro, amino, —CO—NH—$C_{1-6}$ alkyl, —CO—N($C_{1-6}$ alkyl)$_2$, —CO—NR'R" wherein R' and R", together with the nitrogen atom to which they are attached, form heterocyyl,

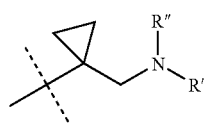

where R' and R" are independently $C_{1-6}$ alkyl or R' and R", together with the nitrogen atom to which they are attached, form heterocyclyl and

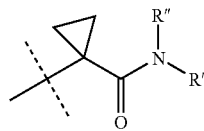

wherein R' and R" are independently $C_{1-6}$alkyl or R' and R", together with the nitrogen atom to which they are attached, form heterocyclyl;

$Y^2$ is preferably phenylene, heteroarylene or heterocyclylene, where the phenylene, heteroarylene and heterocyclylene may be optionally substituted by one or more substituents independently selected from the group consisting of $C_{1-6}$ alkyl, $C_{1-6}$ alkoxy, halogen, cyano, nitro, amino, —CO—NH—$C_{1-6}$ alkyl, —CO—N($C_{1-6}$ alkyl)$_2$, —CO—NR'R" wherein R' and R", together with the nitrogen atom to which they are attached, form heterocyyl,

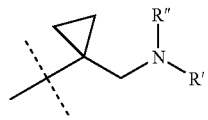

wherein R' and R" are independently $C_{1-6}$ alkyl or R' and R", together with the nitrogen atom to which they are attached, form heterocyclyl and

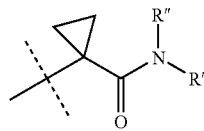

wherein R' and R" are independently $C_{1-6}$ alkyl or R' and R", together with the nitrogen atom to which they are attached, form heterocyclyl;

$R^{1'}$ is preferably halogen, carboxyl, $C_{1-6}$ alkoxycarbonyl, hydroxy $C_{1-6}$ alkyl-NH—C(O)—, N($C_{1-6}$ alkyl)(hydroxy $C_{1-6}$ alkyl)-C(O)—, $C_{1-6}$ alkyl-NH—C(O)—, halo $C_{1-6}$ alkyl-NH—C(O)—, $C_{3-7}$ cycloalkyl-$C_{1-6}$ alkylene-NH—C(O)—, hydroxy $C_{1-6}$ alkyl, hydroxy, $C_{1-6}$ alkoxy, $C_{1-6}$ alkoxy-$C_{1-6}$ alkylene, halo $C_{1-6}$ alkoxy-$C_{1-6}$ alkylene, halo $C_{1-6}$ alkyl, halo $C_{1-6}$ alkoxy, heterocyclyl-$C_{1-6}$ alkylene, $C_{1-6}$ alkyl-sulfonylamino-$C_{1-6}$ alkylene, ($C_{1-6}$ alkyl-sulfonyl)($C_{1-6}$ alkyl)amino-$C_{1-6}$ alkylene, $C_{1-6}$ alkyl-carbonylamino-$C_{1-6}$ alkylene, hydroxy $C_{1-6}$ alkoxy-, amino, di-$C_{1-6}$ alkyl substituted amino, mono-$C_{1-6}$ alkyl substituted amino, di-$C_{1-6}$ alkyl substituted amino-$C_{1-6}$ alkylene, mono-$C_{1-6}$alkyl substituted amino-$C_{1-6}$ alkylene, di-halo$C_{1-6}$ alkyl substituted amino, mono-halo$C_{1-6}$ alkyl substituted amino, $C_{3-7}$ cycloalkylamino-$C_{1-6}$ alkylene, heterocyclyl-amino-$C_{1-6}$ alkylene, ($C_{3-7}$ cycloalkyl)($C_{1-6}$ alkyl)amino-$C_{1-6}$ alkylene, (heterocyclyl)($C_{1-6}$ alkyl)amino-$C_{1-6}$ alkylene, $C_{1-6}$ alkylcarbonyl-$C_{1-6}$ alkylene, $C_{1-6}$ alkyl-sulfonylamino-, $C_{1-6}$ alkyl-carbonylamino-, ($C_{1-6}$ alkylcarbonyl)($C_{1-6}$ alkyl)amino-, ($C_{1-6}$ alkoxy-carbonyl)($C_{1-6}$ alkyl)amino-, ($C_{1-6}$ alkylsulfonyl)($C_{1-6}$ alkyl)amino-, heterocyclyl, halogenated heterocyclyl, $C_{1-6}$ alkylsulfonyloxy-$C_{1-6}$ alkylene, ($C_{1-6}$ alkylcarbonyl)($C_{1-6}$ alkyl)amino-$C_{1-6}$ alkylene or NR'R"—$C_{1-6}$ alkylene where R' and R", together with the nitrogen atom to which they are attached, form a lactam containing one to six carbon atoms, where one or two carbon atoms of the heterocyclyl in said heterocyclyl-$C_{1-6}$ alkylene, said heterocyclyl-amino-$C_{1-6}$ alkylene, said (heterocyclyl)($C_{1-6}$ alkyl)amino-$C_{1-6}$ alkylene, said heterocyclyl and said halogenated heterocyclyl may be optionally replaced with a carbonyl group.

Further, the invention is concerned with processes and intermediates for the manufacture of the above compounds, pharmaceutical preparations which contain such compounds, the use of these compounds for the production of pharmaceutical preparations as well as a process for the manufacture of the intermediate.

The compounds of formula (I) are active compounds and inhibit the activity of coagulation factor Xa.

These compounds consequently influence blood coagulation. They therefore inhibit the formation of thrombin and can be used for the treatment and/or prevention of thrombotic disorders, such as arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. They have potentially benefit in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. Factor Xa inhibitors of this invention may form part of a combination therapy with an anticoagulant with a different mode of action or with a platelet aggregation inhibitor or with a thrombolytic agent.

Furthermore, these compounds have an effect on tumor cells and prevent metastases. They can therefore also be used as antitumor agents.

Other inhibitors of factor Xa have been suggested for the inhibition of the formation of thrombin and for the treatment of related diseases. However, there is still a need for novel factor Xa inhibitors which exhibit improved pharmacological properties, e.g. an improved selectivity towards thrombin.

The present invention provides novel compounds of formula (I) which are factor Xa inhibitors.

The compounds of the present invention unexpectedly inhibit coagulation factor Xa and also exhibit improved pharmacological properties compared to other compounds already known in the art.

Unless otherwise indicated, the following definitions are set forth to illustrate and define the meaning and scope of the various terms used to describe the invention herein.

The term "halogen" or "halo" means fluorine, chlorine, bromine and iodine, with fluorine, chlorine and bromine being of particular interest, more particularly fluorine and chlorine.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. $C_{1-4}$ alkyl means a branched or straight-chain monovalent alkyl radical, having one to four carbon atoms. and is also exemplified by the aformentioned specific radicals.

The term "alkylene", alone or in combination with other groups, means a branched or straight-chain, saturated, divalent hydrocarbon radical.

The term "halo $C_{1-6}$ alkyl" means $C_{1-6}$ alkyl substituted by one or more same or different halogen atoms independently selected from the group consisting of chlorine, fluorine and bromine, such as $CF_3$.

The term "hydroxy $C_{1-6}$ alkyl" means $C_{1-6}$ alkyl substituted by one or more hydroxy group.

The term "$C_{3-7}$ cycloalkyl", alone or in combination with other groups, means a saturated monovalent cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "phenylene", alone or in combination with other groups, means a divalent phenyl group.

The term "heterocyclyl", alone or combination with other groups, means non-aromatic mono- or bi-cyclic radicals of three to eight ring atoms in which one or two ring atoms are heteroatoms selected from N, O, or $S(O)_n$ (where n is an integer from 0 to 2), the remaining ring atoms being C.

The term "heterocyclylene", alone or combination with other groups, means a divalent heterocyclyl group as defined above.

The term "heteroaryl", alone or combination with other groups, means a monocyclic or bicyclic radical of 5 to 12 ring atoms having at least one aromatic ring containing one, two, or three ring heteroatoms selected from N, O, and S, the remaining ring atoms being C, with the understanding that the attachment point of the heteroaryl radical will be on an aromatic ring.

The term "heteroarylene", alone or combination with other groups, means a divalent heteroaryl group as defined above.

Particular radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and trimethylammonium salts. The term "pharmaceutically acceptable salts" also refers to such salts.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Enantiomerically enriched" means over 0% enantiomeric excess, preferably at least 80-95% enantiomeric excess.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) may be more particulary described.

I)-i) One group of compounds of the invention are compounds of formula (I) where $X^1$ is —$CH_2$—C(O)—NH— or —C(O)—NH—.

I-ii) When $X^1$ is as described under I)-i), $X^2$ may be phenylene or heteroarylene, where the phenylene and heteroarylene may be optionally substituted by one or more substituents independently selected from the group consisting of $C_{1-6}$ alkyl and halogen.

$X^2$ may be 1,4-phenylene optionally substituted by one or more substituents independently selected from the group consisting of $C_{1-6}$ alkyl and halogen.

$X^2$ may be 1,4-phenylene optionally substituted by one or more of the same or different halogen atoms, especially 2-fluoro-1,4-phenylene.

I-iii) When $X^1$ is as described under I)-i), $X^3$ may be heteroaryl optionally substituted by one or more substituents independently selected from the group consisting of $C_{1-6}$ alkyl, $C_{1-6}$ alkoxy, halogen, cyano, nitro and amino, where one or two carbon atoms of the heteroaryl are optionally replaced with a carbonyl group.

$X^3$ may be heteroaryl containing one nitrogen atom, especially pyridyl optionally substituted by one or more substituents independently selected from the group consisting of $C_{1-6}$ alkyl, $C_{1-6}$ alkoxy, halogen, cyano, nitro and amino, where one or two carbon atoms of the heteroaryl may be optionally replaced with a carbonyl group, e.g., $X^3$ may be 2-Oxo-2H-pyridin-1-yl.

I)-iv) When $X^1$ is as described under I)-i), $Y^1$ may be —C(O)—NH— or —C(O)—NH—$CH_2$—.

I)-v) When $X^1$ is as described under I)-i), $Y^2$ may be heteroarylene optionally substituted by one or more substituents independently selected from the group consisting of halogen, $C_{1-6}$ alkyl and $C_{1-6}$ alkoxy, for example $Y^2$ may be heteroarylene optionally substituted by one or more same or different halogen atoms, and $Y^3$ may be hydrogen.

Examples of a heteroaryl formed by $Y^3$—$Y^2$— are, for example, thiophenyl, indolyl, benzofuranyl, benzothiophenyl, pyridyl, thiazolyl, pyrrolyl and furanyl which are optionally substituted by one or more of the same or different halogen atoms. For example, a heteroaryl formed by $Y^3$—$Y^2$ may be a heteroaryl having five ring member atoms, and containing one sulfur atom, optionally substituted by one or more of the same or different halogen atoms, e.g., chlorine. $Y^3$—$Y^2$ may be, for example, 5-chloro-thiophen-2-yl.

I)-vi) When $X^1$ is as described as under I)-i), n may be 1.

I)-vii) When $X^1$ is as described under I)-i), $R^{1'}$ may be hydroxy, $C_{1-6}$ alkoxy, mono-$C_{1-6}$ alkyl substituted amino, ($C_{1-6}$ alkylsulfonyl)($C_{1-6}$ alkyl)amino-, $C_{1-6}$ alkylsulfonyl-amino-, $C_{1-6}$ alkyl-carbonylamino-, ($C_{1-6}$ alkylcarbonyl)($C_{1-6}$ alkyl)amino-, or $CF_3$. $R^{1'}$ thus may be hydroxy or $C_{1-6}$ alkoxy. $R^{1'}$ may also be $C_{1-6}$ alkyl when $X^1$ is as described under I)-i).

II) Other compounds of the invention are those of formula (I) where $X^2$ is phenylene or heteroarylene, where the phenylene and heteroarylene may be optionally substituted by one or more substituents independently selected from the group consisting of $C_{1-6}$ alkyl and halogen.

$X^2$ may more particularly be 1,4-phenylene optionally substituted by one or more substituents independently selected from the group consisting of $C_{1-6}$ alkyl and halogen.

$X^2$ may more particularly be 1,4-phenylene optionally substituted by one or more of the same or different halogen atoms, e.g., $X^2$ may be 2-fluoro-1,4-phenylene.

III) Other particular compounds of the invention are those compounds of formula (I) where $X^3$ is heteroaryl optionally substituted by one or more substituents independently selected from the group consisting of $C_{1-6}$ alkyl, $C_{1-6}$ alkoxy, halogen, cyano, nitro and amino, where one or two carbon atoms of the heteroaryl are optionally replaced with a carbonyl group.

$X^3$ in particular may be heteroaryl containing one nitrogen atom, e.g. pyridyl optionally substituted by one or more substituents independently selected from the group consisting of $C_{1-6}$ alkyl, $C_{1-6}$ alkoxy, halogen, cyano, nitro and amino, where one or two carbon atoms of the heteroaryl are optionally replaced with a carbonyl group, such as a 2-Oxo-2H-pyridin-1-yl group.

IV) Other particular compounds of the invention are those compounds of formula (I) where $Y^1$ is —C(O)—NH— or —C(O)—NH—$CH_2$—.

V) Other particular compounds of the invention are those compounds of formula (I) where $Y^2$ is heteroarylene optionally substituted by one or more substituents independently selected from the group consisting of halogen, $C_{1-6}$ alkyl and $C_{1-6}$ alkoxy, in particular where $Y^2$ is heteroarylene optionally substituted by one or more of the same or different halogen atoms, and $Y^3$ is hydrogen.

Examples of a heteroaryl formed by $Y^3$—$Y^2$— are, for example, thiophenyl, indolyl, benzofuranyl, benzothiophenyl, pyridyl, thiazolyl, pyrrolyl and furanyl which may be optionally substituted by one or more of the same or different halogen atoms. In particular, a heteroaryl formed by $Y^3$—$Y^2$— may be a heteroaryl having five ring member atoms, and containing one sulfur atom, optionally substituted by one or more of the same or different halogen atoms, in particular chlorine. 5-chloro-thiophen-2-yl is a particular heteroaryl formed by $Y^3$—$Y^2$—.

VI) Other particular compounds of the invention are compounds of formula (I) where n is 1.

VII) Other particular compounds of the invention are compounds of formula (I) where $R^{1''}$ is hydroxy, $C_{1-6}$ alkoxy, mono-$C_{1-6}$ alkyl substituted amino, ($C_{1-6}$ alkylsulfonyl)($C_{1-6}$ alkyl)amino-, $C_{1-6}$ alkylsulfonyl-amino-, $C_{1-6}$ alkyl-carbonylamino-, ($C_{1-6}$ alkylcarbonyl)($C_{1-6}$ alkyl)amino-, $CF_3$, or more particularly where $R^{1''}$ is hydroxy or $C_{1-6}$ alkoxy, or $C_{1-6}$ alkyl.

VIII) Other particular compounds of the invention are compounds of formula (I'),

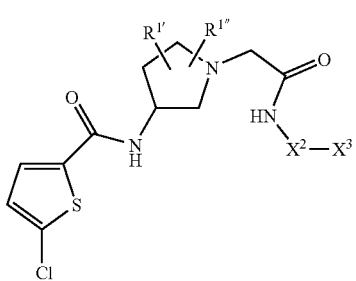

(I')

where $X^2$, $X^3$, $R^{1'}$ and $R^{1''}$ are as defined before.

IX) Another particular group of compound of the invention are compounds of formula (I"),

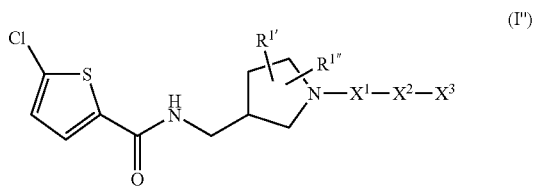

(I")

wherein $X^1$, $X^2$, $X^3$, $R^{1'}$ and $R^{1''}$ are as defined before.

X) Particular compounds of the present invention are:

5-Chloro-thiophene-2-carboxylic acid ((3S,4S)-1-{[2-fluoro-4-(2-oxo-2H-pyridin-1-yl)-phenylcarbamoyl]-methyl}-4-hydroxy-pyrrolidin-3-yl)-amide, 5-Chloro-thiophene-2-carboxylic acid ((3S,4S)-1-{[2-fluoro-4-(2-oxo-2H-pyridin-1-yl)-phenylcarbamoyl]-methyl}-4-methoxy-pyrrolidin-3-yl)-amide, 5-Chloro-thiophene-2-carboxylic acid ((3S,4S)-4-methoxy-1-{[4-(2-oxo-2-pyridin-1-yl)-phenylcarbamoyl]-methyl}-pyrrolidin-3-yl)-amide, 5-Chloro-thiophene-2-carboxylic acid ((3S,4S)-1-{[2-fluoro-4-(3-oxo-morpholin-4-yl)-phenylcarbamoyl]-methyl}-4-methoxy-pyrrolidin-3-yl)-amide, 5-Chloro-thiophene-2-carboxylic acid ((3S,4S)-1-{[2-fluoro-4-(2-oxo-pyrazin-1-yl)-phenylcarbamoyl]-methyl}-4-methoxy-pyrrolidin-3-yl)-amide, 5-Chloro-thiophene-2-carboxylic acid ((3S,4S)-4-ethoxy-1-{[2-fluoro-4-(2-oxo-pyridin-1-yl)-phenylcarbamoyl]-methyl}-pyrrolidin-3-yl)-amide, 5-Chloro-thiophene-2-carboxylic acid [(3S,4S)-1-{[2-fluoro-4-(2-oxo-2H-pyridin-1-yl)-phenylcarbamoyl]-methyl}-4-(2-hydroxy-ethoxy)-pyrrolidin-3-yl]-amide, (3R,4S)-3-{[(5-Chloro-thiophene-2-carbonyl)-amino]-methyl}-4-trifluoromethyl-pyrrolidine-1-carboxylic acid[2-fluoro-4-(2-oxo-2H-pyridin-1-yl)-phenyl]-amide, (3R,4S)-3-{[(5-Chloro-thiophene-2-carbonyl)-amino]-methyl}-4-methoxy-pyrrolidine-1-carboxylic acid[2-fluoro-4-(2-oxo-2H-pyridin-1-yl)-phenyl]-amide, (3R,4R)-3-{[(5-Chloro-thiophene-2-carbonyl)-amino]-methyl}-4-hydroxy-pyrrolidine-1-carboxylic acid[2-fluoro-4-(2-oxo-2H-pyridin-1-yl)-phenyl]-amide, (R)-3-{[(5-Chloro-thiophene-2-carbonyl)-amino]-methyl}-4-methylamino-pyrrolidine-1-carboxylic acid[2-fluoro-4-(2-oxo-2H-pyridin-1-yl)-phenyl]-amid formiate, {(R)-4-{[(5-Chloro-thiophene-2-carbonyl)-amino]-methyl}-1-[2-fluoro-4-(2-oxo-2H-pyridin-1-yl)-phenylcarbamoyl]-pyrrolidin-3-yl}-methyl-carbamic acid methyl ester, or (R)-3-{[(5-Chloro-thiophene-2-carbonyl)-amino]-methyl}-4-(methanesulfonyl-methyl-amino)-pyrrolidine-1-carboxylic acid[2-fluoro-4-(2-oxo-2H-pyridin-1-yl)-phenyl]-amide.

XI) Further particular compounds of the present invention are:

5-Chloro-thiophene-2-carboxylic acid ((3R,4S)-1-{[2-fluoro-4-(2-oxo-pyridin-1-yl)-phenylcarbamoyl]-methyl}-4-methyl-pyrrolidin-3-yl)-amide, or 5-Chloro-thiophene-2-carboxylic acid {(3S,4S)-4-methoxy-1-[(5-methyl-4,5,6,7-tetrahydro-thiazolo[5,4]pyridin-2-ylcarbamoyl)-methyl]-pyrrolidin-3-yl}-amide.

The compounds of the present invention can be prepared, for example, by the general synthetic procedures described below.

General Synthetic Procedures

Abbreviations

BOP: Benzotriazolyl-N-oxy-tris(dimethylamino)-phosphonium hexafluorophosphate
BOP-Cl: Bis-(2-oxo-3-oxazolidinyl)-phosphinic acid chloride
CDI: 1,1'-Carbonyldiimidazole
DCM: Dichloromethane
DIPEA: Diisopropyl ethyl amine
DMA: N,N-Dimethylacetamide
DMF: N,N-Dimethylformamide
DMSO: Dimethylsulfoxide
EDCI: N-(3-Dimethylaminopropyl)-N'-ethyl-carbodiimide hydrochloride
Fmoc: 9-Fluorenylmethyloxy carbonyl
HOBT: 1-Hydroxybenzotriazole
MOZ: 4-Methoxybenzyloxy carbonyl
NMP: N-Methylpyrrolidinone
PyBOP: Benzotriazol-1-yl-oxytripyrrolidinephosphonium hexafluorophosphate
TEA: Triethylamine
Teoc: 2-(Trimethylsilyl)ethyloxy carbonyl
TBAF: Tetrabutylammonium fluoride
TBTU: O-(Benzotriazol-1-yl)-N,N,N',N'-tetramethyluronium terafluoroborate
TFA: Trifluoroacetic acid 1. Synthesis starting from 3-(Boc-amino)pyrrolidine and 3-(Boc-amino)piperidine The following scheme depicts only the pyrrolidine series. Piperidine derivatives were synthesized by analogous procedures.

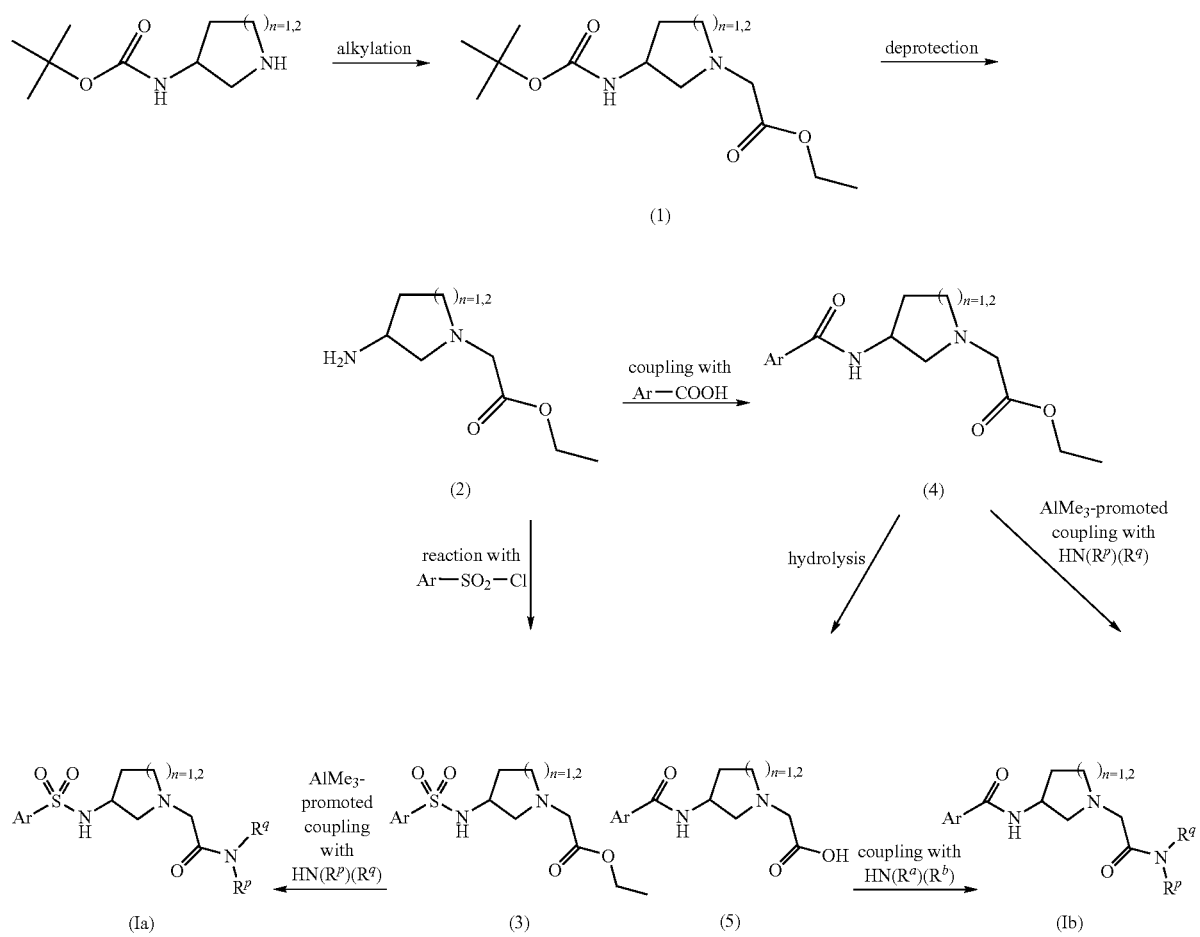

Ar in the scheme is $Y^3$—$Y^2$ as defined before. $R^p$ in the scheme is hydrogen and $R^q$ in the scheme is —$X^2$—$X^3$ as defined before.

Intermediate (1): The starting amine is dissolved in a suitable solvent such as THF, acetonitrile or DMF and treated with ethyl bromoacetate in the presence of a base like TEA or DIPEA and reacted under an argon atmosphere at 0° C. to 50° C. for 1 hr-72 hrs. Particular conditions are THF and TEA.

Intermediate (2): Deprotection of intermediate (1) is effected by treatment with a mineral acid such as HCl, HBr, $H_2SO_4$ or $H_3PO_4$ or a carboxylic acid, in a solvent such as $CH_2Cl_2$, dioxane or HOAc at 0 to 60° C. Particular conditions are 4N HCl in dioxane.

Intermediate (3): Intermediate (2) is reacted with a sulfonyl chloride Ar—$SO_2$—Cl in a solvent such as THF, methylene chloride, DMF or acetonitrile in the presence of an organic base such as TEA or DIPEA and reacted under an argon atmosphere at 0° C. to 50° C. for 1 hr-72 hrs. Particular conditions are THF and TEA.

Final product (Ia): Intermediate (3) is reacted with an aniline $HN(R^p)(R^q)$. The aniline is preactivated with $AlMe_3$ in a solvent such as toluene or dioxane under an argon atmosphere at r.t. for 1 hr-3 hrs and subsequently treated with ester III at elevated temperature (usually 90° C.-110° C.) for 1 hr-18 hrs to give the amide Ia.

Intermediate (4): Intermediate (2) is reacted with a carboxylic acid Ar—COOH in a suitable solvent such as $CH_2Cl_2$, DMF, acetonitrile, THF. Activation is effected by an amide coupling reagent such as BOP, BOP-Cl, TBTU, EDCI/DMAP in the presence of a base like TEA, DIPEA, N-methylmorpholine etc. at 0° C. to 50° C. Reaction times ranged from 1 hr-72 hrs. Particular conditions are DMF, BOP and DIPEA.

Intermediate (5): Hydrolysis of intermediate (4) is effected by dissolving it in a suitable solvent like MeOH, EtOH, THF, 1,4-dioxane, water or mixtures thereof and a base like LiOH, NaOH, KOH, $Na_2CO_3$, $K_2CO_3$ or $Cs_2CO_3$. Particular conditions are NaOH in EtOH/$H_2O$.

Final product (Ib): Intermediate (5) is coupled with an amine $HN(R^p)(R^q)$ in a suitable solvent such as $CH_2Cl_2$, DMF, acetonitrile, THF. Activation is effected by an amide coupling reagent such as BOP, BOP-Cl, TBTU, EDCI/DMAP in the presence of a base like TEA, DIPEA, N-methylmorpholine etc. at 0° C. to 50° C. Reaction times ranged from 1 hr-72 hrs. Particular conditions are DMF, BOP and DIPEA.

Alternatively, intermediate (4) is reacted with an aniline $HN(R^p)(R^q)$ as described for the preparation of final product (Ia).

2. Synthesis starting from (R)-1-Boc-aminopyrrolidine

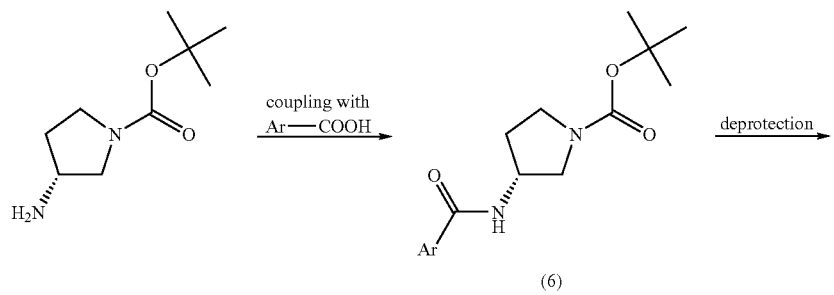

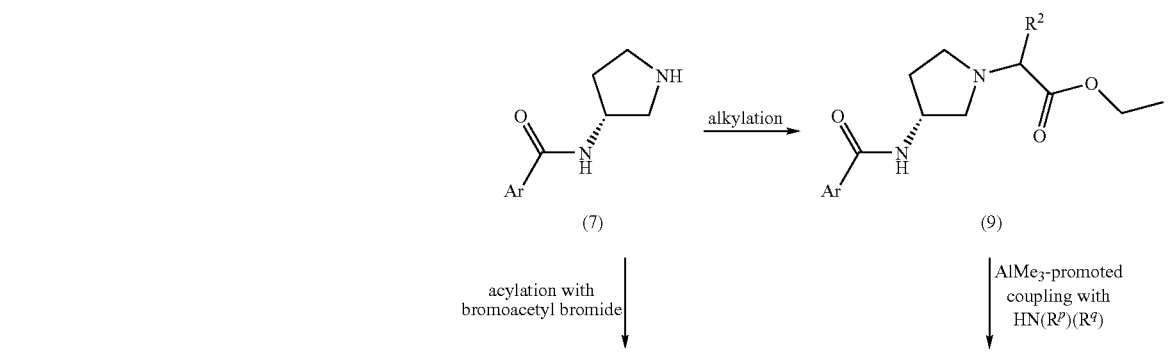

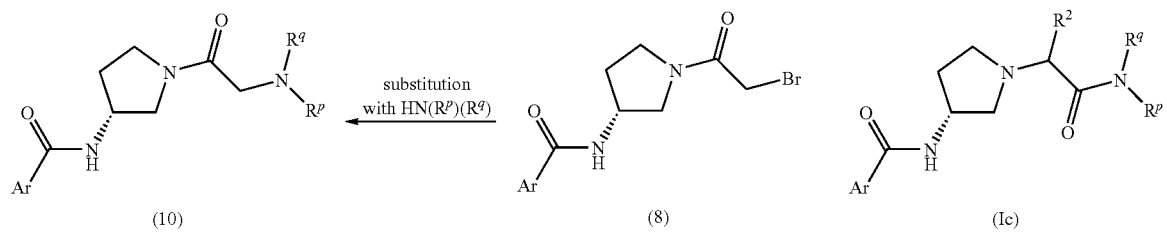

Ar in the scheme is $Y^3$—$Y^2$— as defined before. $R^p$ in the scheme is hydrogen and $R^q$ in the scheme is —$X^2$—$X^3$ as defined before. $R^2$ in the scheme is as defined before.

Intermediate (6): The starting aminopyrrolidine is coupled with a carboxylic acid Ar—COOH as described for the preparation of intermediate (4). Particular conditions are BOP, DIPEA and DMF.

Intermediate (7): Intermediate (6) is deprotected as described for the preparation of intermediate (2).

Intermediate (8): Intermediate (7) is reacted with bromoacetyl bromide in a solvent such as THF, methylene chloride, DMF or acetonitrile in the presence of an organic base such as TEA or DIPEA and reacted under an argon atmosphere at 0° C. to 50° C. for 1 hr-72 hrs. Particular conditions are THF and TEA.

Intermediate (10): Intermediate (8) is reacted with an amine $HN(R^p)(R^q)$ in a solvent such as THF, methylene chloride, DMF or acetonitrile in the presence of an organic base such as TEA or DIPEA and reacted under an argon atmosphere at 0° C. to 50° C. for 1 hr-72 hrs. A catalytic amount of an additive such as tetrabutylammonium iodide can be added. Particular conditions are THF, TEA and tetrabutylammonium iodide.

Intermediate (9): Intermediate (7) is alkylated with an appropriate alkylbromide as described for the preparation of intermediate (1).

Final product (Ic): Intermediate (9) is reacted with an aniline $HN(R^p)(R^q)$ as described for the preparation of final product (Ia).

3 Synthesis starting from
N-Boc-trans-4-amino-L-proline methyl ester; via
ester intermediate (14)

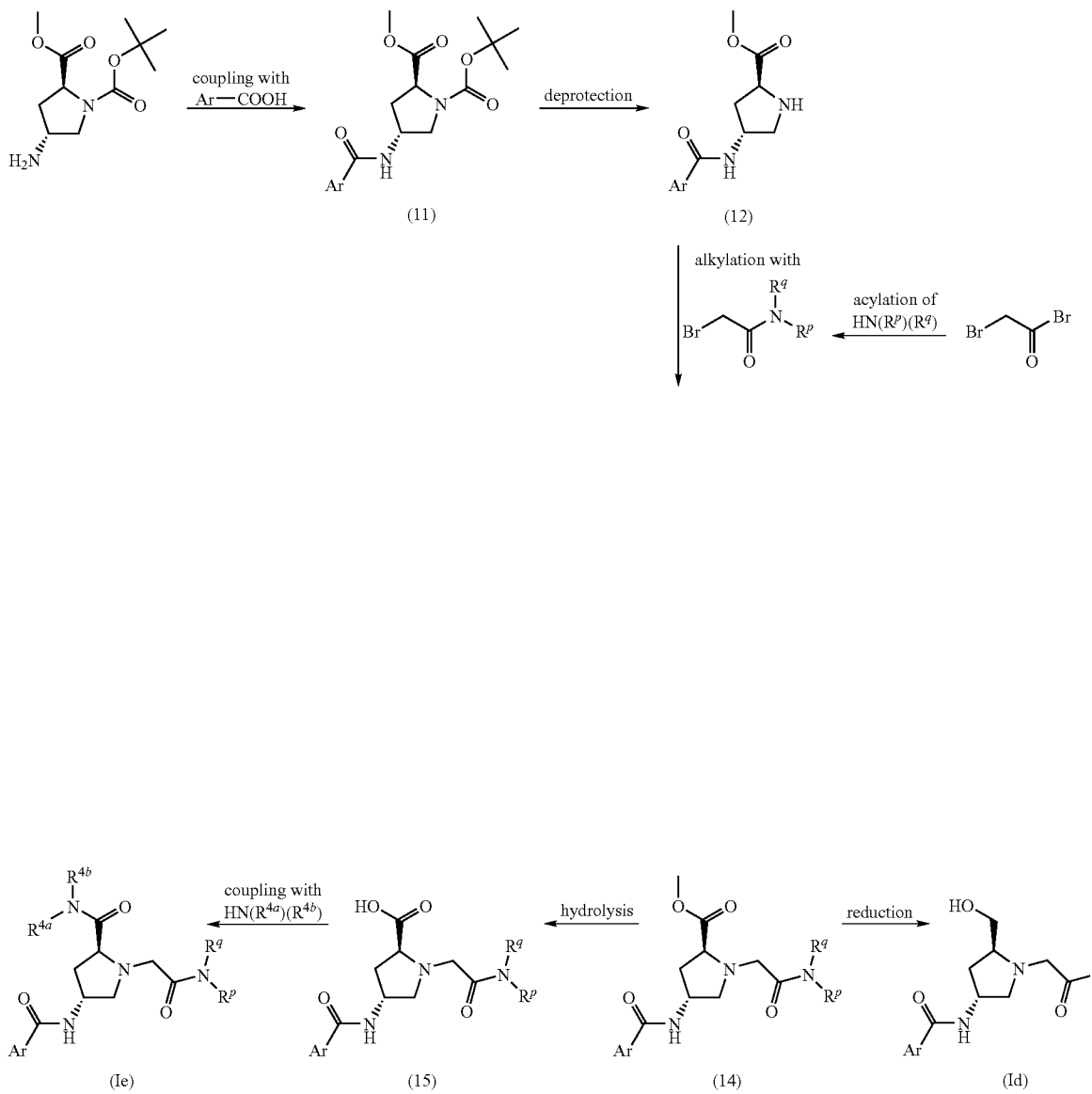

Ar in the scheme is $Y^3$—$Y^2$ as defined before. $R^p$ in the scheme is hydrogen and $R^q$ in the scheme is —$X^2$—$X^3$ as defined before. $(R^{4a})(R^{4b})N$— is —NH-hydroxy $C_{1-6}$ alkyl, —$N(C_{1-6}$ alkyl)(hydroxy $C_{1-6}$ alkyl), —NH—$C_{1-6}$ alkyl, —NH-halo $C_{1-6}$ alkyl or —NH—$C_{1-6}$ alkyl-$C_{3-7}$ cycloalkyl.

Intermediate (11): N-Boc-trans-4-amino-L-proline methyl ester is coupled with a carboxylic acid Ar—COOH as described for the preparation of intermediate (4). Particular conditions are BOP, DIPEA and DMF.

Intermediate (12): Intermediate (11) is deprotected as described in the preparation of intermediate (2).

Intermediate (13): An amine $HN(R^p)(R^q)$ is reacted with bromoacetyl bromide in a solvent such as THF, methylene chloride, DMF or acetonitrile in the presence of an organic base such as TEA or DIPEA and reacted under an argon atmosphere at 0° C. to 50° C. for 1 hr-72 hrs. Particular conditions are THF and TEA.

Intermediate (14): Intermediate (12) is alkylated with intermediate (13) as described for the preparation of intermediate (1).

Intermediate (15): Intermediate (13) is hydrolyzed as described for the preparation of intermediate (5).

Final product (Ie): Intermediate (15) is coupled with an amine $HN(R^{4a})(R^{4b})$ as described for the preparation of intermediate (4).

Final product (Id): Intermediate (14) is reduced using agents such as $NaBH_4$, $NaBH_4/LiCl$ in solvents such as MeOH, EtOH or THF.

4. Synthesis starting from N-Boc-trans-4-amino-L-proline methyl ester; via hydroxymethyl intermediate (16)

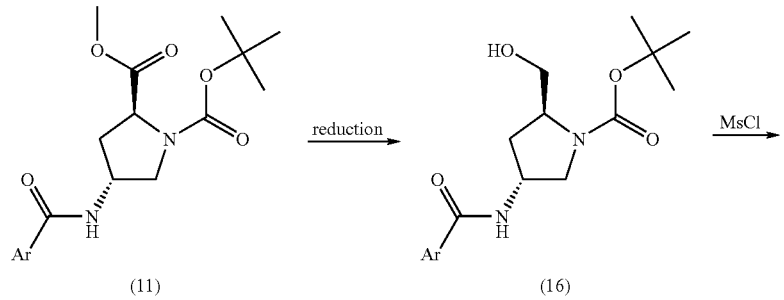

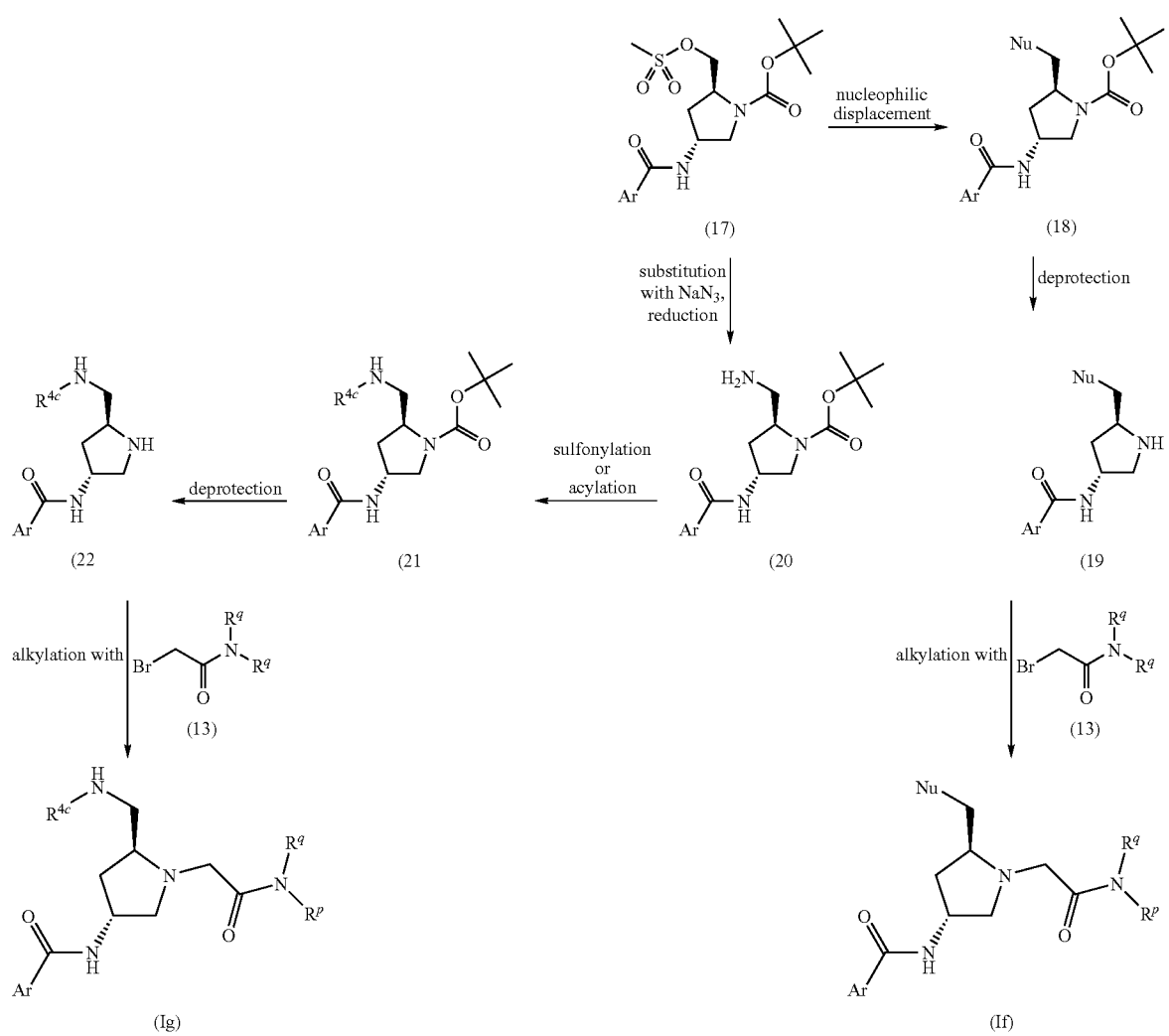

Ar in the scheme is $Y^3$—$Y^2$ as defined before. $R^p$ in the scheme is hydrogen and $R^q$ in the scheme is —$X^2$—$X^3$ as defined before. ($R^{4c}$)NH— is $C_{1-6}$ alkyl-sulfonylamino, or $C_{1-6}$ alkyl-carbonylamino, and Nu is hydroxy, $C_{1-6}$ alkoxy, halo$C_{1-6}$ alkoxy, halo, heterocyclyl, $C_{1-6}$ alkyl-sulfonylamino, ($C_{1-6}$ alkyl-sulfonyl)($C_{1-6}$ alkyl)amino, $C_{1-6}$ alkyl carbonylamino, di-$C_{1-6}$ alkyl substituted amino, mono-$C_{1-6}$ alkyl substituted amino, $C_{3-7}$ cycloalkylamino, heterocyclylamino, ($C_{3-7}$ cycloalkyl)($C_{1-6}$ alkyl)amino or (heterocyclyl)($C_{1-6}$ alkyl)amino.

Intermediate (16): Intermediate (11) is reduced as described for the preparation of final product (14).

Intermediate (17): Intermediate (16) is reacted with methanesulfonyl chloride in a solvent such as THF, methylene chloride, DMF or acetonitrile in the presence of an organic base such as TEA or DIPEA and reacted under an argon atmosphere at 0° C. to 50° C. for 1 hr-72 hrs. Particular conditions are THF and TEA. Other particular conditions are DIPEA and methylene chloride.

Intermediate (18): Intermediate (17) is reacted with an appropriate nucleophile according to general methods known per se, e.g. as well known to those skilled in the art and/or as described hereinafter and/or as described in the Examples or in analogy to these methods. For example the mesylate (17) can be reacted with an excess of a primary or secondary amine in a solvent such as THF, methylene chloride, DMF or acetonitrile. If necessary, an organic base such as TEA or DIPEA can be added. The reaction proceeds at 0° C. to 50° C. within 1 hr-72 hrs under an argon atmosphere. Particular conditions are an excess of reacting amine in THF. Alternatively, the mesylate (17) can be reacted with the sodium salt or the potassium salt of an alcohol in DMF, THF or the corresponding alcohol as solvent. If not commercially available, the alcoholate is obtained by deprotonation of the alcohol with NaH in DMF or THF. After addition of the mesylate, the reaction proceeds at 0° C. to 50° C. within 1 hr-72 hrs under an argon atmosphere. Alternatively, the mesylate (17) can be reacted the sodium salt of a lactam which is generated by deprotonation with NaH in DMF or THF. After addition of the mesylate (17), the reaction then proceeds at 0° C. to 50° C. within 1 hr-72 hrs under an argon atmosphere.

Intermediate (19): Intermediate (18) is deprotected as described in the preparation of intermediate (2).

Final product (If): Intermediate (19) is alkylated with intermediate (13) as described for the preparation of intermediate (1).

Intermediate (20): Mesylate (17) is reacted with $NaN_3$ in DMF. The resulting azide intermediate is then reduced in a Staudinger reaction with $PPh_3$ in $H_2O$/THF or alternatively hydrogenated with hydrogen under normal pressure or by transfer hydrogenation with a catalyst such as $PtO_2$, Pd—C or Raney nickel in solvents such as MeOH, EtOH, $H_2O$, dioxane, THF, HOAc or mixtures thereof. Staudinger conditions are particularly pointed out.

Intermediate (21): Intermediate (20) is reacted with an acyl chloride or a sulfonyl chloride in a solvent such as THF, methylene chloride, DMF or acetonitrile in the presence of an organic base such as TEA or DIPEA. The reaction proceeds at 0° C. to 50° C. within 1 hr-72 hrs under an argon atmosphere. Particular conditions are TEA and methylene chloride.

Intermediate (22): Intermediate (21) is deprotected as described in the preparation of intermediate (2).

Final product (Ig): Intermediate (22) is alkylated with intermediate (13) as described for the preparation of intermediate (1).

5 Synthesis starting from 6-oxa-3-aza-bicyclo[3.1.0]hexane-3-carboxylic acid tert-butyl ester; hydroxy+alkoxy compounds

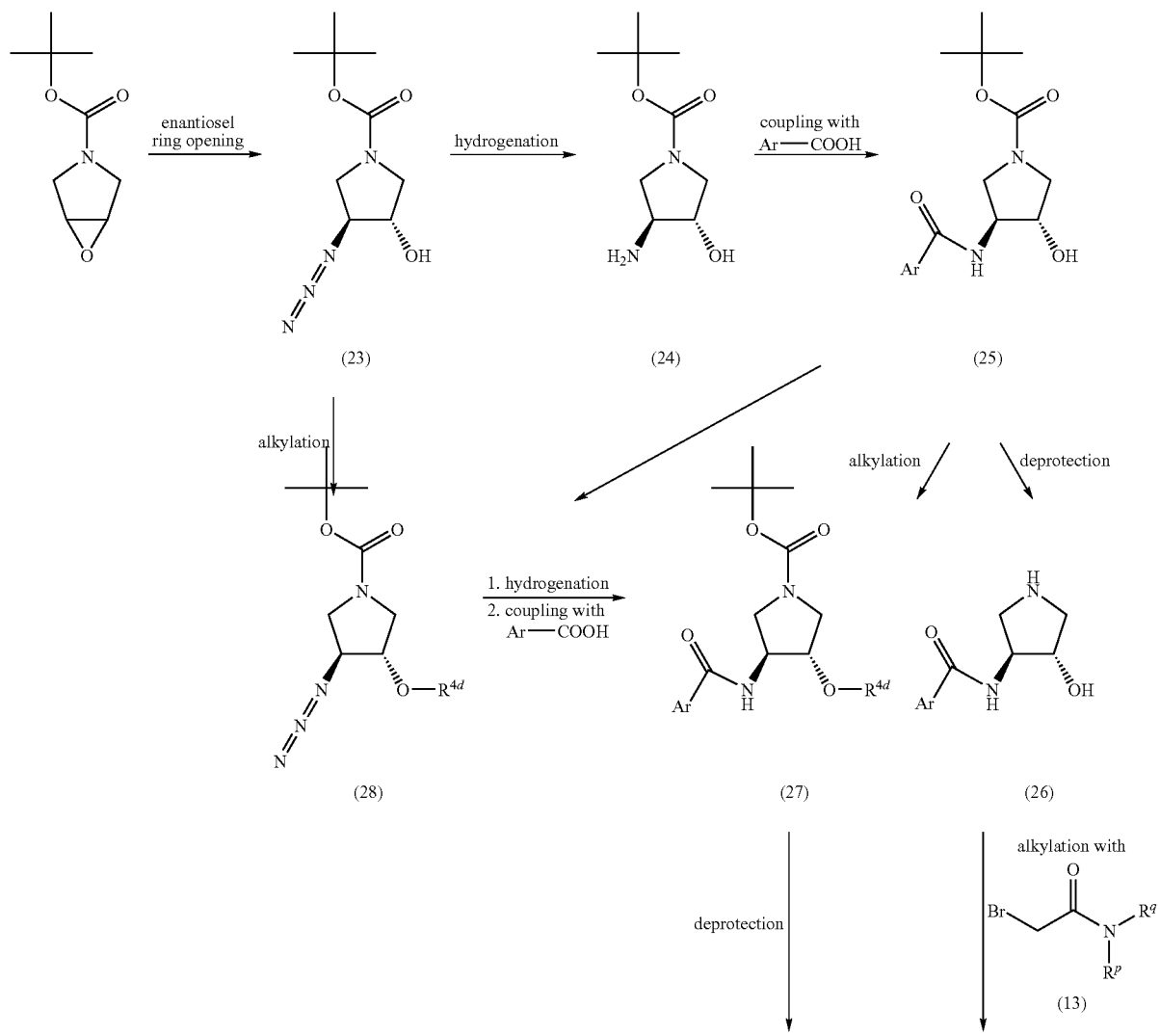

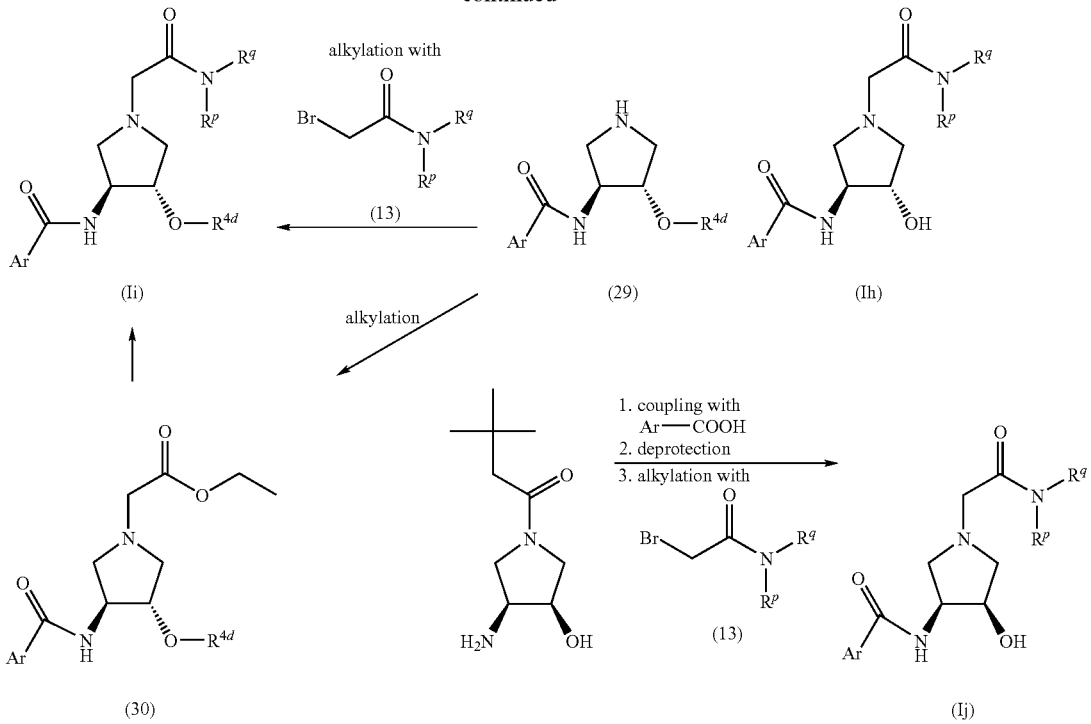

Ar in the scheme is $Y^3$—$Y^2$ as defined before. $R^p$ in the scheme is hydrogen and $R^q$ in the scheme is —$X^2$—$X^3$ as defined before. $R^{4d}$ is $C_{1-6}$ alkyl, halo $C_{1-6}$ alkyl or —$C_{1-6}$ alkyl-OH.

Intermediate (23): 6-Oxa-3-aza-bicyclo[3.1.0]hexane-3-carboxylic acid tert-butyl ester is subjected to an enantioselective ring-opening with trimethylsilyl azide in analogy to S. E. Schaus, J. F. Larrow, E. N. Jacobsen in *Journal of Organic Chemistry*, 1997, 62(12), 4197.

Intermediate (24): Intermediate (23) is hydrogenated with hydrogen under normal pressure or by transfer hydrogenation with a catalyst such as $PtO_2$, Pd—C or Raney nickel in solvents such as MeOH, EtOH, $H_2O$, dioxane, THF, HOAc or mixtures thereof. Alternatively, the azide can be converted to the corresponding amine by treatment with triphenylphosphine in $H_2O$/THF. Particular conditions are hydrogenation with hydrogen in the presence of $PtO_2$ in MeOH as solvent.

Intermediate (25): Intermediate 24 is coupled with a carboxylic acid Ar—COOH as described for the preparation of intermediate (4). Particular conditions are BOP, DIPEA and DMF.

Intermediate (26): Intermediate (25) is deprotected as described for the preparation of intermediate (2).

Final product (Ih): Intermediate (26) is alkylated with intermediate (13) as described for the preparation of intermediate (1).

Intermediate (27): Intermediate (25) is alkylated with an appropriate alkyl halide either by promoting the reaction with $Ag(I)_2O$ in a solvent such as toluene, THF or acetonitrile. Elevated temperatures up the boiling point of the respective solvents, multiple additions of alkyl halide and prolonged reaction times up to 6 days are required in order to drive the reaction to completion.

Alternatively, the alcohol can be deprotonated with treatment with sodium hydride in DMF for 1 hr and then reacted with an appropriate alkyl halide or triflate for 1 hr-48 hrs. Intermediate (27) can also be obtained by alkylation of intermediate (23). The alkylation can be carried out in the same way as the alkylation of intermediate (25). Subsequently, intermediate (28) is hydrogenated as described for the preparation of intermediate (24) and coupled with a carboxylic acid Ar—COOH as described for the preparation of intermediate (4). Particular conditions are $H_2$, $PtO_2$ in MeOH for the hydrogenation and BOP, DIPEA and DMF for the coupling step.

Intermediate (29): Intermediate (27) is converted to intermediate (29) as described for the preparation of intermediate (2).

Final product (Ii): Intermediate (29) is alkylated with intermediate (13) as described for the preparation of intermediate (1).

Alternatively, final product (Ii) can be obtained by alkylation of intermediate (29) with bromoacetic acid ethylester as described for the preparation of intermediate (1). Intermediate (30) is then reacted with an aniline $HN(R^p)(R^q)$ as described for the preparation of final product (Ia).

Final product (Ij): (3S,4R)-3-amino-4-hydroxy-pyrrolidine-1-carboxylic acid tert-butyl ester (described by S. E. Schaus, J. F. Larrow, E. N. Jacobsen in *Journal of Organic Chemistry*, 1997, 62(12), 4197) was reacted with a carboxylic acid Ar—COOH, then deprotected and finally alkylated with intermediate (13) using the procedures described for the preparation of intermediates (4), (2) and (1) respectively.

6 Synthesis starting from
6-oxa-3-aza-bicyclo[3.1.0]hexane-3-carboxylic acid
tert-butyl ester; syntheses via keto intermediate

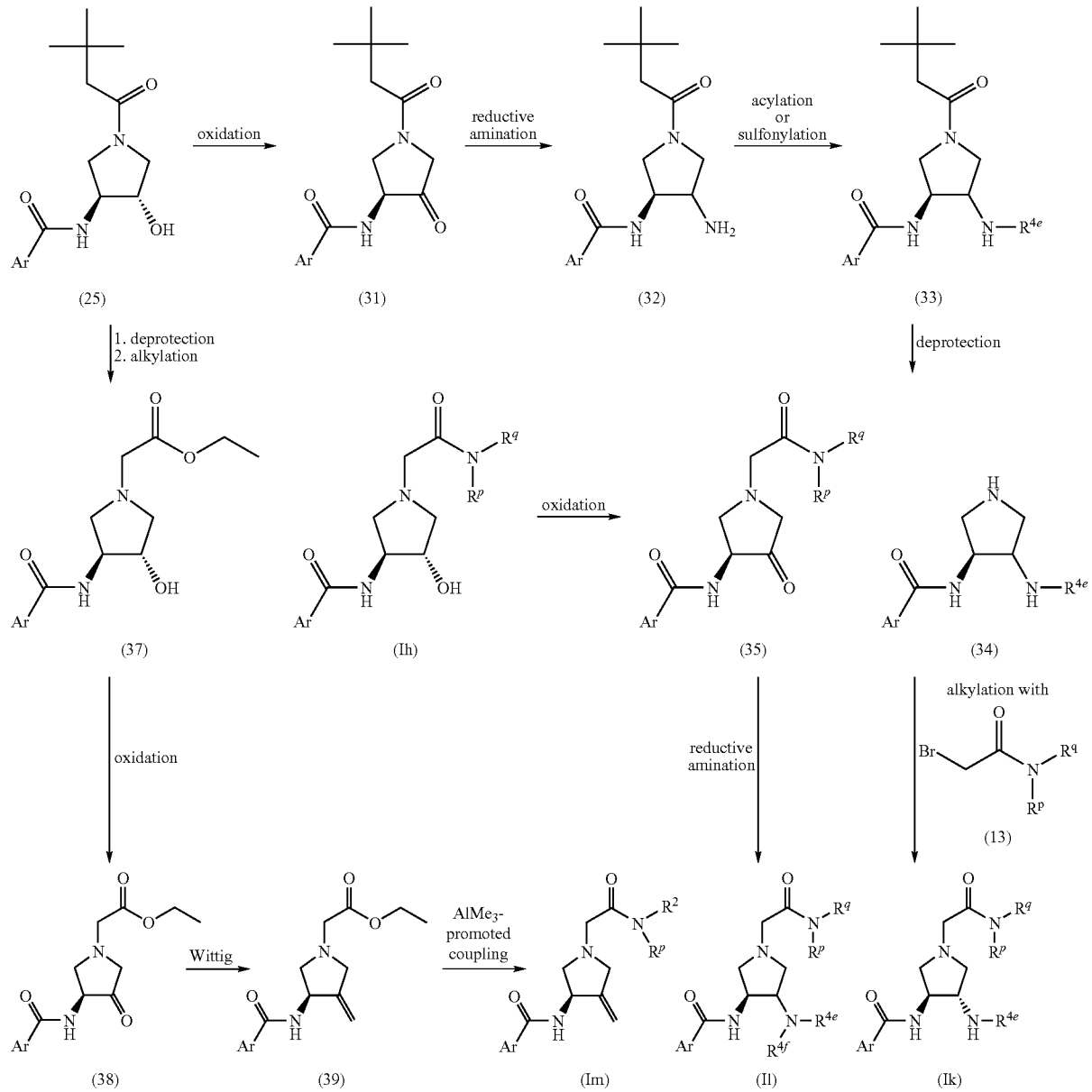

Ar in the scheme is $Y^3$—$Y^2$ as defined before. $R^p$ in the scheme is hydrogen and $R^q$ in the scheme is —$X^2$—$X^3$ as defined before. $(R^{4e})(R^{4f})N$— is di-$C_{1-6}$ alkyl substituted amino, di-halo$C_{1-6}$ alkyl substituted amino, ($C_{1-6}$ alkylcarbonyl)($C_{1-6}$ alkyl)amino-, ($C_{1-6}$ alkoxycarbonyl)($C_{1-6}$ alkyl)amino- or ($C_{1-6}$ alkylsulfonyl)($C_{1-6}$ alkyl)amino-, $(R^{4e})NH$— is mono-$C_{1-6}$ alkyl substituted amino, mono-halo$C_{1-6}$ alkyl substituted amino, $C_{1-6}$ alkyl-sulfonylamino- or $C_{1-6}$ alkyl-carbonylamino-.

Intermediate (31): Intermediate (25) is oxidized using the Parikh-Doering procedure (sulfurtrioxide-pyridine complex, TEA, DMSO/methylene chloride). The reaction proceeds at 0° C.—r.t. for 2-18 hrs under an argon atmosphere.

Intermediate (32): Intermediate (31) is subjected to eductive amination with an ammonium salt such as ammonium acetate or ammonium chloride using a reducing agent such as e.g. $NaBH_4$, $LiBH_4$, $Li(CN)BH_3$ or $Na(CN)BH_3$ in a solvent such as an alcohol, e.g. MeOH or an ether, e.g. THF. A Lewis acid such as $Ti(OiPr)_4$ can be added to facilitate the reaction. In this case the ammonium salt has to be liberated with an organic base such as TEA or DIPEA. The reaction proceeds at a temperature of −10 to 60° C. Particular conditions are $Ti(O-iPr)_4$, DIPEA, $NaBH_4$ and EtOH. The products obtained consist of a mixture of epimers at the newly formed stereo center.

Intermediate (33): Intermediate (32) is reacted with an acyl chloride or a sulfonyl chloride in a solvent such as THF, methylene chloride, DMF or acetonitrile in the presence of an organic base such as TEA or DIPEA. The reaction proceeds at 0° C. to 50° C. within 1 hr-72 hrs under an argon atmosphere. Particular conditions are TEA and methylene chloride.

Intermediate (34): Intermediate (33) is converted to intermediate (34) as described for the preparation of intermediate (2).

Final product (Ik): Intermediate (34) is alkylated with intermediate (13) as described for the preparation of intermediate (1).

such as THF or DMSO. Alternatively, the exomethylene group can be introduced using reagents as the Tebbe, the Petasis or the Nysted reagent.

Final product (Im): Intermediate (39) is reacted with an aniline HN($R^p$)($R^q$) as described for the preparation of final product (Ia).

7. Synthesis starting from
6-oxa-3-aza-bicyclo[3.1.0]hexane-3-carboxylic acid tert-butyl ester; fluoro derivatives

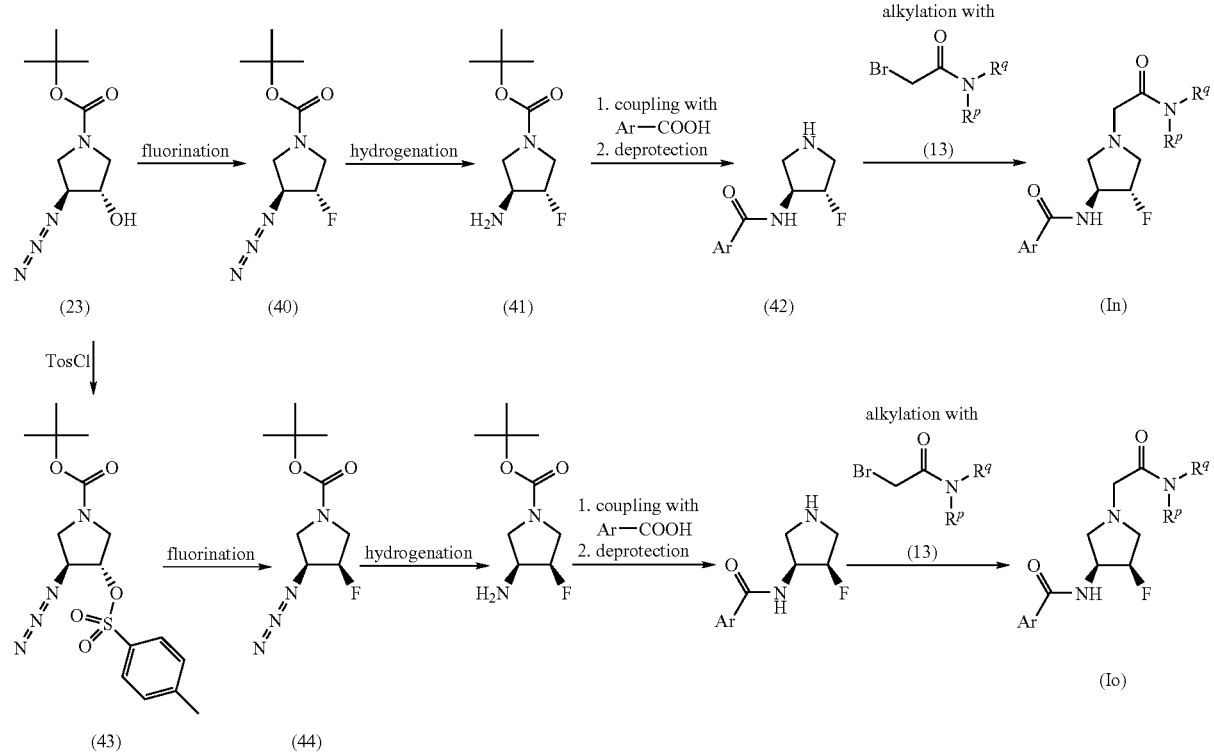

Intermediate (35): Final product (Ih) is oxidized as described for the preparation of intermediate (31).

Final product (Il): Intermediate (35) is subjected to reductive amination with a commercial amine using a reducing agent such as e.g. NaBH$_4$, LiBH$_4$, Li(CN)BH$_3$ or preferably Na(CN)BH$_3$ in a solvent such as an alcohol, e.g. MeOH or an ether, e.g. THF and an acid e.g. HCl, H$_2$SO$_4$, H$_3$PO$_4$ or a carboxylic acid, preferably CH$_3$COOH at a temperature of −10 to 60° C., in particular at 20° C. for 1-40 h. The products obtained consist of a mixture of epimers at the newly formed stereo center.

Intermediate (39): The Boc protecting group of intermediate (25) is cleaved as described for the preparation of intermediate (2), then the liberated amine is alkylated with bromoacetic acid ethylester as described for the preparation of intermediate (1).

Intermediate (38): Intermediate (37) is oxidized as described for the preparation of intermediate (31).

Intermediate (39): Intermediate (38) is converted to the exomethylene derivative under Wittig conditions using methyltriphenylphosphonium bromide in the presence of a base such as potassium tert-butylate or sodium hydride in a solvent Ar in the scheme is $Y^3$—$Y^2$ as defined before. $R^p$ in the scheme is hydrogen and $R^q$ in the scheme is —$X^2$—$X^3$ as defined before.

Intermediate (40): Intermediate (23) is fluorinated with bis(2-methoxyethyl)amino-sulphur trifluoride according to a method described by D. Bouzard et al. in *J. Med. Chem.* 1990, 33, 1344-1353.

Intermediate (41): Intermediate (40) is reduced as described for the preparation of intermediate (24).

Intermediate (42): Intermediate (41) is coupled with an aryl carboxylic acid as described for the preparation of intermediate (4). Then the Boc group is cleaved as described for the preparation of intermediate (2).

Final product (In): Intermediate (42) is alkylated with intermediate (13) as described for the preparation of intermediate (1).

Intermediate (43): Intermediate (23) is reacted with 4-toluolenesulfonyl chloride as described for the preparation of intermediate (17).

Intermediate (44): Intermediate (43) is reacted with a fluoride salt such as tetrabutyl ammonium fluoride, triethylammonium hydrofluoride, cesium fluoride or tetrabutylammonium triphenyldifluorosilicate in a solvent such as THF, EtOAc, acetonitrile or DMF. The reaction proceeds at –10° C. to 100° C. for 2-18 hrs under an argon atmosphere. Particular conditions are 1M tetrabutylammonium fluoride in THF.

Final product (Io): Intermediate (44) is converted to the final product (Io) using analogous procedures as described for the preparation of final product (In).

8. Synthesis starting from
(3R,4R)-Pyrrolidine-1,3,4-tricarboxylic acid
1-tert.-butyl ester 3-ethyl ester $C_{1-6}$ alkyl-sulfonylamino-, ($C_{1-6}$ alkyl-sulfonyl)($C_{1-6}$ alkyl)amino-, $C_{1-6}$ alkyl-carbonylamino-, di-$C_{1-6}$ alkyl substituted amino-, mono-$C_{1-6}$ alkyl substituted amino-, $C_{3-7}$ cycloalkylamino-, heterocyclyl-amino-, ($C_{3-7}$ cycloalkyl)($C_{1-6}$ alkyl)amino- or (heterocyclyl)($C_{1-6}$ alkyl)amino-.

Intermediate (45): Synthesis of intermediate (45) is described in R. M. Rodriguez Sarmiento, B. Wirz, H. Iding, *Tetrahedron Asymmetry*, 14, 2003, 1547-1551.

Intermediate (46): The starting carboxylic acid is reacted with a diazo-transfer reagent such as diphenylphosphoryl

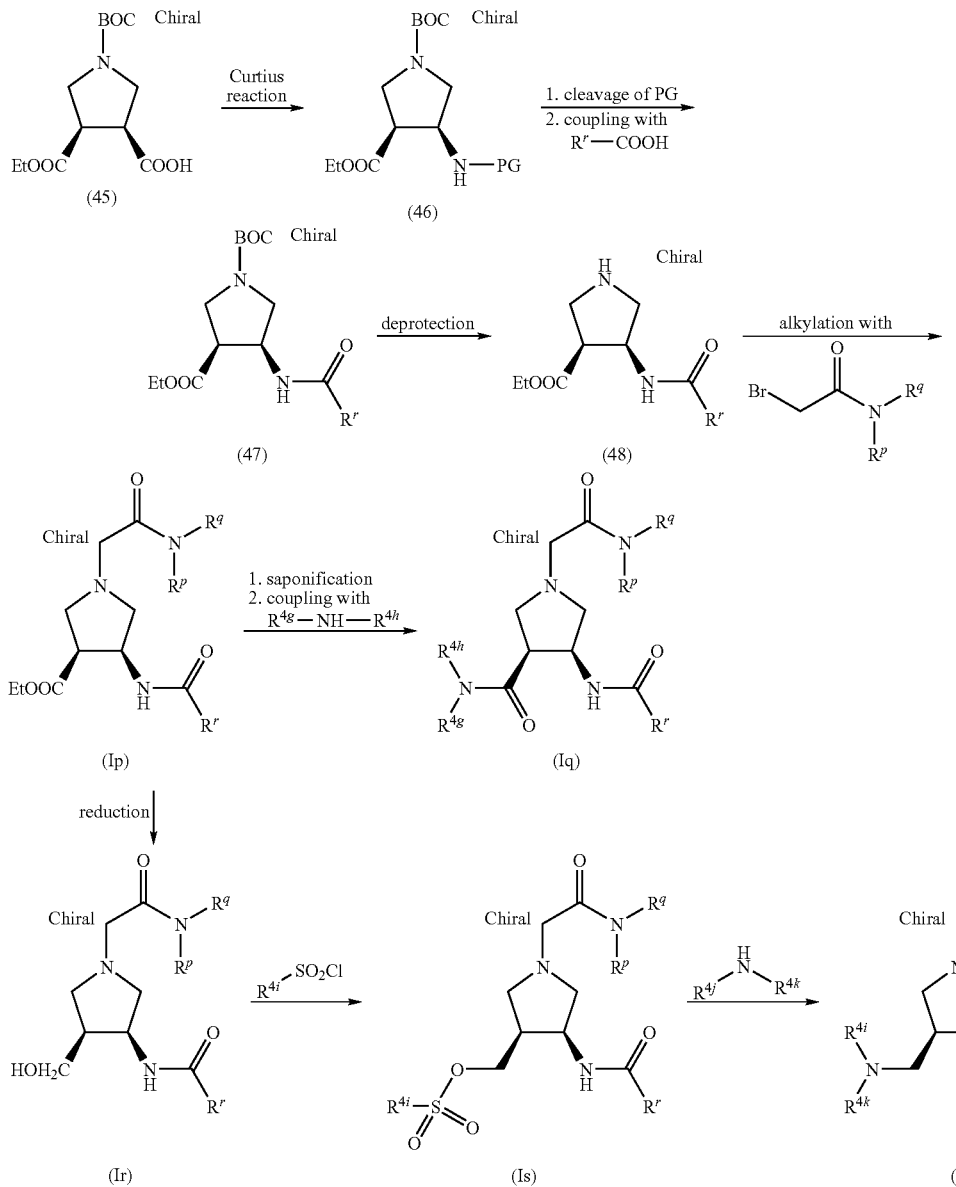

$R^p$ in the scheme is hydrogen and $R^q$ in the scheme is —$X^2$—$X^3$ as defined before. PG means a protecting group. $R^r$ in the scheme is $Y^3$—$Y^2$ as defined before. ($R^{4g}$)($R^{4h}$)N— is —NH-hydroxy $C_{1-6}$ alkyl, —N($C_{1-6}$ alkyl)(hydroxy $C_{1-6}$ alkyl), —NH—$C_{1-6}$ alkyl, —NH-halo $C_{1-6}$ alkyl or —NH—$C_{1-6}$ alkyl-$C_{3-7}$ cycloalkyl. $R^{4i}$ is $C_{1-6}$ alkyl. ($R^{4j}$)($R^{4k}$)N— is azide, sodium azide, 4-acetamidobenzene sulfonyl azide, p-toluene sulfonyl azide, etc. in the presence of a suitable alcohol such as benzyl alcohol (to yield Z), (4-methoxyphenyl)methanol (to yield MOZ), 9-fluorenylmethanol (to yield Fmoc), 2-(trimethylsilyl)ethanol (to yield Teoc) in an organic solvent such as toluene, acetonitrile, DMF, DMA, NMP, DMSO at elevated temperature between 50-120° C. to yield the corresponding protected intermediate (46) within 3-24 h. Particular conditions involve the use of diphenylphosphoryl azide in the presence of 2-(trimethylsilyl)ethanol in toluene between 70-90° C. within 8-18 h.

Intermediate (47): Cleavage of the protecting group PG is accomplished by known methods such as hydrogenation for Z, treatment with weak acids for MOZ such as TFA or toluene sulfonic acid, treatment with fluorides for Teoc in a suitable solvent such as acetonitrile, THF, ethanol, methanol, dioxane, etc. Particular conditions involve the treatment of Teoc protected intermediate (46) with TBAF in acetonitrile at elevated temperature between 40-80° C. After deprotection an activated carboxylic acid is added to the reaction mixture to yield directly intermediate (47) between 0-100° C. for 3-72 h. Activation reagents are CDI, EDCI, BOP, BOP-Cl, TBTU, EDCI/HOBt, EDCI/DMAP, isobutyl chloroformate, etc. in the presence of a base like TEA, DIPEA, N-methylmorpholine etc. at 0° C. to 100° C. within 2-72 h. Particular conditions are CDI and isobutyl chloroformate in the presence of DIPEA or N-methylmorpholine at 25-80° C. in acetonitrile for 18-72 h.

Intermediate (48): Deprotection of intermediate (47) is effected by treatment with a mineral acid such as HCl, HBr, $H_2SO_4$ or $H_3PO_4$ or a carboxylic acid such as TFA, in a solvent such as $CH_2Cl_2$, dioxane or HOAc at 0 to 60° C. Particular conditions are 4N HCl in dioxane at 25° C.

Final product (Ip): The amine (48) is dissolved in a suitable solvent such as THF, acetonitrile or DMF and treated with intermediate (13) in the presence of a base like TEA or DIPEA and reacted under an argon atmosphere at 0° C. to 50° C. for 1 hr-72 hrs. Particular conditions are THF and TEA.

Final product (Iq): The ester (Ip) is dissolved in a suitable solvent like methanol, ethanol, THF, or water and treated with LiOH, NaOH or KOH for 0.5-24 h at 0-80° C. to yield the corresponding Li, Na or K-salt of the carboxylic acid. This carboxylate is activated reacted with an amine $R^{4g}$—NH—$R^{4h}$ as described for intermediate (47). Particular conditions are DMF, THF and CDI at 25° C.

Final product (Ir): The ester (Ip) is dissolved in a suitable solvent such as THF, methanol, ethanol, or isopropanol and reduced with an appropriate reducing agent such as $NaBH_4$ or $LiBH_4$ at 0-80° C. for 1-72 h. Particular conditions are $NaBH_4$ in ethanol at 25° C. for 72 h.

Final product (Is): The alcohol (Ir) is dissolved in a suitable solvent such as dichloromethane, THF, acetonitrile, or pyridine and treated with an appropriate sulfonylchloride in presence of an appropriate base such as DIEA, TEA or pyridine at −10-80° C. for 0.5-48 h. Particular conditions are dichloromethane and pyridine at 0-25° C. for 18-48 h.

Final product (It): The sulfate (Is) is dissolved in a suitable solvent such as THF, DMF, NMP, DMA, or acetonitrile and treated with an excess of an appropriate amine at 25-120° C. for 2-72 h. Particular conditions are DMF at 25° C. for 72 h.

9. Synthesis of 2- and 3-aminomethyl-pyrrolidines

The following scheme depicts only the 3-aminomethyl-pyrrolidines. The same reaction sequences and conditions were applied for the 2-aminomethyl-pyrrolidines as well.

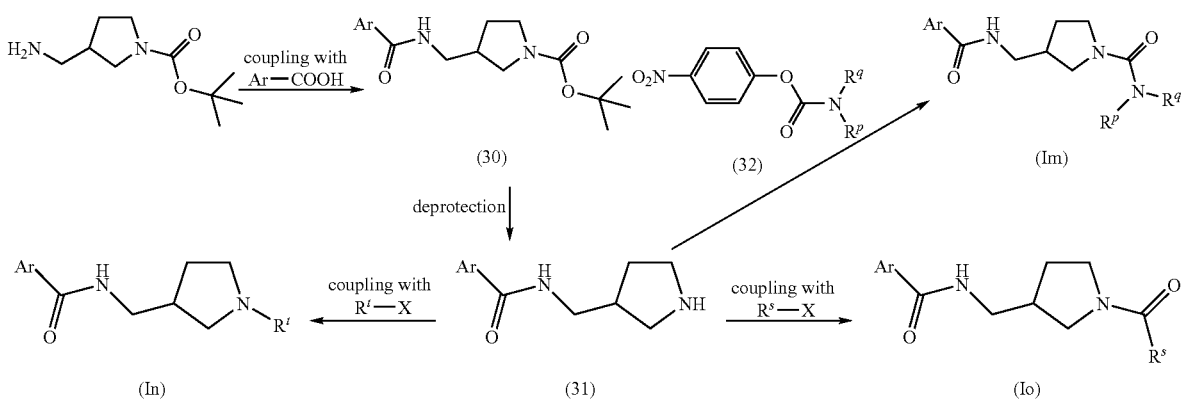

Ar in the scheme is $Y^3$—$Y^2$ as defined before. $R^p$ in the scheme is hydrogen and $R^q$ in the scheme is —$X^2$—$X^3$ as defined before. $R^s$ and $R^t$ in the scheme are —$X^2$—$X^3$ as defined before.

Intermediate (49): The starting amine is reacted with a carboxylic acid Ar—COOH in a suitable solvent such as $CH_2Cl_2$, DMF, acetonitrile, THF. Activation is effected by an amide coupling reagent such as BOP, BOP-Cl, TBTU, EDCI, EDCI/DMAP and an additive such as HOBT, N-hydroxysuccinimide or N-hydroxy-2-pyridone in the presence of a base like TEA, DIPEA, N-methylmorpholine etc. at 0° C. to 100° C. Reaction times ranged from 1 hr to 72 hrs. Particular conditions are THF, EDCI, HOBT and TEA at 60° C.

Intermediate (50): Deprotection of intermediate (49) is effected by treatment with a mineral acid such as HCl, HBr, $H_2SO_4$ or $H_3PO_4$ or a carboxylic acid such as TFA, in a solvent such as $CH_2Cl_2$, dioxane or HOAc at 0 to 60° C. Particular conditions are TFA in $CH_2Cl_2$ at 22° C.

Intermediate (51): Preparation of intermediate (51) is accomplished in a suitable solvent such as $CH_2Cl_2$, DMF, THF. Activation of the amine $HN(R^p)(R^q)$ is effected with a chloroformate such as phenyl chloroformate, 2-nitrophenyl- or 4-nitrophenyl chloroformate, and a base like, DIPEA, N-methylmorpholine, pyridine etc. at 0° C. to 40° C. Particular conditions are $CH_2Cl_2$/DMF, 4-nitrophenyl chloroformate and pyridine at 22° C.

Final product (Iu): Intermediate (50) is reacted with intermediate (51) in a suitable solvent such as DMF, DMSO, or THF at 0 to 120° C. Particular conditions are DMF at 80° C.

Final product (Iv): Intermediate (50) is reacted with a carboxylic acid $R^s$—COOH under conditions described for the preperation of intermediate (49).

Final product (Iw): Intermediate (50) is reacted in analogy to M. Hepperle et al. (Tetrahedron Letters, 2002, 43, 3359) with a halogenated aromatic compound R$^t$—X, whereas X equals Cl, Br, I in a suitable solvent such as toluene, DMF, or THF. The coupling is effected preferably with a catalyst such as rac-2,2'-bis-(diphenylphosphino)-1,1'-binaphtaline and an additive such as tris-(dibenzylideneacetone)-dipalladium chloroform complex and a base such as KO-tBu or NaOt-Bu at 20 to 120° C. Particular conditions are X equals I in THF/toluene, NaO-tBu at 90° C.

10. Synthesis of 4-substituted 3-aminomethyl-pyrrolidines

10.1 Synthesis of 4-hydroxy-3-aminomethyl-pyrrolidines

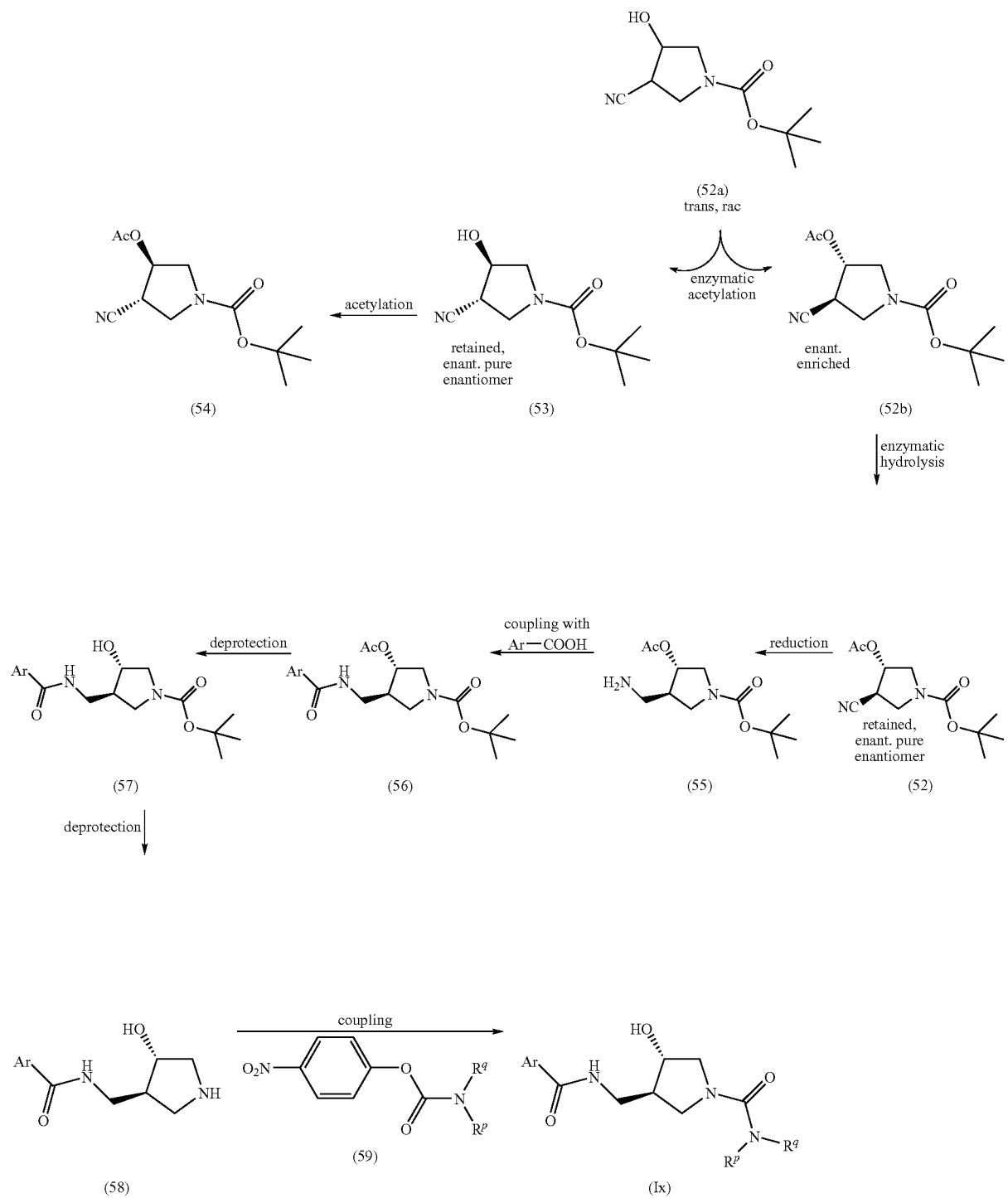

Ar in the scheme is $Y^3$—$Y^2$ as defined before. $R^p$ in the scheme is hydrogen and $R^q$ in the scheme is —$X^2$—$X^3$ as defined before.

Intermediates (53) and (52b): The starting trans, rac-3-cyano-4-hydroxy-pyrrolidine-1-carboxylic acid tert-butyl ester (52a), prepared according to C. Y. Hong et al. (Bioorganic Medicinal Chemistry Letters, 2003, 13, 4399), by D. J. Kim et al. (Journal of Medicinal Chemistry, 1997, 40, 3584) or by S. U. Hansen & M. Bols (Acta Chemica Scandinavica, 1997, 52, 1214), is resolved by enantioselective enzymatic acetylation. Particular conditions are Lipase AK in an anhydrous organic solvent using vinyl acetate as the acyl donor and a conversion degree beyond 50%. Chromatographic separation of the reaction products provides the retained, enantiomerically pure (R,R)-alcohol (53) and the enantiomerically enriched acetate (52b).

Intermediate (54): The chiral intermediate (53) is acetylated by conventional chemical or enzymatic methods to give the respective (R,R)-acetate (54) in high enantiomeric excess.

Intermediate (52): Enantiomerically enriched intermediate (52b) (or, alternatively, trans-racemic acetate) is subjected to an enantioselective enzymatic hydrolysis. Preferentially lipase from *Candida antarctica*, form B, is applied to a vigorously stirred substrate/buffer emulsion kept constant near neutral pH using a pH-stat. After extraction of the reaction products and chromatographic separation the retained, enantiomerically pure (S,S)-acetate (52) is obtained.

Intermediate (55): Intermediate (52) is hydrogenated with hydrogen under normal or elevated pressure or by transfer hydrogenation with a catalyst such as $PtO_2$ or Pd—C or reduced with diborane in solvents such as MeOH, EtOH, $H_2O$, dioxane, THF, HOAc or mixtures thereof. Particular conditions are hydrogenation with hydrogen under normal pressure in the presence of $PtO_2$ in EtOH as solvent.

Intermediate (56): Intermediate (55) is reacted with a carboxylic acid Ar—COOH according to the procedure for the preparation of intermediate (49).

Intermediate (57): Intermediate (56) is deprotected with $K_2CO_3$ in MeOH/$H_2O$ or preferrably in 50% ammonia in MeOH.

Intermediate (58): Intermediate (57) is deprotected according to the procedure for the preparation of intermediate (50).

Final product (Ix): Intermediate (58) is coupled with intermediate (59) according to the procedure for the preparation of final product (Iu).

The reaction sequence from intermediate (52) through to final product (Ix) can, optionally, also be carried out starting from the antipodal intermediate (54).

Preparation of (S,S)—N-Boc-3-cyano-4-hydroxy-pyrrolidine derivatives and (R,R)—N-Boc-3-cyano-4-hydroxy-pyrrolidine derivatives (S,S)—N-Boc-3-cyano-4-hydroxy-pyrrolidine derivatives of formula (X) and (R,R)—N-Boc-3-cyano-4-hydroxy-pyrrolidine derivatives of formula (XI) are used as an intermediates to prepare the compounds of formula (I).

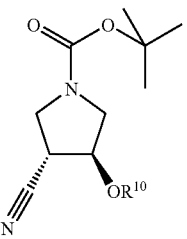

X

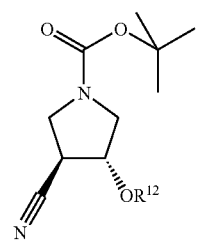

XI

In formula (X), $R^{10}$ is hydrogen or an acyl group of formula —$COR^{11}$ in which $R^{11}$ is $C_{1-5}$ alkyl or substituted $C_{1-3}$ alkyl. The term "$C_{1-5}$ alkyl" as used for $R^{11}$ denotes a branched or straight chain monovalent alkyl radical, having one to five carbon atoms, such as methyl, ethyl, n-propyl, n-butyl, isobutyl, n-pentyl and isopentyl. Particular $C_{1-5}$ alkyls are methyl, ethyl or n-propyl. The term "substituted $C_{1-3}$ alkyl" as used for $R^{1d}$ denotes a straight chain monovalent alkyl radical, having one to three carbon atoms substituted by one or more substituents selected from the group consisting of hydroxy, $C_{1-6}$ alkoxy and halogen, such as chloromethyl and methoxymethyl.

In formula (XI), $R^{12}$ is hydrogen or an acyl group of formula $COR^{13}$ in which $R^{13}$ is $C_{1-5}$ alkyl. The term "$C_{1-5}$ alkyl" as used for $R^{13}$ denotes a branched or straight-chain monovalent alkyl radical, having one to five carbon atoms, such as methyl, ethyl, n-propyl, n-butyl, isobutyl, n-pentyl and isopentyl. Particular $C_{1-5}$ alkyls are methyl, ethyl or n-propyl.

These intermediates can be prepared through chemoenzymatic procedures based on kinetic racemic resolution described below.

As no enzyme was found which simultaneously generated both, the (R,R)- and the (S,S)-configurated enantiomer in high enantiomeric excess (>95% ee) in one kinetic racemic resolution process, the two antipodes had to be produced in two separate processes, each as the retained enantiomer.

The two enzymatic processes are the following:

1. Enantioselective enzymatic acylation of trans-racemic N-Boc-3-cyano-4-hydroxy-pyrrolidine in anhydrous organic solvent using an enol ester as the acyl donor as outlined in Scheme I.

Scheme I

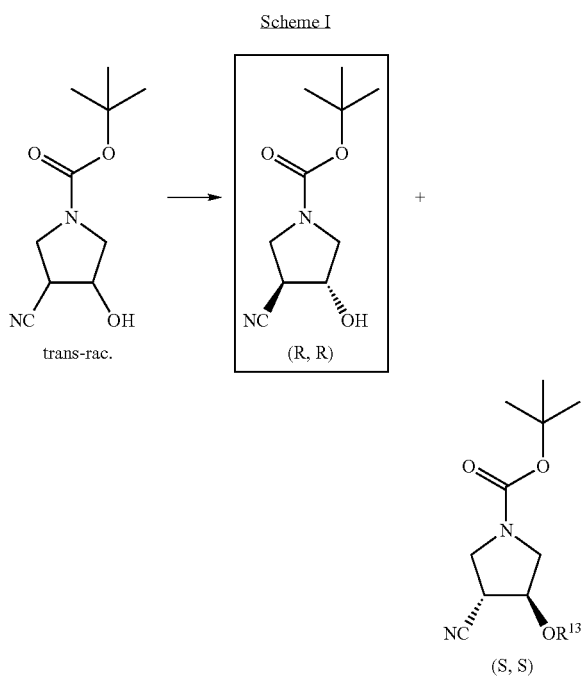

wherein R[13] has the meaning described before; and
2. enantioselective hydrolysis of trans-racemic N-Boc-3-cyano-4-acyloxy-pyrrolidine in an aqueous buffer according to Scheme II Scheme II

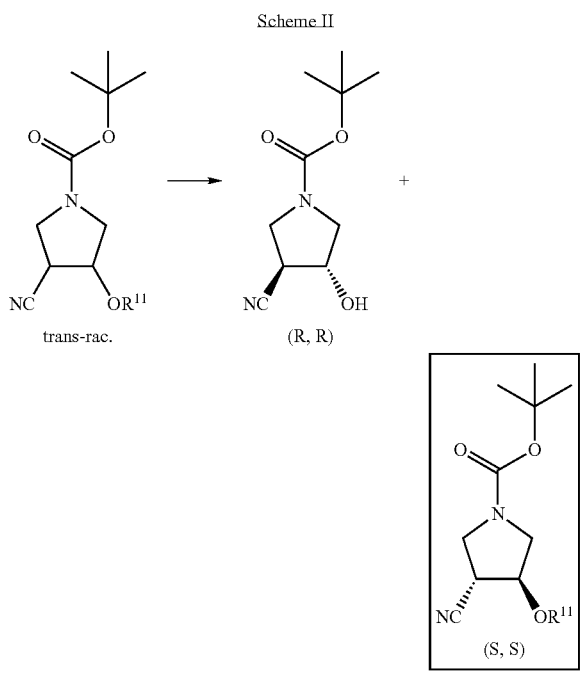

wherein R[11] has the meaning described before.

Acylation of the trans-racemic alcohol substrate by conventional chemical methods leads to the trans-racemic acyloxy substrate for the enantioselective enzymatic hydrolysis (Scheme II).

The enantioselective enzymatic acylation (Scheme I) is carried out by contacting a nearly anhydrous enzyme preparation with the alcohol substrate dissolved in an organic solvent containing an acyl donor. The reaction mixture is stirred until the retained alcohol has reached a high enantiomeric excess (>50% conversion). Suitable enzymes are lipases, preferentially lipases from *Pseudomonas*, more preferentially lipases from *Pseudomonas fluorescens*, a particular representant of which is commercially available Lipase AK from Amano Enzymes Inc. (Japan). Suitable acyl donors are commercially available activated esters such as enolesters, preferentially vinyl acylates. Suitable organic solvents are ethers (e.g. TBME, iPr$_2$O) or esters (e.g. EtOAc), optionally also mixtures of solvents may be used. Acyl donor and solvent can be used at a wide ratio. The water content of the system is less than 1% (v/v). After termination of the reaction, the reaction products are worked up conventionally by filtering off the suspended enzyme, evaporating the filtrate and separating the products by chromatography or liquid-liquid-countercurrent extraction.

The retained, enantiomerically pure (R,R)-alcohol may be derivatized with a conventional alcohol protecting group according to the usual synthetic procedures. Preferably, the protecting group is an acyl group to generate compounds of formula XI containing an acyl group of formula —COR$^{13}$ with R$^{13}$ as defined above.

The enantioselective hydrolysis (Scheme II) is carried out by contacting an enzyme with enantiomerically enriched (obtained above) or, alternatively, racemic acyloxysubstrate emulsified in an aqueous buffer by vigorous stirring until the retained acylate has reached a high enantiomeric excess (>50% conversion). Suitable enzymes are lipases from *Candida antarctica* (form B), *Candida cylindracea* (reclassified as rugosa), *Pseudomonas fluorescens* or proteases from *Aspergillus sojae*, preferentially lipase from *Candida antarctica* (form B) particular representants of which are commercially available Lipozyme CALB L from Novozymes (Denmark) or Chirazyme L-2 from Roche Applied Sciences (Germany). Suitable buffers are the conventional buffers commonly used in biochemistry in the range of pH 5-9, preferably 7-8. The pH of the reaction mixture is kept constant in the course of the reaction by the addition of a base, preferentially NaOH or KOH-solution. Optionally, the substrate may be dissolved in an organic solvent, preferentially a water-immiscible one. A lower temperature (<20° C.) might be used to enhance the enzyme selectivity. As an alternative, the enzymes may be used in immobilized form. After termination of the reaction (i.e. retained acetate with >98% ee), the reaction products are worked up conventionally by extraction and separated from each other by chromatography or liquid-liquid-countercurrent extraction.

Subsequently, the retained, enantiomerically pure (S,S)-acylate may be hydrolyzed by the usual procedures to generate a compound of formula (X) with hydrogen as R$^{10}$.

10.2. Synthesis of 4-alkoxy-3-aminomethylpyrrolidines

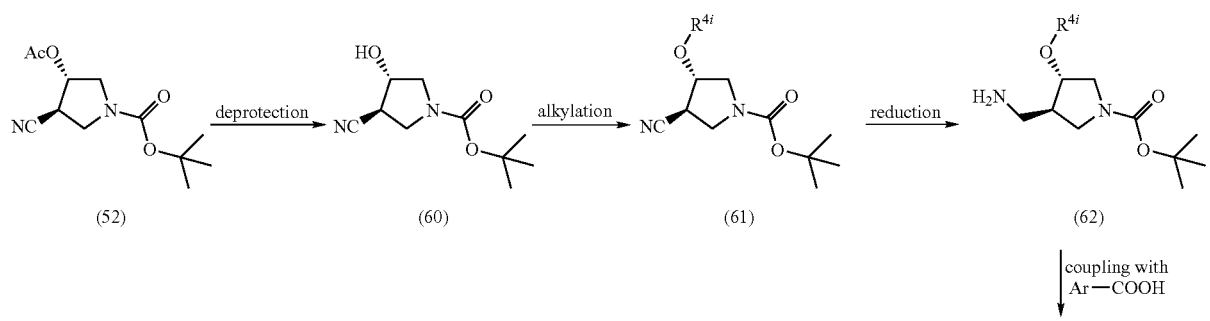

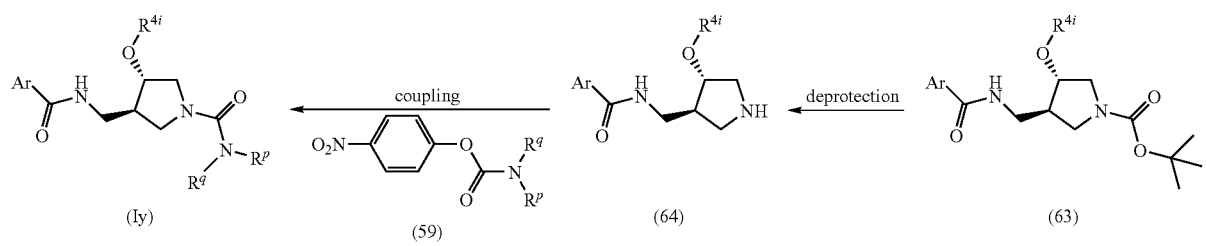

Ar in the scheme is $Y^3$—$Y^2$ as defined before. $R^p$ in the scheme is hydrogen and $R^q$ in the scheme is —$X^2$—$X^3$ as defined before. $R^{4i}$ in the scheme is $C_{1-6}$ alkyl, halo $C_{1-6}$ alkyl or —$C_{1-6}$ alkyl-OH.

Intermediate (60): Intermediate (52) is deprotected according to the procedure for the preparation of intermediate (57).

Intermediate (61): Intermediate (60) is alkylated with an appropriate alkyl halide either by promoting the reaction with $Ag(I)_2O$ in a solvent such as toluene, THF or acetonitrile. Elevated temperatures up the boiling point of the respective solvents, multiple additions of alkyl halide and prolonged reaction times up to 6 days were required in order to drive the reaction to completion.

Intermediate (62): Intermediate (61) is reduced according to the procedure for the preparation of intermediate (55).

Intermediate (63): Intermediate (62) is reacted with a carboxylic acid Ar—COOH according to the procedure for the preparation of intermediate (49).

Intermediate (64): Intermediate (63) is deprotected according to the procedure for the preparation of intermediate (50).

Final product (Iy): Intermediate (64) is coupled with intermediate (51) according to the procedure for the preparation of final product (Iu).

10.3. Syntheses via 4-keto intermediate

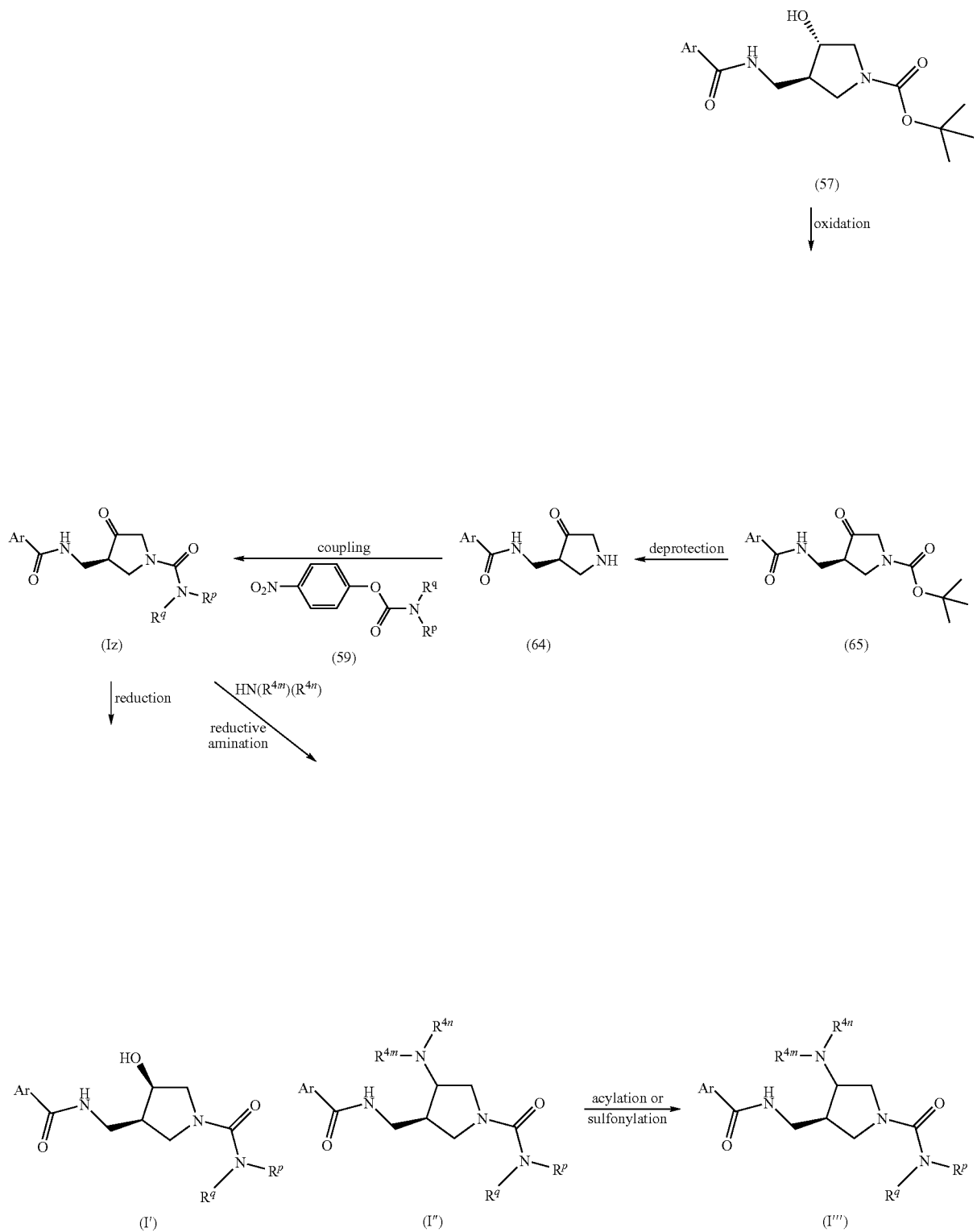

Ar in the scheme is Y³—Y² as defined before. R^p in the scheme is hydrogen and R^q in the scheme is —X²—X³ as defined before. (R^{4m})(R^{4n})N— is di-$C_{1-6}$ alkyl substituted amino, di-halo$C_{1-6}$ alkyl substituted amino, ($C_{1-6}$ alkylcarbonyl)($C_{1-6}$ alkyl)amino-, ($C_{1-6}$ alkoxycarbonyl)($C_{1-6}$ alkyl) amino-, ($C_{1-6}$ alkylsulfonyl)($C_{1-6}$ alkyl)amino-, mono-$C_{1-6}$ alkyl substituted amino, mono-halo$C_{1-6}$ alkyl substituted amino, $C_{1-6}$ alkyl-sulfonylamino- or $C_{1-6}$ alkyl-carbonylamino-.

Final product (I'''): Final product (I'') is acylated or sulfonylated in the presence of a chloroformate or a sulfochloride and a base, e.g. $NEt_3$ or N,N-diisopropylethylamine in a solvent such as e.g. THF, $CH_2Cl_2$ or $CH_3CN$ at −10 to 60° C., e.g. at 20° C. for 1-40 h. The products obtained consist of a mixture of epimers at the N(R^{4m})(R^{4n}) stereo center.

11. Synthesis of alkyl- and aryl-substituted aminopyrrolidine derivatives

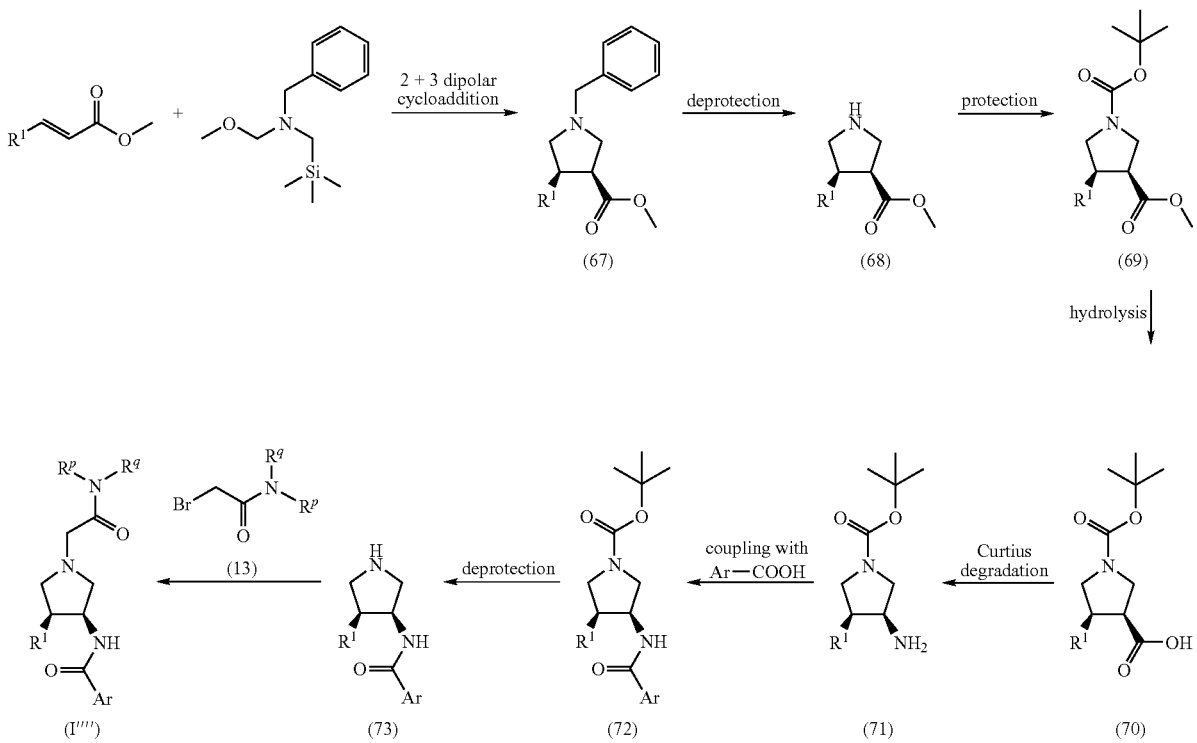

Intermediate (65): Intermediate (57) is oxidized using the Parikh-Doering procedure (sulfurtrioxide-pyridine complex, TEA, DMSO/methylene chloride). The reaction proceeds at 0° C.—r.t. for 2-18 hrs under an argon atmosphere.

Intermediate (66): Intermediate (65) is deprotected according to the procedure for the preparation of intermediate (50).

Final product (Iz): Intermediate (66) is coupled with intermediate (59) according to the procedure for the preparation of final product (Iu).

Final product (I'): Final product (Iz) is reduced with a hydride reagent such as e.g. Li(CN)BH₃, Na(CN)BH₃, or LiBH₄ or NaBH₄ in a solvent such as e.g. MeOH or THF at a temperature of −10 to 60° C., in particular at 20° C. for 1-40 h.

Final product (I''): Final product (I') is reductively aminated in the presence of an amine and a reducing agent such as e.g. NaBH₄, LiBH₄, Li(CN)BH₃ or Na(CN)BH₃ in a solvent such as an alcohol, e.g. MeOH or an ether, e.g. THF and an acid e.g. HCl, $H_2SO_4$, $H_3PO_4$ or a carboxylic acid, preferably $CH_3COOH$ at a temperature of −10 to 60° C., e.g. at 20° C. for 1-40 h. The products obtained consist of a mixture of epimers at the newly formed stereo center.

R¹' is as defined before. Ar in the scheme is Y³—Y²— as defined before. R^p in the scheme is hydrogen and R^q in the scheme is —X²—X³ as defined before.

Intermediate (67): An appropriately substituted α,β-unsaturated ester is reacted with the N-benzyl azomethine ylide (1,3-dipole) generated from either N-benzyl-N-(methoxymethyl)trimethyl-silylmethylamine at 0° C. in the presence of TFA and dichloromethane as solvent or from N-benzyl-trimethylsilanylmethylamine and aqueous formaldehyde at r.t. in the presence of TFA and THF as solvent or from N-benzylglycine and paraformaldehyde in toluene at elevated temperature as described in R. M. Rodriguez Sarmiento, B. Wirz, H. Iding *Tetrahedron Asymmetry* 2003, 14, 1547-1551.

Intermediate (68): Intermediate (67) is deprotected with hydrogen under normal pressure or by transfer hydrogenation with a catalyst such as $PtO_2$, Pd—C or Raney nickel in solvents such as MeOH, EtOH, $H_2O$, dioxane, THF, HOAc or mixtures thereof. Particular conditions are hydrogenation with Pd—C in EtOH as solvent.

Intermediate (69): the pyrrolidine intermediate (68) is protected using $Boc_2O$ in THF, dichloromethane, DMF or acetonitrile as solvent. A catalyst such as DMAP can be added.

Intermediate (70): Intermediate (69) is hydrolyzed as described in the preparation of intermediate (5).

Intermediate (71): The starting carboxylic acid is reacted with a diazo-transfer reagent such as diphenylphosphoryl azide, sodium azide, 4-acetamidobenzene sulfonyl azide, p-toluene sulfonyl azide in an organic solvent such as toluene, acetonitrile, DMF, DMA, NMP, DMSO at elevated temperature between 50-120° C. Particular conditions are diphenylphosphoryl azide in toluene at 80° C. The intermediate isocyanate can be converted either to the corresponding amine by quenching with KOH solution or be converted to the benzylcarbamate by addition of benzylalcohol. The benzylcarbamate is subsequently cleaved by hydrogenation under normal pressure or by transfer hydrogenation with a catalyst such as $PtO_2$, Pd—C or Raney nickel in solvents such as MeOH, EtOH, $H_2O$, dioxane, THF, HOAc or mixtures thereof. Particular conditions are hydrogenation with Pd—C in MeOH as solvent.

Intermediate (72): Intermediate (71) is reacted with a carboxylic acid Ar—COOH as described in the preparation of intermediate (4).

Intermediate (73): Intermediate (72) is deprotected as described in the preparation of intermediate (2).

Final product (I''''): Intermediate (73) is alkylated with intermediate (13) as described in the preparation of intermediate (1).

As described above, the compounds of formula (I) are active compounds and inhibit coagulation factor Xa. These compounds consequently influence both platelet activation which is induced by this factor and plasmatic blood coagulation. They therefore inhibit the formation of thrombi and can be used for the treatment and/or prevention of thrombotic disorders, such as, amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. The compounds of the present invention can also be used in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. Factor Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases.

They can therefore also be used as antitumor agents.

Prevention and/or treatment of thrombotic disorders, particularly arterial or deep vein thrombosis, is a particular indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of diseases which are associated with coagulation factor Xa, particularly as therapeutically active substances for the treatment and/or prophylaxis of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumor.

In another particular embodiment, the invention relates to a method for the therapeutic and/or prophylactic treatment of diseases which are associated with coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumor, which method comprises administering an effective amount of a compound as defined above to a human being or animal.

The invention also relates to the processes and the intermediates for manufacturing the compounds of formula (I) as well as the process for manufacturing the intermediates.

The inhibition of the coagulation factor Xa by the compounds of the present invention can be demonstrated with the aid of a chromogenic peptide substrate assay as described hereinafter. Factor Xa activity was measured spectrophotometrically in microtiter plates in a final volume of 150 µl using the following conditions: Inhibition of human factor Xa (Enzyme Research Laboratories) was tested at an enzyme concentration of 3 nM using the chromogenic substrate S-2222 (Chromogenix AB, Molndal, Sweden) at 200 nM. The reaction kinetics of the enzyme and the substrate were linear with both time and the enzyme concentration. The inhibitors were dissolved in DMSO and tested at various concentrations up to 100 µM. The inhibitors were diluted using HNPT buffer consisting of HEPES 100 mM, NaCl 140 mM, PEG 6000 0.1% and Tween 80 0.02%, pH 7.8. The cleavage of S-2222 by human factor Xa was followed at 405 nm for 5 minutes at room temperature. The velocity of the reaction was determined by the autoreader from the slope of the linear regression fit to 7 time points (1 minute). The initial velocity for each inhibitor concentration was determined by the slope of at least 4 time points in the linear phase by a linear regression fit ($mOD/min^2$). Apparent dissociation constants $K_i$ were calculated according to Cheng and Prusoff [Cheng, Y. C.; Prusoff, W. H. Relationship between the inhibition constant ($K_i$) and the concentration of the inhibitor that causes 50 percent inhibition ($IC_{50}$) of an enzyme reaction. Biochem. Pharmacol. 1973, 22, 3099-3108.] based on the $IC_{50}$ and the respective $K_m$, determined previously ($K_i=IC_{50}/(1+S/K_m)$). The $K_m$ for the substrate used was determined under the conditions of the test with at least 5 substrate concentrations ranging from 0.5 to 15 times $K_m$. [Lottenberg R, Hall J A, Blinder M, Binder E P, Jackson C M., The action of thrombin on peptide p-nitroanilide substrates. Substrate selectivity and examination of hydrolysis under different reaction conditions. Biochim Biophys Acta. 1983 Feb. 15; 742(3):539-57]. According to Eadie [Eadie G. S. The inhibition of cholinesterase by physostigmine and prostigmine. J. Biol. Chem. 1942, 146, 85-93.], the $K_m$ for S-2222 amounted to 613 µM.

The activity of the low molecular weight substances can, moreover, be characterized in the "prothrombin time" (PT) clotting test. The substances are prepared as a 10 mM solution in DMSO and thereafter made up to the desired dilution in the same solvent. Thereafter, 0.25 ml of human plasma (obtained from whole blood anticoagulated with ¹/₁₀ volume of 108 mM Na citrate) was placed in the instrument-specific sample container. In each case 5 µl of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 µl of plasma/inhibitor mixture in the measurement container. The clotting reaction was initiated by the addition of 0.1 ml of Dade® Innovin® (recombinant human tissue factor combined with calcium buffer and synthetic phospholipids, Dade Behring, Inc., Cat. B4212-50). The time up to the fibrin cross-linking was determined photooptically from the ACL. The inhibitor concentration, which brought about a doubling of the PT clotting time, was determined by fitting the data to an exponential regression (XLfit).

The compounds of the present invention can furthermore be characterised by the Activated Partial Thromboplastin time (aPTT). This coagulation test can e.g. be run on the ACL 300 Coagulation System (Instrumentation Laboratory) automatic analyzer. The substances are prepared as a 10 mM solution in DMSO and thereafter made up to the desired dilution in the same solvent. The test is performed with the Dade® Actin® FS Activated PTT reagent (purified soy phosphatides in $1.0 \times 10^{-4}$M ellagic acid, stabilizers and preservative, Dade Behring, Inc., Cat. B4218-100). Thereafter, 0.25 ml aliquots of human plasma (obtained from whole blood anticoagulated with 1/10 volume of 108 mM Na citrate) are spiked with 5 µl of test compound in at least 6 concentrations. 50 µl plasma at 4° C. containing 1/50 vol. inhibitor in solvent are incubated with 50 µl Dade® Actin® FS Activated PTT reagent in water at 37° C. for 3 min., then 50 µl $CaCl_2.2H_2O$ 25 mM in water at 37° C. are added. The time up to the fibrin cross-linking was determined photooptically from the ACL. The inhibitor concentration, which brought about a doubling of the APTT clotting time, was determined by fitting the data to an exponential regression (XLfit).

The $K_i$ values of the active compounds of the present invention generally are about 0.001 to about 50 µM, especially about 0.001 to about 1 µM., The PT values generally are about 0.5 to about 100 µM, especially about 0.5 to about 10 µM. The aPTT values generally are about 0.5 to about 100 µM, especially about 0.5 to about 10 µM.

| Example | $K_i$ [µM] factor Xa |
| --- | --- |
| Example 6 | 0.017 |
| Example 26 | 0.014 |
| Example 54 | 0.013 |
| Example 77 | 0.008 |
| Example 85 | 0.012 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is one particular route of administration.

The production of the pharmaceutical preparations can be effected in a manner which would be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1 to about 500 mg, e.g., about 1 to about 100 mg, of a compound of formula (I).

The following Examples serve to illustrate the present invention in more detail. They are, however, not intended to limit its scope in any manner.

EXAMPLES

General Procedures

General Procedure A: Alkylation of Pyrrolidine Derivatives with an α-Bromoacetic Acid Derivative To a stirred mixture of the pyrrolidine (1 eq) in THF were added TEA (1.5-5 eq) and then the α-bromoacetic acid derivative (1.2-2 eq). A catalytic amount (up to 0.5 eq) tetrabutyl ammonium iodide may be added. The reaction mixture is agitated under an argon atmosphere for 2 hrs to 4 days at 0° C.-50° C. In case a precipitate has formed, it is filtered off and washed with THF. The filtrate is concentrated. The residue is taken up in EtOAc, washed with 0.01N NaOH, water and brine. The organic layer is dried over $MgSO_4$, filtrated and concentrated. The crude product can be purified by flash chromatography on silica gel or by crystallization.

General Procedure B: Cleavage of a Boc Protecting Group with HCl

To a solution of the starting Boc-protected amine (1 eq) in dioxane was added 4N HCl in dioxane (10-15 eq). The reaction mixture was stirred for 2-18 hrs at r.t., then concentrated. The crude product can be purified by flash chromatography on silica gel.

General Procedure C: Cleavage of a Boc Protecting Group with TFA

To a solution of the starting Boc-protected amine (1 mmol) in CH$_2$Cl$_2$ (1.5 ml) was added at 22-C CF$_3$COOH (10 mmol) and stirring was continued for 1-5 h. The solution was evaporated to dryness and used without further purification.

General Procedure D: Coupling of a Carboxylic Acid with an Amine Using BOP as a Coupling Reagent To a stirred solution of the acid (1 eq) in DMF or THF is added the amine (0.8-2 eq), N-ethyl-diisopropylamine (3-5 eq) and then BOP-reagent (1.1-1.5 eq). The mixture is stirred at r.t. under an argon atmosphere for 3-24 h. The mixture is diluted with EtOAc, washed with water and brine, dried (MgSO$_4$), filtered and concentrated. The crude product can be purified by chromatography (silicagel) or by crystallization.

General Procedure E: Coupling of an Amine with the Carboxylic Acid Using EDCI as a Coupling reagent To a solution of the starting Boc-protected amine (1 mmol) in THF (3.5 ml) was subsequently added HOBT (1.5 mmol), EDCI (1.5 mmol) and NEt$_3$ (4.5 mmol) and stirring was continued at 22° C. for 1.5 h. The suspension was treated with the acid (1.1 mmol) and stirring was continued at 60° C. for 16 h. The mixture was evaporated and the residue partitioned between AcOEt and 0.1 N NaOH. The organic layer was washed with 1 N HCl, dried and evaporated to give the crude product which can be used without purification or optionally purified by flash chromatography on silica gel.

General Procedure F: Conversion of a Carboxylic Acid Ester to an Aryl Amide Using AlMe$_3$ Activation The starting aniline (1.2-4 eq) was dissolved in toluene or dioxane to give a 5-10% solution which was treated under an argon atmosphere at r.t. with AlMe$_3$ in heptane or toluene (1.2-4 eq). The reaction mixture was stirred at r.t. for 90 min. Then the ester (1 eq) was added. The temperature was raised to 90° C.-110° C. Stirring was continued for 3-20 hrs. The reaction mixture was cooled to r.t., then treated with H$_2$O (ca. 20-50 eq). After stirring for 10 min the mixture was treated with Na$_2$SO$_4$. After stirring for 15 min, the mixture was filtered (if necessary over Celite). The filtrate was concentrated. The product was be purified by crystallization of by chromatography (silicagel).

General Procedure G: Activating of an Amine with 4-Nitrophenyl Chloroformate

To a stirred suspension of the amine (1 mmol) in 3 ml of CH$_2$Cl$_2$, 0,33 ml of DMF and pyridine (1 mmol) was added at 0° C. 4-nitrophenyl chloroformate (1 mmol) and stirring was continued at 0° C. for 1 h and at 22° C. for 16 h. The suspension was filtered, the residue containing the 4-nitrophenylcarbamate was washed with water (20 ml) and CH$_2$Cl$_2$ (10 ml) and dried at 0.1 mbar.

General Procedure H: Coupling of an Amine with a 4-Nitrophenylcarbamate

To a stirred solution of the amine (1 mmol) in DMF (7.5 ml) was added the 4-nitrophenylcarbamate (1 mmol) and N-ethyl-diisopropylamine (3 mmol) and the mixture was heated to 80° C. for 1-5 h. The mixture was partitioned between AcOEt and aqueous Na$_2$CO$_3$, the organic layer was washed with brine, dried and evaporated. The crude material was purified on preparative HPLC (RP-18) using a gradient of CH$_3$CN/H$_2$O (containing 0.1% of HCOOH) (20:80 to 95:5).

Example 1 (Reference)

1.1 Using general procedure A, (R)-(+)-3-(tert-butyloxy-carbonylamino)-pyrrolidine was alkylated with bromoacetic acid ethyl ester to give ((R)-3-tert-butoxycarbonylamino-pyrrolidin-1-yl)-acetic acid ethyl ester. Off-white solid. MS 273.1 ([M+H]$^+$)

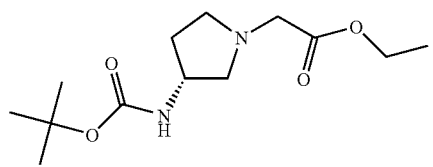

1.2 Using general procedure B, ((R)-3-tert-butoxycarbonylamino-pyrrolidin-1-yl)-acetic acid ethyl ester was converted to ((R)-3-amino-pyrrolidin-1-yl)-acetic acid ethyl ester dihydrochloride. Off-white amorphous solid. MS 173.4 ([M+H]$^+$)

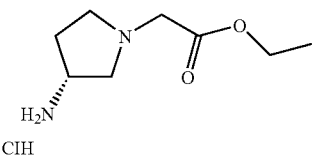

1.3 Using general method D, ((R)-3-amino-pyrrolidin-1-yl)-acetic acid ethyl ester dihydrochloride was coupled with 5-chlorothiophene-2-carboxylic acid to give {(R)-3-[(5-chloro-thiophene-2-carbonyl)-amino]-pyrrolidin-1-yl}-acetic acid ethyl ester. Off-white amorphous solid. MS 317.0 ([M+H]$^+$)

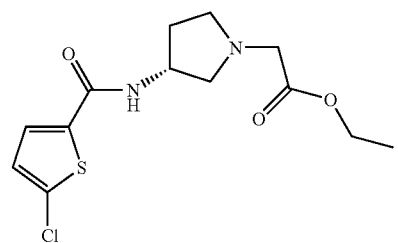

1.4 Using general method F, {(R)-3-[(5-chloro-thiophene-2-carbonyl)-amino]-pyrrolidin-1-yl}-acetic acid ethyl ester was reacted with 1-(4-amino-3-fluoro-phenyl)-1H-pyridin-2-one (CAS 536747-52-1, prepared according to WO 2003045912) to give 5-chloro-thiophene-2-carboxylic acid ((R)-1-{[2-fluoro-4-(2-oxo-2H-pyridin-1-yl)-phenylcarbamoyl]-methyl}-pyrrolidin-3-yl)-amide. Off-white amorphous solid. Light yellow solid. MS 475.3 ([M+H]$^+$)

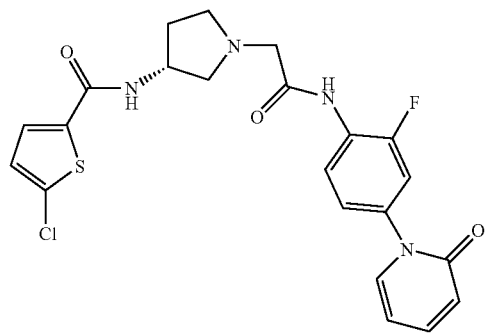

Example 2 (Reference)

A solution of 200 mg {(R)-3-[(5-chloro-thiophene-2-carbonyl)-amino]-pyrrolidin-1-yl}-acetic acid ethyl ester (Ex. 1.3) in 4 ml EtOH and 4 ml H$_2$O was treated with 0.051 g NaOH. The reaction mixture was stirred for 4 hrs at r.t., then evaporated. The resulting crude acid was coupled with 1-(N-methylpiperidin-4-yl)piperazine according to general method D to give 5-chloro-thiophene-2-carboxylic acid ((R)-1-{2-[4-(1-methyl-piperidin-4-yl)-piperazin-1-yl]-2-oxo-ethyl}-pyrrolidin-3-yl)-amide. Light yellow solid. MS 454.6 ([M+H]$^+$)

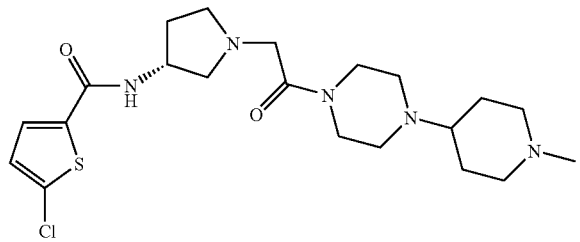

Example 3 (Reference)

In analogy to example 1, [(S)-3-(tert-butyloxycarbonylamino)-pyrrolidine was converted to 5-chloro-thiophene-2-carboxylic acid ((S)-1-{[2-fluoro-4-(2-oxo-2H-pyridin-1-yl)-phenylcarbamoyl]-methyl}-pyrrolidin-3-yl)-amide. Off-white amorphous solid. MS 475.3 ([M+H]$^+$)

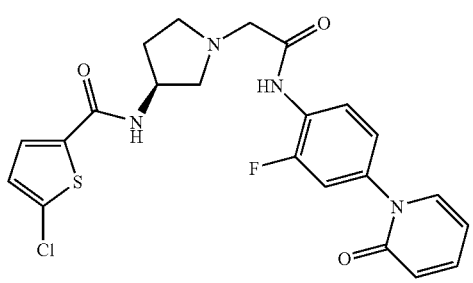

Example 4 (Reference)

In analogy to example 1.1, 1.2 and 2, [[(S)-3-(tert-butyloxycarbonylamino)-pyrrolidine was converted to 5-chloro-thiophene-2-carboxylic acid ((S)-1-{2-[4-(1-methyl-piperidin-4-yl)-piperazin-1-yl]-2-oxo-ethyl}-pyrrolidin-3-yl)-amide. White solid. MS 454.6 ([M+H]$^+$)

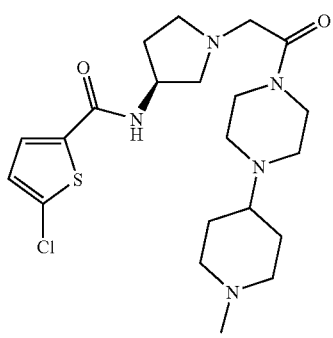

Example 5 (Reference)

5.1 Using general procedure D ((R)-3-amino-pyrrolidin-1-yl)-acetic acid ethyl ester dihydrochloride (example 1.2) was coupled with 4-chlorobenzoic acid to give [(R)-3-(4-chloro-benzoylamino)-pyrrolidin-1-yl]-acetic acid ethyl ester. Solid. MS 311.3 ([M+H]$^+$)<

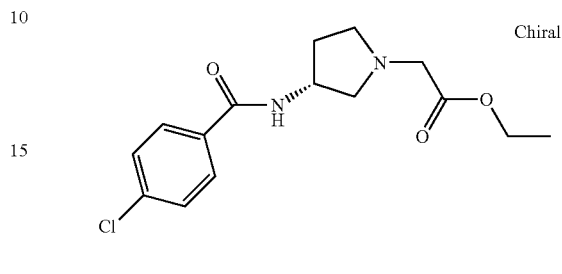

5.2 Using general procedure F [(R)-3-(4-chloro-benzoylamino)-pyrrolidin-1-yl]-acetic acid ethyl ester was reacted with 1-(4-amino-3-fluoro-phenyl)-1H-pyridin-2-one (CAS 536747-52-1, prepared according to WO 2003045912) to give 4-chloro-((R)-1-{[2-fluoro-4-(2-oxo-2-pyridin-1-yl)-phenylcarbamoyl]-methyl}-pyrrolidin-3-yl)-benzamide. Light yellow solid. MS 469.5 ([M+H]$^+$)

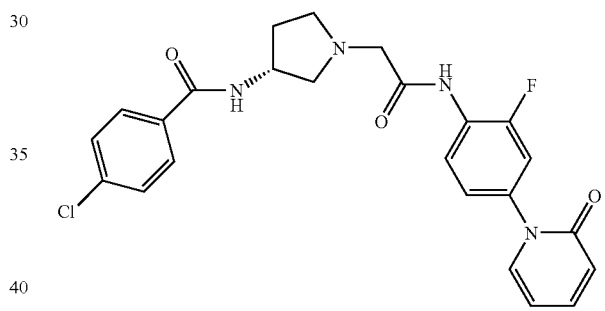

Example 6 (Reference)

6.1 Using general procedure D (R)-1-Boc-3-aminopyrrolidine was coupled with 5-chlorothiophene-2-carboxylic acid to give (R)-3-[(5-chloro-thiophene-2-carbonyl)-amino]-pyrrolidine-1-carboxylic acid tert-butyl ester. Yellow solid. MS 329.3 ([M−H]$^−$)

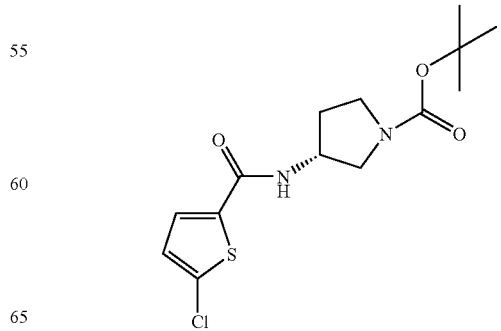

6.2 Using general procedure B (R)-3-[(5-chloro-thiophene-2-carbonyl)-amino]-pyrrolidine-1-carboxylic acid tert-butyl ester was deprotected to give 5-chloro-thiophene-2-carboxylic acid (R)-pyrrolidin-3-ylamide hydrochloride. Yellow solid. MS 231.4 ([M+H]$^+$)

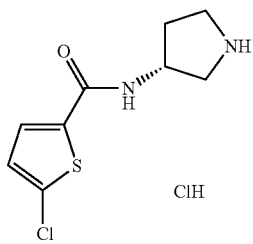

6.3 Using general procedure A 5-chloro-thiophene-2-carboxylic acid (R)-pyrrolidin-3-ylamide hydrochloride was reacted with ethyl-2-bromopropionate to give 2-{(R)-3-[(5-chloro-thiophene-2-carbonyl)-amino]-pyrrolidin-1-yl}-propionic acid ethyl ester. Oil. MS 329.1 ([M−H]$^−$)

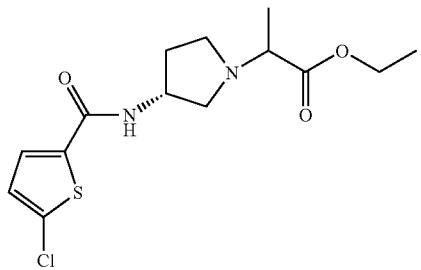

6.4 Using general procedure F 2-{(R)-3-[(5-chloro-thiophene-2-carbonyl)-amino]-pyrrolidin-1-yl}-propionic acid ethyl ester was reacted with 1-(4-amino-3-fluoro-phenyl)-1H-pyridin-2-one (CAS 536747-52-1, prepared according to WO 2003045912) to give 5-chloro-thiophene-2-carboxylic acid ((R)-1-{1-[2-fluoro-4-(2-oxo-pyridin-1-yl)-phenylcarbamoyl]-ethyl}-pyrrolidin-3-yl)-amide. Yellow solid. MS 487.4 ([M−H]$^−$)

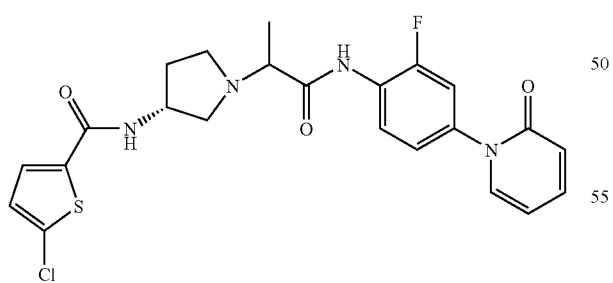

Example 7 (Reference)

7.1 A solution of 400 mg 5-chloro-thiophene-2-carboxylic acid (R)-pyrrolidin-3-ylamide hydrochloride (example 6.2) in 5 ml THF was treated with 0.31 ml TEA and 0.16 ml bromo acetylbromide. The reaction mixture was stirred over night. The precipitate was filtered and washed with THF. The filtrate was concentrated. The crude product was purified by chromatography (silica gel; gradient: CH$_2$Cl$_2$ to CH$_2$Cl$_2$/MeOH 98:2) to give 250 mg 5-chloro-thiophene-2-carboxylic acid [(R)-1-(2-bromo-acetyl)-pyrrolidin-3-yl]-amide. Off-white amorphous solid. 353.1 ([M+H]$^+$)

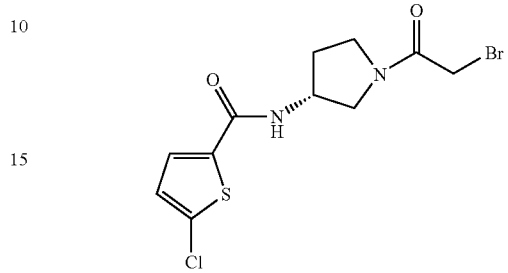

7.2 A solution of 250 mg 5-chloro-thiophene-2-carboxylic acid [(R)-1-(2-bromo-acetyl)-pyrrolidin-3-yl]-amide in 2 ml DMF was treated with 110 mg 1-(4-amino-phenyl)-1H-pyridin-2-one (CAS 13143-47-0), 0.12 ml TEA and 110 mg tetrabutylammonium iodide. The reaction mixture was stirred at r.t. for 2 days, then quenched with water and extracted with EtOAc. The organic layer was washed with water, dried over MgSO$_4$ and filtrated. The crude product was purified by chromatography (silica gel; gradient: CH$_2$Cl$_2$ to CH$_2$Cl$_2$/MeOH 95:5) to give 72 mg 5-chloro-thiophene-2-carboxylic acid ((R)-1-{2-[4-(2-oxo-pyridin-1-yl)-phenylamino]-acetyl}-pyrrolidin-3-yl)-amide. MS 457.5 ([M+H]$^+$)

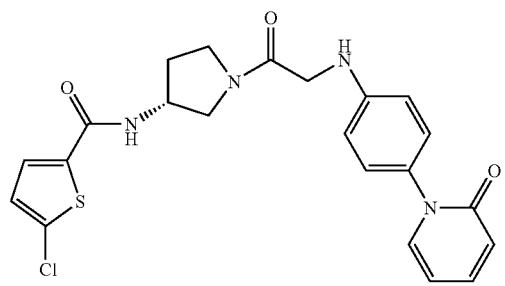

Example 8 (Reference)

8.1 A suspension of 540 mg ((R)-3-amino-pyrrolidin-1-yl)-acetic acid ethyl ester dihydrochloride (example 1.2) in 5 ml THF was treated with 1.2 ml TEA and 530 mg 5-chlorothiophene-2-sulfonylchloride. The reaction mixture was stirred over night at r.t., then taken up in EtOAc and washed with water and brine. The organic layer was dried over MgSO4, filtered and concentrated to give 690 mg [(R)-3-(5-chloro-thiophene-2-sulfonylamino)-pyrrolidin-1-yl]-acetic acid ethyl ester. Oil. 353.1 ([M+H]$^+$)

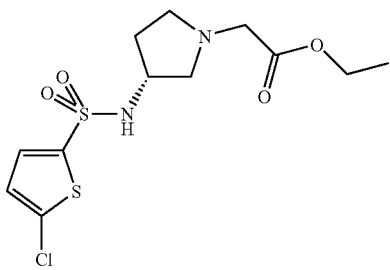

8.2 Using general procedure F [(R)-3-(5-chloro-thiophene-2-sulfonylamino)-pyrrolidin-1-yl]-acetic acid ethyl ester was reacted with 1-(4-amino-3-fluoro-phenyl)-1H-pyridin-2-one (CAS 536747-52-1, prepared according to WO 2003045912) to give 2-[(R)-3-(5-chloro-thiophene-2-sulfonylamino)-pyrrolidin-1-yl]-N-[2-fluoro-4-(2-oxo-2H-pyridin-1-yl)-phenyl]-acetamide. White solid. MS 511.3 ([M+H]$^+$)

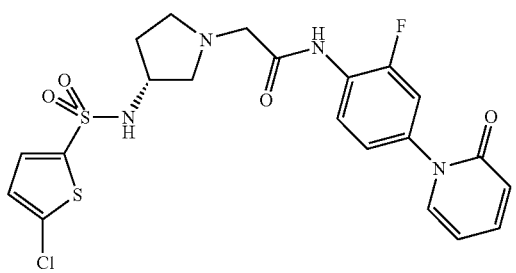

Example 9 (Reference)

9.1 In analogy to examples 1.1-1.3 3-N-Boc-amino-piperidine was converted to {3-[(5-chloro-thiophene-2-carbonyl)-amino]-piperidin-1-yl}-acetic acid ethyl ester. Solid. 331.3 ([M+H]$^+$)

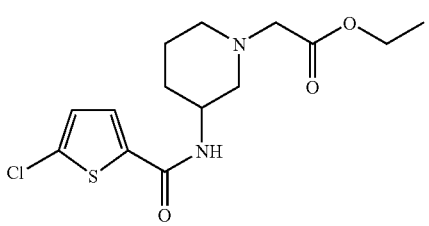

9.2 To a stirred solution of {3-[(5-chloro-thiophene-2-carbonyl)-amino]-piperidin-1-yl}-acetic acid ethyl ester at r.t. in 5 ml ethanol were added 5 ml 1 N NaOH. The slurry slowly turned to a clear solution. Stirring at r.t. was then continued for 5 h. The mixture was neutralized by adding 5 ml of 1 N HCl (pH ~7). The light orange solution was concentrated to leave an off-white solid. This residue was coevaporated several times with toluene to remove the remaining H$_2$O, and dried overnight (r.t., 0.5 mbar) to give 1.07 g {3-[(5-chloro-thiophene-2-carbonyl)-amino]-piperidin-1-yl}-acetic acid (containing 2 mol equivalents of sodium chloride). Off-white solid. MS 301.3 ([M−H]$^−$)

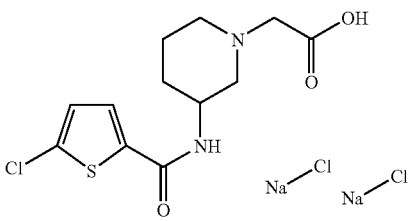

9.3 To a stirred suspension of 300 mg {3-[(5-chloro-thiophene-2-carbonyl)-amino]-piperidin-1-yl}-acetic acid (containing 2 mol equivalents of sodium chloride) at r.t. in 5 ml acetonitrile and 0.5 ml DMF under an argon atmosphere were added 0.5 ml N-ethyldiisopropylamine, 175 mg 1-(4-amino-3-fluoro-phenyl)-1H-pyridin-2-one (CAS 536747-52-1, prepared according to WO 2003045912) and 365 mg BOP-Cl. The compact slurry was then stirred at r.t. for 18 h. The mixture was concentrated. The residue was taken up with CH$_2$Cl$_2$, washed with 1 N NaOH, H$_2$O and brine, dried (MgSO$_4$), filtered and concentrated. The crude product was purified by chromatography (silica gel; gradient: cyclohexane to EtOAc) to give 98 mg 5-chloro-thiophene-2-carboxylic acid (1-{[2-fluoro-4-(2-oxo-2H-pyridin-1-yl)-phenylcarbamoyl]-methyl}-piperidin-3-yl)-amide. White solid. MS 489.5 ([M+H]$^+$)

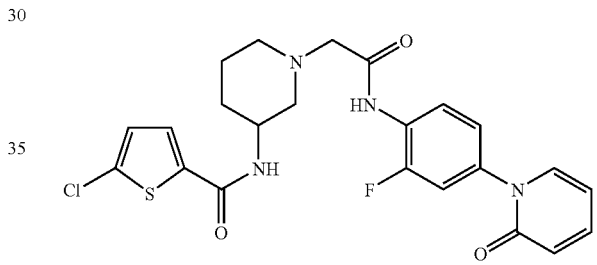

Example 10 (Reference)

Using general procedure D {3-[(5-chloro-thiophene-2-carbonyl)-amino]-piperidin-1-yl}-acetic acid (containing 2 mol equivalents of sodium chloride) was coupled with 1-(N-methyl-4-piperidyl)-piperazine to give 5-chloro-thiophene-2-carboxylic acid (1-{2-[4-(1-methyl-piperidin-4-yl)-piperazin-1-yl]-2-oxo-ethyl}-piperidin-3-yl)-amide. Off-white solid. 468.5 ([M+H]$^+$)

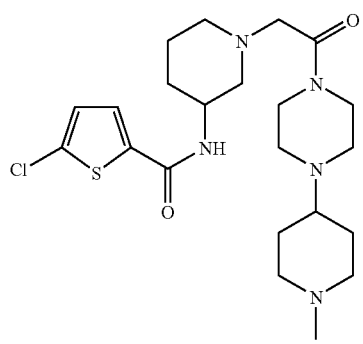

Example 11

11.1 Using general procedure D N-Boc-trans-4-amino-L-proline methyl ester hydrochloride was coupled with 5-chlorothiophene-2-carboxylic acid to give (2S,4R)-4-[(5-chlorothiophene-2-carbonyl)-amino]-pyrrolidine-1,2-dicarboxylic acid 1-tert-butyl ester 2-methyl ester. White solid. MS 389.4 ([M+H]$^+$)

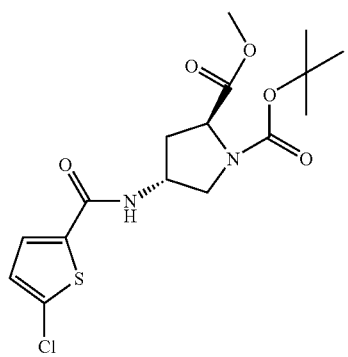

11.2 Using general procedure B (2S,4R)-4-[(5-chlorothiophene-2-carbonyl)-amino]-pyrrolidine-1,2-dicarboxylic acid 1-tert-butyl ester 2-methyl ester was deprotected to give (2S,4R)-4-[(5-chloro-thiophene-2-carbonyl)-amino]-pyrrolidine-2-carboxylic acid methyl ester hydrochloride. White solid. MS 289.0 ([M+H]$^+$)

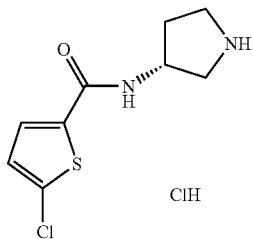

11.3 A solution of 3 g 1-(4-amino-3-fluoro-phenyl)-1H-pyridin-2-one (CAS 536747-52-1, prepared according to WO 2003045912) in 90 ml THF was treated with 3.5 ml TEA and 2.3 ml bromoacetyl bromide. The suspension was stirred over night at r.t., then concentrated. The residue was taken up in CH$_2$Cl$_2$ and was washed with 1 N HCl and brine, dried (MgSO$_4$), filtered and concentrated. The crude product was purified by chromatography (silica gel; gradient: CH$_2$Cl$_2$-> CH$_2$Cl$_2$/MeOH 9:1). The product-containing fractions were concentrated. The remaining solid was triturated with diethyl ether to give 3.1 g 2-bromo-[2-fluoro-4-(2-oxo-pyridin-1-yl)-phenyl]-acetamide as off-white solid. MS 325.0 ([M+H]$^+$)

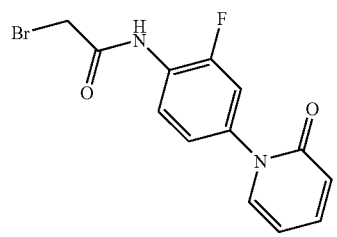

11.4 Using general procedure A with DMF as solvent (2S,4R)-4-[(5-chloro-thiophene-2-carbonyl)-amino]-pyrrolidine-2-carboxylic acid methyl ester hydrochloride was reacted with 2-bromo-[2-fluoro-4-(2-oxo-pyridin-1-yl)-phenyl]-acetamide to give (2S,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid methyl ester. White solid. MS 533.2 ([M+H]$^+$)

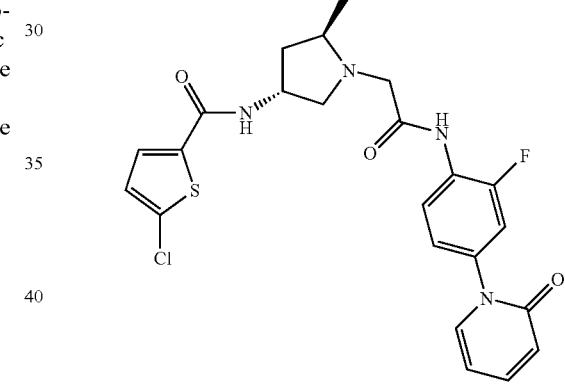

Example 12

A solution of 394 mg (2S,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid methyl ester (example 11.4) in 10 ml THF was treated with 1.5 ml 1N NaOH. The reaction mixture was stirred for 4 hrs at r.t., then brought to pH 7 with 3N HCl and concentrated. The crude product was purified by chromatography (silica gel; CH$_2$Cl$_2$/MeOH 4:1, then MeOH). The product-containing fractions were concentrated, triturated with water and dried to give 290 mg (2S,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid as an off-white solid. MS 519.3 ([M+H]$^+$)

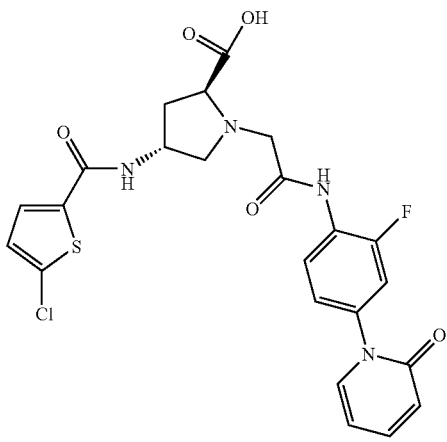

Example 13

Using general procedure D (2S,4R)-4-[(5-chloro-thiophene-2-carbonyl)-amino]—1-{[2-fluoro-4-(2-oxo-pyridin-1-yl)-phenylcarbamoyl]-methyl}-pyrrolidine-2-carboxylic acid (example 12) was coupled with 2-aminoethanol to give (2S,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid (2-hydroxy-ethyl)-amide. White solid. MS 562.5 ([M+H]$^+$)

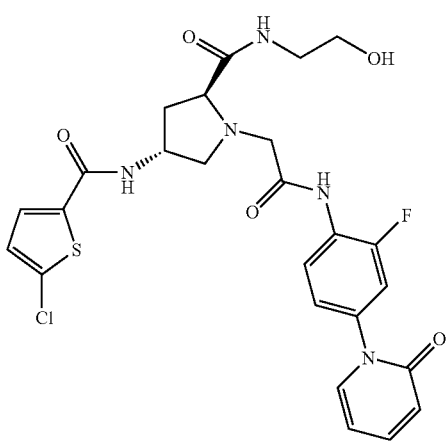

Example 14

Using general procedure D (2S,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid (example 12) was coupled with aminomethylcyclopropane to give (2S,4R)-4-[(5-chloro-thiophene-2-carbonyl)-amino]—1-{[2-fluoro-4-(2-oxo-pyridin-1-yl)-phenylcarbamoyl]-methyl}-pyrrolidine-2-carboxylic acid cyclopropylmethyl-amide and (2R,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid cyclopropylmethyl-amide. White solid (both products). MS 572.3 ([M+H]$^+$)

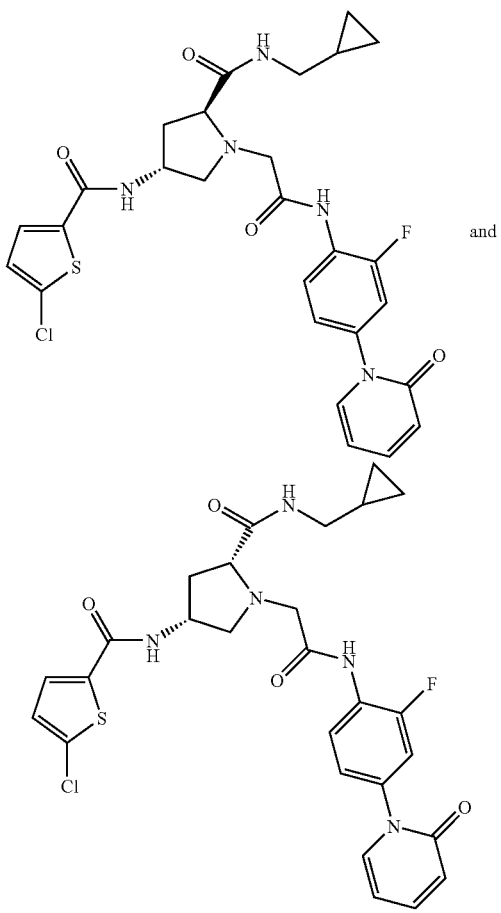

and

Example 15

Using general procedure D (2S,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid (example 12) was coupled with methylamine hydrochloride to give (2S,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid methylamide. White solid. MS 532.3 ([M+H]$^+$)

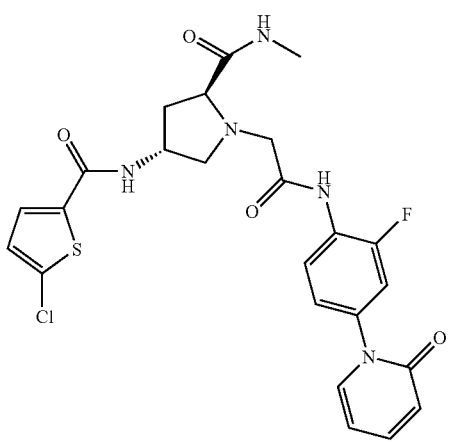

Example 16

To a solution of 44 mg cyanuric chloride in 1.5 ml 1,2-dimethoxyethane were added 0.03 ml N-methylmorpholine. The resulting white suspension was treated with 150 mg (2S,4R)-4-[(5-chloro-thiophene-2-carbonyl)-amino]-1-{[2-fluoro-4-(2-oxo-pyridin-1-yl)-phenylcarbamoyl]-methyl}-pyrrolidine-2-carboxylic acid (example 12) in 0.5 ml 1,2-dimethoxyethane and stirred at r.t for 3 hrs. The precipitate was filtered off. The filtrate was cooled to 0° C. A solution of 13 mg NaBH$_4$ in 0.7 ml H$_2$O was added dropwise. The mixture was stirred for 5 min at 0° C., then diluted with water and extracted with EtOAc. The organic layer was washed with water, dried over MgSO$_4$, filtrated and concentrated. The crude product was purified by chromatography (silica gel; gradient: CH$_2$Cl$_2$->CH$_2$Cl$_2$/MeOH 9:1) to give 20 mg 5-chloro-thiophene-2-carboxylic acid ((3R,5S)-1-{[2-fluoro-4-(2-oxo-pyridin-1-yl)-phenylcarbamoyl]-methyl}-5-hydroxymethyl-pyrrolidin-3-yl)-amide. White solid. MS 505.4 ([M+H]$^+$)

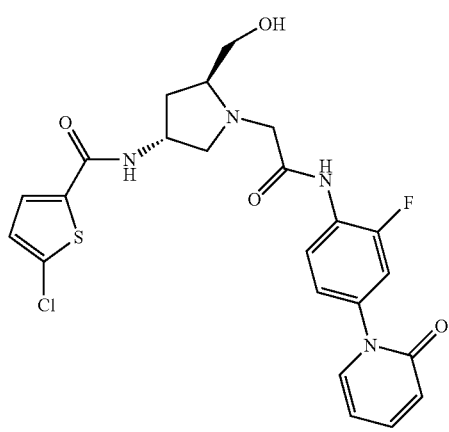

Example 17

17.1 To a stirred solution of 6.98 g (2S,4R)-4-[(5-chloro-thiophene-2-carbonyl)-amino]-pyrrolidine-1,2-dicarboxylic acid 1-tert-butyl ester 2-methyl ester (example 11.1) at 0° C. in 125 ml methanol under an argon atmosphere were added 3.05 g lithium chloride (3.046 g, 4 eq.) and 1.36 g NaBH$_4$ and stirring was continued for 1 h at 0° C. The ice bath was removed. The off-white slurry was stirred at r.t. for 6 hrs. The mixture was cooled to 0° C. and treated with 25 ml THF and 1.36 g NaBH$_4$. The ice bath was removed and stirring was overnight. Then the mixture was filtered and the filtrate was concentrated to leave a light yellow sticky solid. The crude product was purified by column chromatography (silica gel, gradient: CH$_2$Cl$_2$->CH$_2$Cl$_2$/MeOH 95.5) to give—along with 1.12 g starting material—4.11 g (2S,4R)-4-[(5-chloro-thiophene-2-carbonyl)-amino]-2-hydroxymethyl-pyrrolidine-1-carboxylic acid tert-butyl ester as white solid. MS 361.4 ([M+H]$^+$)

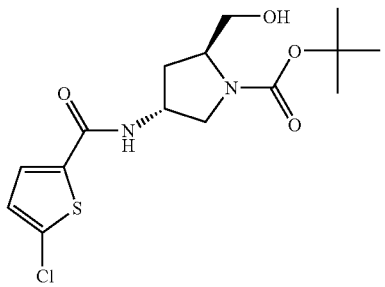

17.2 To a stirred solution of 2.5 g (2S,4R)-4-[(5-chloro-thiophene-2-carbonyl)-amino]-2-hydroxymethyl-pyrrolidine-1-carboxylic acid tert-butyl ester at 0° C. in 10 ml dichloromethane under an argon atmosphere were added 5.89 ml N-ethyldiisopropylamine and 0.65 ml methanesulfonyl chloride. The mixture was stirred at 0° C. for 4 h, then diluted with DCM and washed with H$_2$O and brine, dried over MgSO$_4$, filtered and concentrated. The crude product was isolated by column chromatography (silica gel, gradient: CH$_2$Cl$_2$->CH$_2$Cl$_2$/MeOH 95:5) to give 2.42 g (2S,4R)-4-[(5-chloro-thiophene-2-carbonyl)-amino]-2-methanesulfonyloxymethyl-pyrrolidine-1-carboxylic acid tert-butyl ester as off-white amorphous solid. MS 439.1 ([M+H]$^+$)

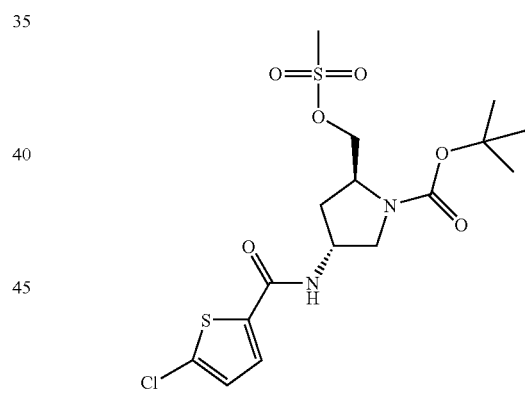

17.3 To a stirred solution of 200 mg (2S,4R)-4-[(5-chloro-thiophene-2-carbonyl)-amino]-2-methanesulfonyloxymethyl-pyrrolidine-1-carboxylic acid tert-butyl ester at r.t. in 5 ml THF under an argon atmosphere were added 0.38 ml pyrrolidine. The mixture was heated to reflux for 6 h, then cooled to r.t. and concentrated. The crude product was purified by column chromatography (silica gel, gradient CH$_2$Cl$_2$->CH$_2$Cl$_2$/MeOH 9:1) to give 138 mg (2S,4R)-4-[(5-chloro-thiophene-2-carbonyl)-amino]-2-pyrrolidin-1-ylmethyl-pyrrolidine-1-carboxylic acid tert-butyl ester as off-white amorphous solid. MS 414.4 ([M+H]$^+$)

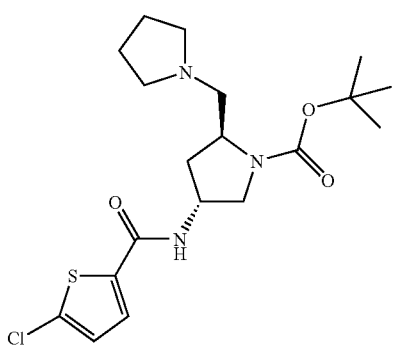

17.4 To a stirred solution of 134 mg (2S,4R)-4-[(5-chloro-thiophene-2-carbonyl)-amino]-2-pyrrolidin-1-ylmethyl-pyrrolidine-1-carboxylic acid tert-butyl ester at r.t. in 3.4 ml dioxane under an argon atmosphere were added 1.6 ml 4 M HCl in dioxane. The mixture was then stirred for 18 h. The resulting white suspension was concentrated to leave 139 mg 5-chloro-thiophene-2-carboxylic acid ((3R,5S)-5-pyrrolidin-1-ylmethyl-pyrrolidin-3-yl)-amide dihydrochloride as off-white solid. MS 314.3 ([M+H]$^+$)

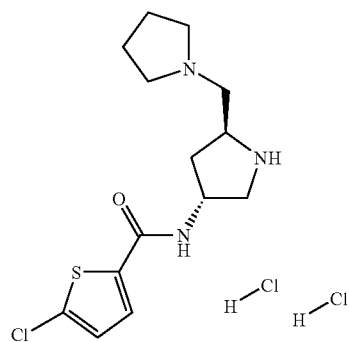

17.5 Using general procedure A 5-chloro-thiophene-2-carboxylic acid ((3R,5S)-5-pyrrolidin-1-ylmethyl-pyrrolidin-3-yl)-amide was reacted with 2-bromo-[2-fluoro-4-(2-oxo-pyridin-1-yl)-phenyl]-acetamide (example 11.3) to give 5-chloro-thiophene-2-carboxylic acid ((3R,5S)-1-{[2-fluoro-4-(2-oxo-2H-pyridin-1-yl)-phenylcarbamoyl]-methyl}-5-pyrrolidin-1-ylmethyl-pyrrolidin-3-yl)-amide. Light yellow solid. MS 558.2 ([M+H]$^+$)

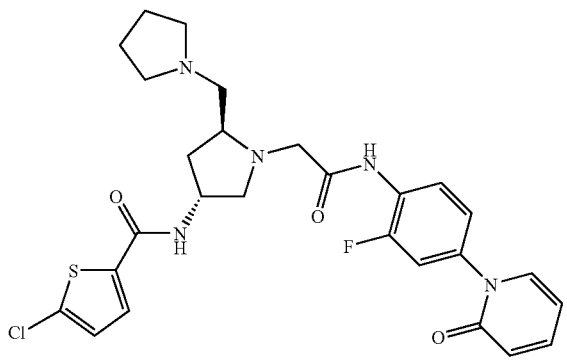

Example 18

18.1 To a stirred solution of 200 mg (2S,4R)-4-[(5-chloro-thiophene-2-carbonyl)-amino]-2-methanesulfonyloxymethyl-pyrrolidine-1-carboxylic acid tert-butyl ester (example 17.2) at r.t. in 5 ml THF under an argon atmosphere were added 78 mg sodium methylate. The resulting suspension was heated to reflux for 4 hrs, then treated again with 78 mg sodium methylate and 1.5 ml MeOH and refluxed overnight. The reaction mixture was cooled to r.t. and concentrated. The crude product was purified by column chromatography (silica gel, gradient: cyclohexane->cyclohexane/EtOAc 35:65) to give (2S,4R)-4-[(5-chloro-thiophene-2-carbonyl)-amino]-2-methoxymethyl-pyrrolidine-1-carboxylic acid tert-butyl ester as colorless gum. MS 375.0 ([M+H]$^+$)

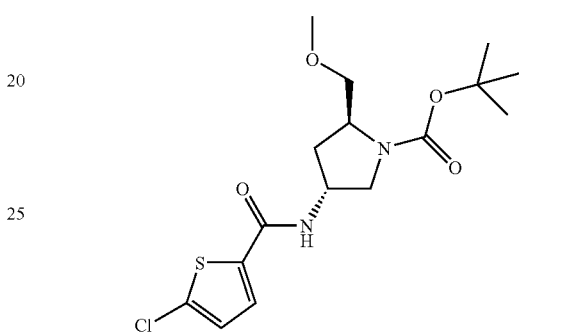

18.2 In analogy to examples 17.4 and 17.5 (2S,4R)-4-[(5-chloro-thiophene-2-carbonyl)-amino]-2-methoxymethyl-pyrrolidine-1-carboxylic acid tert-butyl ester was converted to 5-chloro-thiophene-2-carboxylic acid ((3R,5S)-1-{[2-fluoro-4-(2-oxo-2H-pyridin-1-yl)-phenylcarbamoyl]-methyl}-5-methoxymethyl-pyrrolidin-3-yl)-amide. Off-white solid. MS 519.3 ([M+H]$^+$)

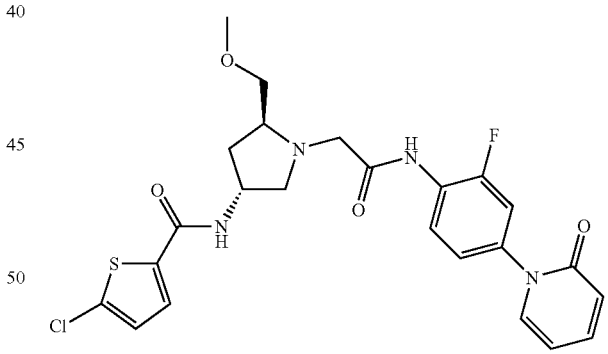

Example 19

19.1 To a stirred, cooled (0° C.) suspension of 30 mg NaH (55% dispersion in mineral oil) in 1.5 ml DMF under an argon atmosphere were added a solution of 58 mg 2-pyrrolidinone in 1.5 ml DMF. The ice bath was removed and stirring at r.t. was continued for 1 h 30. The mixture was cooled again and a solution of 200 mg (2S,4R)-4-[(5-chloro-thiophene-2-carbonyl)-amino]-2-methanesulfonyloxymethyl-pyrrolidine-1-carboxylic acid tert-butyl ester (example 17.2) in 2 ml DMF was added. The temperature was elevated to 80° C. The reaction mixture was stirred over night, was cooled to r.t., diluted with EtOAc and washed with H$_2$O. The aqueous phase was back-extracted with EtOAc. The combined organics were washed with H$_2$O and brine, dried over MgSO$_4$, filtered and concentrated. The crude product was purified by column chromatography (silica gel, gradient: CH$_2$Cl$_2$->CH$_2$Cl$_2$/MeOH 95:5) to give 46 mg (2S,4R)-4-[(5-chloro-thiophene-2-carbonyl)-amino]-2-(2-oxo-pyrrolidin-1-ylmethyl)-pyrrolidine-1-carboxylic acid tert-butyl ester as colorless gum. MS 428.3 ([M+H]$^+$)

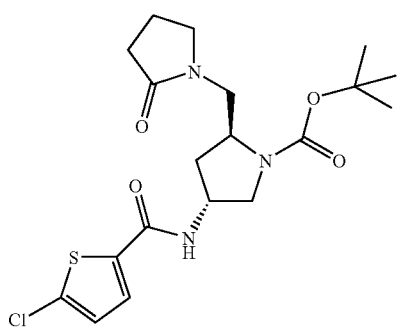

19.2 In analogy to examples 17.4 and 17.5 (2S,4R)-4-[(5-chloro-thiophene-2-carbonyl)-amino]-2-(2-oxo-pyrrolidin-1-ylmethyl)-pyrrolidine-1-carboxylic acid tert-butyl ester was converted to 5-chloro-thiophene-2-carboxylic acid [(3R,5S)-1-{[2-fluoro-4-(2-oxo-2H-pyridin-1-yl)-phenylcarbamoyl]-methyl}-5-(2-oxo-pyrrolidin-1-ylmethyl)-pyrrolidin-3-yl]-amide. Off-white amorphous solid. MS 572.3 ([M+H]$^+$)

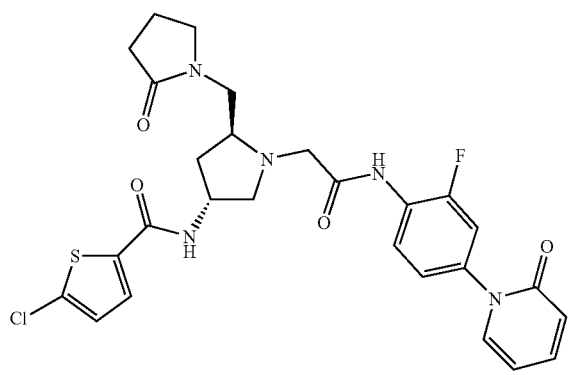

Example 20

20.1 To a stirred solution of 550 mg (2S,4R)-4-[(5-chloro-thiophene-2-carbonyl)-amino]-2-methanesulfonyloxymethyl-pyrrolidine-1-carboxylic acid tert-butyl ester (example 17.2) at r.t. in 5 ml DMF under an argon atmosphere were added 98 mg NaN$_3$. The mixture was heated to 90° C. and stirred over night. The mixture was cooled to r.t., diluted with EtOAc and washed with H$_2$O and brine. The combined organics were dried over MgSO$_4$, filtered and concentrated to leave 552 mg of the crude azide as a light yellow viscous oil. It was dissolved in 7 ml THF. To the solution were added 986 mg triphenylphosphine and 0.5 ml H$_2$O. The reaction mixture was stirred overnight, then concentrated. The crude product was purified by column chromatography (silica gel, gradient: CH$_2$Cl$_2$->CH$_2$Cl$_2$/MeOH 95:5) to give 326 mg (2S,4R)-2-aminomethyl-4-[(5-chloro-thiophene-2-carbonyl)-amino]-pyrrolidine-1-car-boxylic acid tert-butyl ester as off-white amorphous solid. MS 360.3 ([M+H]$^+$)

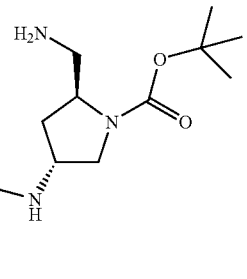

20.2 To a stirred, cooled solution of 150 mg (2S,4R)-2-aminomethyl-4-[(5-chloro-thiophene-2-carbonyl)-amino]-pyrrolidine-1-carboxylic acid tert-butyl ester in 5 ml dichloromethane under an argon atmosphere were added 0.29 ml triethylamine and 0.04 ml methanesulfonyl chloride. The mixture was slowly warmed to r.t., stirred over night and then concentrated. The crude product was isolated by column chromatography (silica gel, gradient: CH$_2$Cl$_2$->CH$_2$Cl$_2$/MeOH 95:5) to give 165 mg (2S,4R)-4-[(5-chloro-thiophene-2-carbonyl)-amino]-2-(methanesulfonylamino-methyl)-pyrrolidine-1-carboxylic acid tert-butyl ester as off-white amorphous solid. MS 435.9 ([M-H]$^-$)

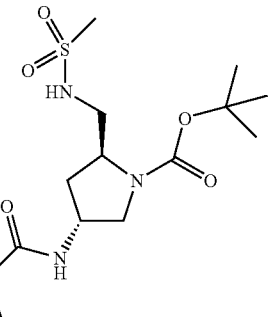

20.3 In analogy to examples 17.4 and 17.5 (2S,4R)-4-[(5-chloro-thiophene-2-carbonyl)-amino]-2-(methanesulfonylamino-methyl)-pyrrolidine-1-carboxylic acid tert-butyl ester was converted to 5-chloro-thiophene-2-carboxylic acid [(3R,5S)-1-{[2-fluoro-4-(2-oxo-2H-pyridin-1-yl)-phenylcarbamoyl]-methyl}-5-(methanesulfonylamino-methyl)-pyrrolidin-3-yl]-amide. Off-white solid. MS 582.2 ([M+H]$^+$)

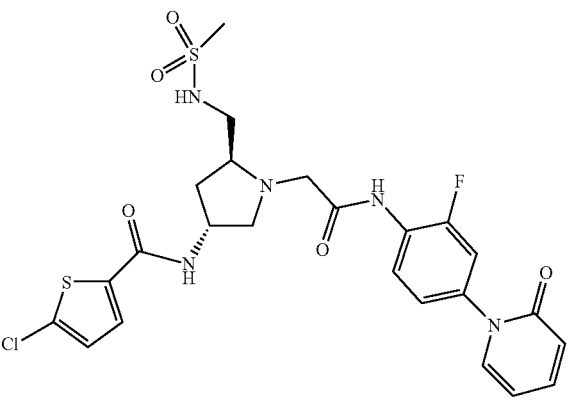

Example 21

In analogy to examples 20.2 and 20.3 (2S,4R)-2-aminomethyl-4-[(5-chloro-thiophene-2-carbonyl)-amino]-pyrrolidine-1-carboxylic acid tert-butyl ester was reacted with acetyl chloride and further converted to 5-chloro-thiophene-2-carboxylic acid ((3R,5S)-5-(acetylamino-methyl)-1-{[2-fluoro-4-(2-oxo-2H-pyridin-1-yl)-phenylcarbamoyl]-methyl}-pyrrolidin-3-yl)-amide. Light yellow solid. MS 546.3 ([M+H]$^+$)

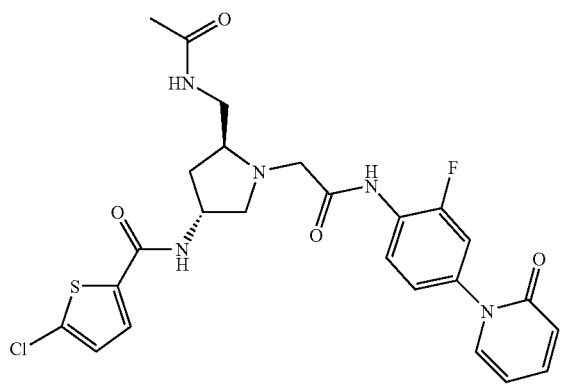

Example 22

22.1 A solution of 19.6 g N-Boc-pyrroline in 200 ml CH$_2$Cl$_2$ was cooled to –10° C. and was treated in two portions with 30 g meta-chloroperbenzoic acid. The mixture was stirred for 17 h, slowly warming up to room temperature. Then, the white precipitate was filtered off and washed with dichloromethane. The filtrate was washed with 5% aq. NaHSO$_3$, sat. aq. NaHCO$_3$ and brine, dried (MgSO$_4$), filtered and concentrated. The crude product was purified by chromatography (silica gel; gradient: cyclohexane->cyclohexane/EtOAc 65:35) to give 11.8 g 6-oxa-3-aza-bicyclo[3.1.0]hexane-3-carboxylic acid tert-butyl ester as a light yellow oil. MS 186.1 ([M+H]$^+$)

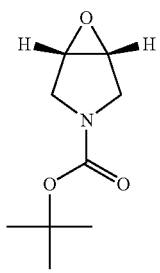

22.2 A solution of 9.7 g 6-oxa-3-aza-bicyclo[3.1.0]hexane-3-carboxylic acid tert-butyl ester in 480 ml MeOH was thoroughly degassed and flushed with argon. It was treated with 660 mg (1R,2R)-(−)-[1,2-cyclohexanediamino-N,N'-bis(3,5-di-t-butylsalicylidene)]-chromium (III) chloride (CAS 164931-83-3; available from Strem). The resulting heterogenous mixture was again degassed, flushed with argon, cooled to 0° C. and treated with 7.2 ml trimethyl silyl azide. The dark red-brown slurry (slowly warming up to room temperature, and becoming more and more compact) was stirred at r.t. for 21 h. Then, the mixture was taken up in MeOH and treated with 7.71 g K$_2$CO$_3$. Stirring at r.t. under an argon atmosphere was continued for 24 h, the mixture slowly turning to a clear red/brown solution. The mixture was concentrated. The orange-brown residue was taken up in CH$_2$Cl$_2$ and washed with H$_2$O. The organic layer was filtered, washed with brine, dried over MgSO$_4$ and concentrated. The crude product was purified by chromatography (silica gel; gradient: cyclohexane->cyclohexane/EtOAc 1:1) to give 9.7 g (3S,4S)-3-azido-4-hydroxy-pyrrolidine-1-carboxylic acid tert-butyl ester as yellow viscous oil. MS 287.1 ([M+AcO$^-$]$^-$)

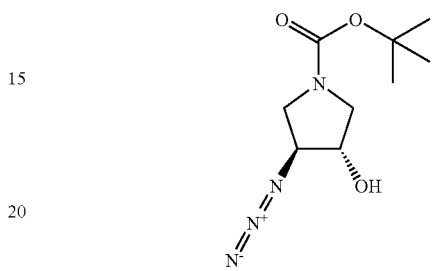

22.3 A solution of 2.0 g (3S,4S)-3-azido-4-hydroxy-pyrrolidine-1-carboxylic acid tert-butyl ester in 25 MeOH was treated under an argon atmosphere with 100 mg PtO$_2$. The reaction mixture was stirred over night under a hydrogen atmosphere. The catalyst was filtered off and washed with methanol. The filtrate was concentrated. The crude product was purified by chromatography (silica gel; gradient: CH$_2$Cl$_2$->CH$_2$Cl$_2$/MeOH 4:1) to give 1.5 g (3S,4S)-3-amino-4-hydroxy-pyrrolidine-1-carboxylic acid tert-butyl ester as off-white solid. MS 202.9 ([M+H]$^+$)

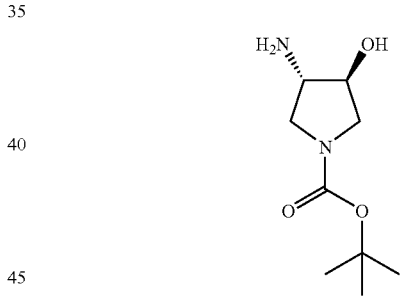

22.4 Using general procedure C (3S,4S)-3-amino-4-hydroxy-pyrrolidine-1-carboxylic acid tert-butyl ester was reacted with 5-chlorothiophene-2-carboxylic acid to give (3S,4S)-3-[(5-chloro-thiophene-2-carbonyl)-amino]-4-hydroxy-pyrrolidine-1-carboxylic acid tert-butyl ester. Off-white solid. MS 347.3 ([M+H]$^+$)

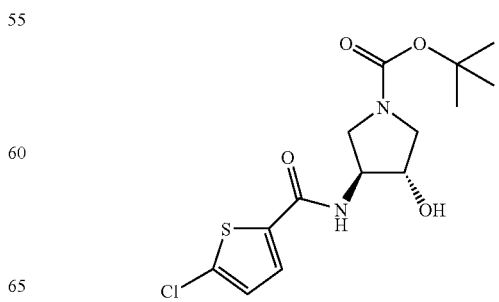

22.5 Using general procedure B (3S,4S)-3-[(5-chloro-thiophene-2-carbonyl)-amino]-4-hydroxy-pyrrolidine-1-carboxylic acid tert-butyl ester was deprotected to give 5-chloro-thiophene-2-carboxylic acid ((3S,4S)-4-hydroxy-pyrrolidin-3-yl)-amide hydrochloride. Off-white solid. MS 247.1 ([M+H]+)

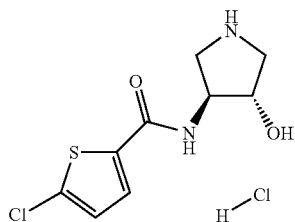

22.6 Using general procedure A with DMF as solvent 5-chloro-thiophene-2-carboxylic acid ((3S,4S)-4-hydroxy-pyrrolidin-3-yl)-amide hydrochloride was reacted with 2-bromo-[2-fluoro-4-(2-oxo-pyridin-1-yl)-phenyl]-acetamide to give 5-chloro-thiophene-2-carboxylic acid ((3S,4S)-1-{[2-fluoro-4-(2-oxo-2H-pyridin-1-yl)-phenylcarbamoyl]-methyl}-4-hydroxy-pyrrolidin-3-yl)-amide. Light-yellow solid. MS 491.3 ([M+H]+)

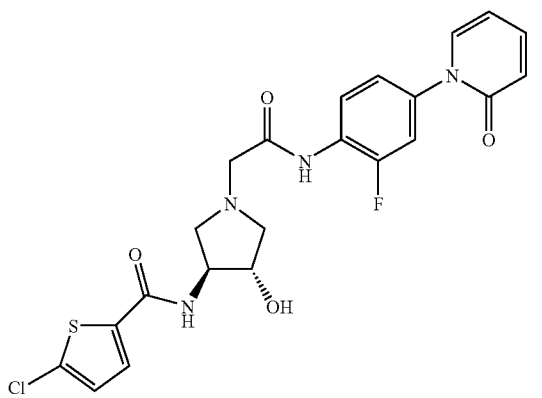

Example 23

Using analogous procedures as described in examples 22.4-22.6 (3S,4R)-3-amino-4-hydroxy-pyrrolidine-1-carboxylic acid tert-butyl ester (CAS 190792-75-7; prepared from (3S,4S)-3-amino-4-hydroxy-pyrrolidine-1-carboxylic acid tert-butyl ester (example 22.3) as described by S. E. Schaus, J. F. Larrow, E. N. Jacobsen in *Journal of Organic Chemistry*, 1997, 62(12), 4197) was converted to 5-chloro-thiophene-2-carboxylic acid ((3R,4S)-1-{[2-fluoro-4-(2-oxo-pyridin-1-yl)-phenylcarbamoyl]-methyl}-4-hydroxy-pyrrolidin-3-yl)-amide. White solid. MS 491.4 ([M+H]+)

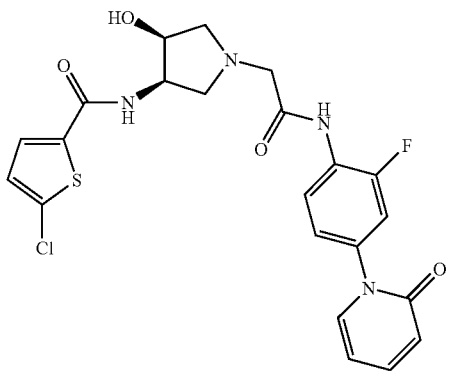

Example 24

24.1 A solution of 1.0 g (3S,4S)-3-azido-4-hydroxy-pyrrolidine-1-carboxylic acid tert-butyl ester (example 22.2) in 15 ml acetonitrile and 3 ml THF was treated with 3.0 g silver(I) oxide and and 2.7 ml iodomethane. The reaction mixture was stirred over night at r.t., then again treated with 3.0 g silver(I) oxide and 2.7 ml iodomethane. The reaction was agitated over night at r.t., then filtrated. The filtrate was concentrated. The crude product was purified by chromatography (silica gel; cyclohexane/EtOAc 2:1) to give 1.0 g (3S,4S)-3-azido-4-methoxy-pyrrolidine-1-carboxylic acid tert-butyl ester as light yellow oil. MS 243.4 ([M+H]+)

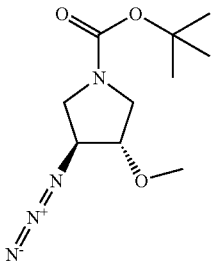

24.2 Using analogous procedures as described in examples 17.3-17.6 (3S,4S)-3-azido-4-methoxy-pyrrolidine-1-carboxylic acid tert-butyl ester was converted to 5-chloro-thiophene-2-carboxylic acid ((3S,4S)-1-{[2-fluoro-4-(2-oxo-2H-pyridin-1-yl)-phenylcarbamoyl]-methyl}-4-methoxy-pyrrolidin-3-yl)-amide. Light yellow amorphous solid. MS 505.3 ([M+H]+)

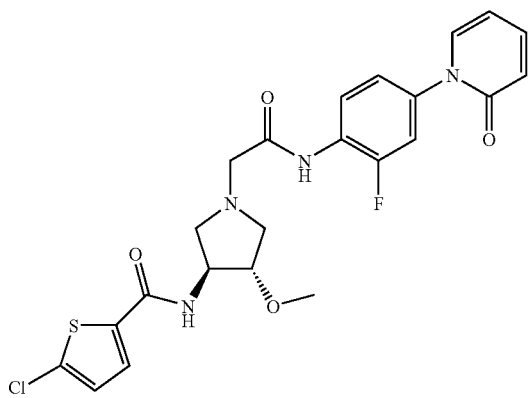

Example 25

25.1 Using analogous procedures as described in examples 22.3 and 22.4 (3S,4S)-3-azido-4-methoxy-pyrrolidine-1-carboxylic acid tert-butyl ester (example 24.1) was converted to (3S,4S)-3-[(5-chloro-thiophene-2-carbonyl)-amino]-4-methoxy-pyrrolidine-1-carboxylic acid tert-butyl ester. White solid. MS 361.4 ([M+H]⁺)

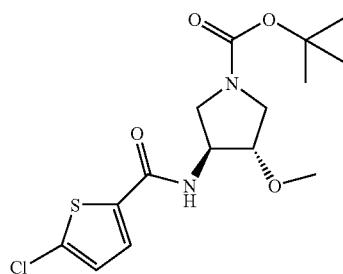

25.2 Using analogous procedures as described in examples 6.2 and 6.3 (3S,4S)-3-[(5-chloro-thiophene-2-carbonyl)-amino]-4-methoxy-pyrrolidine-1-carboxylic acid tert-butyl ester was converted to {(3S,4S)-3-[(5-chloro-thiophene-2-carbonyl)-amino]-4-methoxy-pyrrolidin-1-yl}-acetic acid ethyl ester. Oil. MS 347.1 ([M+H]⁺)

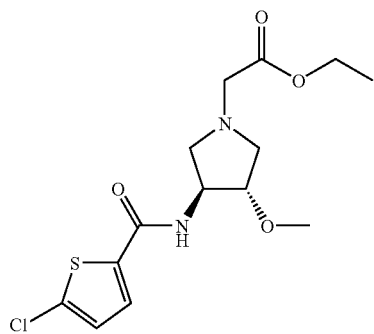

25.3 Using general procedure F {(3S,4S)-3-[(5-chloro-thiophene-2-carbonyl)-amino]-4-methoxy-pyrrolidin-1-yl}-acetic acid ethyl ester was reacted with 1-(4-amino-phenyl)-1H-pyridin-2-one (CAS 13143-47-0) to give 5-chloro-thiophene-2-carboxylic acid ((3S,4S)-4-methoxy-1-{[4-(2-oxo-2-pyridin-1-yl)-phenylcarbamoyl]-methyl}-pyrrolidin-3-yl)-amide. Yellow solid. MS 487.1 ([M+H]⁺)

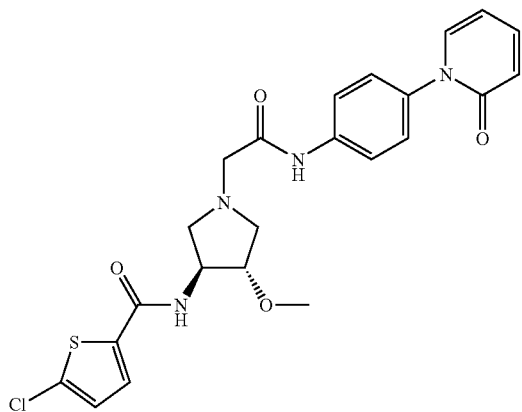

Example 26

Using general procedure F {(3S,4S)-3-[(5-chloro-thiophene-2-carbonyl)-amino]-4-methoxy-pyrrolidin-1-yl}-acetic acid ethyl ester (example 25.2) was reacted with 4-(4-amino-3-fluoro-phenyl)-morpholin-3-one (CAS 438056-69-0) to give 5-chloro-thiophene-2-carboxylic acid ((3S,4S)-1-{[2-fluoro-4-(3-oxo-morpholin-4-yl)-phenylcar-bamoyl]-methyl}-4-methoxy-pyrrolidin-3-yl)-amide. Yellow solid. MS 511.3 ([M+H]⁺)

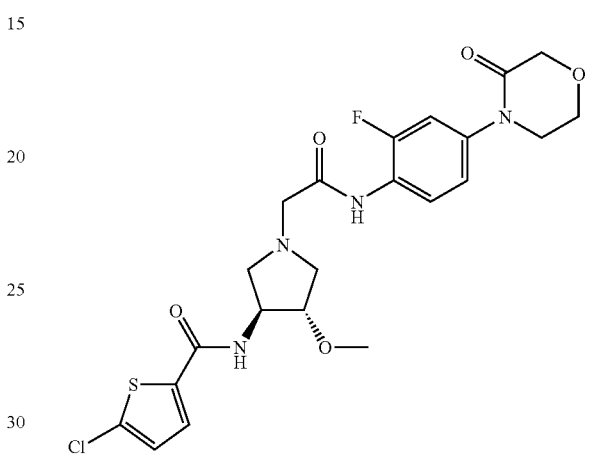

Example 27

Using general procedure F {(3S,4S)-3-[(5-chloro-thiophene-2-carbonyl)-amino]-4-methoxy-pyrrolidin-1-yl}-acetic acid ethyl ester (example 25.2) was reacted with 1-(4-amino-3-fluoro-phenyl)-1H-pyrazin-2-one (prepared from 2-fluoro-4-iodoaniline by reaction with 1H-pyrazin-2-one, Cu(I)I, N,N'-dimethylethylenediamine and cesium carbonate in dioxane at 120° C.) to give 5-chloro-thiophene-2-carboxylic acid ((3S,4S)-1-{[2-fluoro-4-(2-oxo-pyrazin-1-yl)-phenylcarbamoyl]-methyl}-4-methoxy-pyrrolidin-3-yl)-amide. Yellow solid. MS 506.3 ([M+H]⁺)

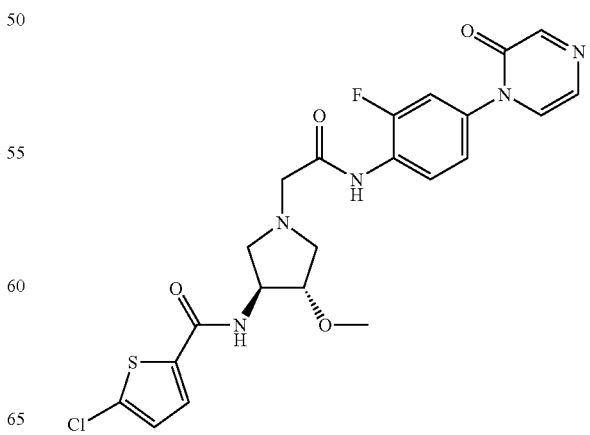

Example 28

Using general procedure F {(3S,4S)-3-[(5-chloro-thiophene-2-carbonyl)-amino]-4-methoxy-pyrrolidin-1-yl}-acetic acid ethyl ester (example 25.2) was reacted with 4-(4-aminophenyl)-morpholin-3-one (CAS 438056-69-0) to give 5-chloro-thiophene-2-carboxylic acid ((3S,4S)-4-methoxy-1-{[4-(3-oxo-morpholin-4-yl)-phenylcarbamoyl]-methyl}-pyrrolidin-3-yl)-amide. Yellow solid. MS 493.0 ([M+H]$^+$)

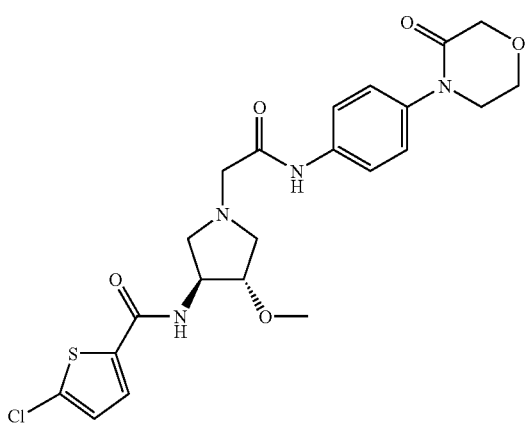

Example 29

29.1 A solution of 150 mg (3S,4S)-3-[(5-chloro-thiophene-2-carbonyl)-amino]-4-hydroxy-pyrrolidine-1-carboxylic acid tert-butyl ester (example 22.4) in 3 ml MeCN and 1 ml THF was treated with 300 mg silver(I) oxide and 0.35 ml iodoethane. The reaction mixture was stirred over night, then was again treated with 300 mg silver(I) oxide and 0.35 ml iodoethane. The reaction mixture was agitated over night at r.t., then filtrated. The filtrate was concentrated. The crude product was purified by chromatography (silica gel; gradient: cyclohexane->EtOAc) to give 90 mg (3S,4S)-3-[(5-chloro-thiophene-2-carbonyl)-amino]-4-ethoxy-pyrrolidine-1-carboxylic acid tert-butyl ester as light yellow oil. MS 373.1 ([M–H]$^-$)

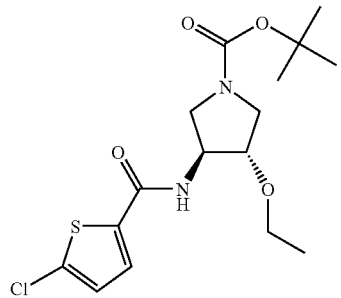

29.2 Using analogous procedures as described in examples 22.5 and 22.6 (3S,4S)-3-[(5-chloro-thiophene-2-carbonyl)-amino]-4-ethoxy-pyrrolidine-1-carboxylic acid tert-butyl ester was converted to 5-chloro-thiophene-2-carboxylic acid ((3S,4S)-4-ethoxy-1-{[2-fluoro-4-(2-oxo-pyridin-1-yl)-phenylcarbamoyl]-methyl}-pyrrolidin-3-yl)-amide. Yellow solid. MS 519.3 ([M+H]$^+$)

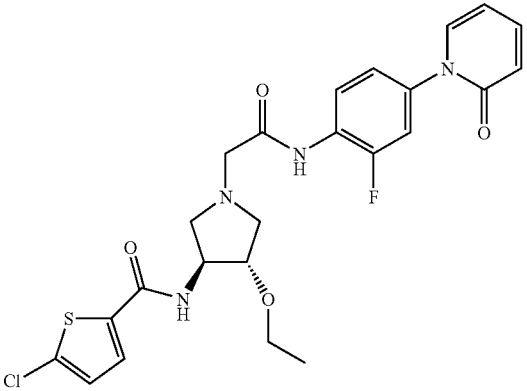

Example 30

30.1 A suspension of 37 mg NaH (55% in oil) in 2 ml DMF was treated at 0° C. under an argon atmosphere with a solution of 270 mg (3S,4S)-3-[(5-chloro-thiophene-2-carbonyl)-amino]-4-hydroxy-pyrrolidine-1-carboxylic acid tert-butyl ester (example 22.4). The reaction mixture was stirred for 1 hr at r.t. Then, 334 mg 2,2-difluoroethyl trifluoromethane-sulfonate were added at 0° C. The reaction mixture was stirred for 2 days at r.t., then diluted with EtOAc and washed with water. The organic layer was dried over MgSO4, filtered and concentrated. The crude product was isolated by chromatography (silica gel; gradient: cyclohexane->cyclohexane/EtOAc 9:1) to give 157 mg (3S,4S)-3-[(5-chloro-thiophene-2-carbonyl)-amino]-4-(2,2-difluoro-ethoxy)-pyrrolidine-1-carboxylic acid tert-butyl ester. Colorless solid. MS 409.0 ([M+H]$^+$)

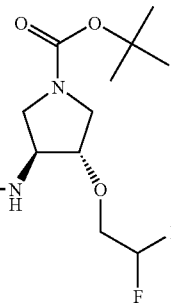

30.2 Using analogous procedures as described in examples 22.5 and 22.6 (3S,4S)-3-[(5-chloro-thiophene-2-carbonyl)-amino]-4-(2,2-difluoro-ethoxy)-pyrrolidine-1-carboxylic acid tert-butyl ester was converted to 5-chloro-thiophene-2-carboxylic acid ((3S,4S)-4-(2,2-difluoro-ethoxy)-1-{[2-fluoro-4-(2-oxo-pyridin-1-yl)-phenylcarbamoyl]-methyl}-pyrrolidin-3-yl)-amide. Yellow solid. MS 555.2 ([M+H]$^+$)

Example 31

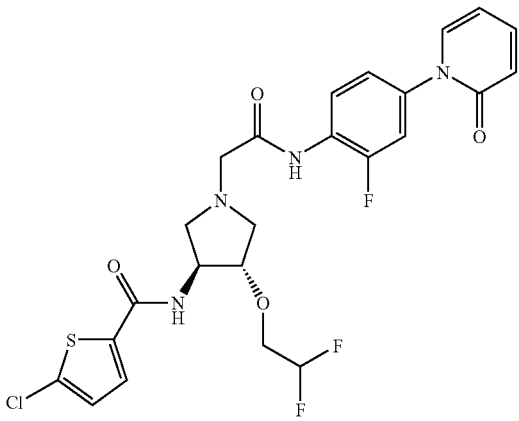

31.1 A suspension of 187 mg NaH (55% dispersion in mineral oil) in 3 ml DMF under an argon atmosphere was cooled to 0° C. and treated with a solution of 960 mg (3S,4S)-3-azido-4-hydroxy-pyrrolidine-1-carboxylic acid tert-butyl ester (example 22.2) in 6 ml DMF. The ice bath was removed and stirring at r.t. was continued for 90 min. The mixture was cooled to 0° C. and a solution 0.7 ml 2-(2-bromoethoxy)tetrahydro-2H-pyran in 1 ml DMF was added. The mixture (slowly warming up to room temperature) was then stirred for 18 h. The reaction mixture was diluted with EtOAc and washed with H₂O. The aqueous phase was back extracted with EtOAc. The combined organics were washed with H2O and brine, dried over MgSO4, filtered and concentrated. The crude product was isolated by column chromatography (silica gel; gradient: cyclohexane->cyclohexane/EtOAc 3:2) to give 545 mg (3S,4S)-03-azido-4-[2-(tetrahydro-pyran-2-yloxy)-ethoxy]-pyrrolidine-1-carboxylic acid tert-butyl ester as light yellow viscous oil. MS 357.3 ([M+H]$^+$)

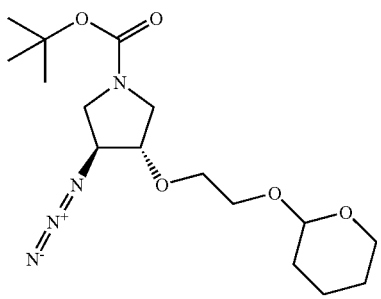

31.2 Using analogous procedure as described in examples 22.3-22.6 (3S,4S)-3-azido-4-[2-(tetrahydro-pyran-2-yloxy)-ethoxy]-pyrrolidine-1-carboxylic acid tert-butyl ester was converted to 5-chloro-thiophene-2-carboxylic acid [(3S,4S)-1-{[2-fluoro-4-(2-oxo-2H-pyridin-1-yl)-phenylcarbamoyl]-methyl}-4-(2-hydroxy-ethoxy)-pyrrolidin-3-yl]-amide. White amorphous solid. MS 535.5 ([M+H]$^+$)

Example 32

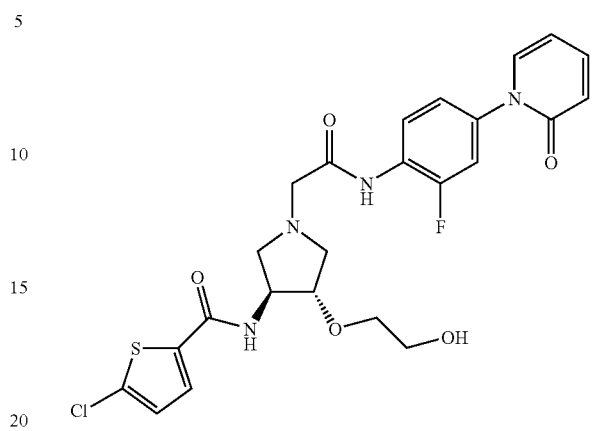

32.1 A solution of 480 mg (3S,4S)-3-[(5-chloro-thiophene-2-carbonyl)-amino]-4-hydroxy-pyrrolidine-1-carboxylic acid tert-butyl ester (example 22.4) in 14 ml DMSO/CH₂Cl₂ 1:1 was cooled to 0° C. and treated with 1.34 ml TEA and 934 mg sulfur trioxide-pyridine complex. The reaction mixture was warmed to r.t., stirred for 2 hrs, then diluted with CH₂Cl₂ and washed with water. The organic layer was dried over MgSO₄, filtrated and concentrated. The crude product was purified by column chromatography (silica gel, CH₂Cl₂/MeOH 95:5) to give 315 mg 5-chloro-thiophene-2-carboxylic acid ((S)-1-{[2-fluoro-4-(2-oxo-2-pyridin-1-yl)-phenylcarbamoyl]-methyl}-4-oxo-pyrrolidin-3-yl)-amide as off-white amorphous solid. MS 489.0 ([M−H]$^−$)

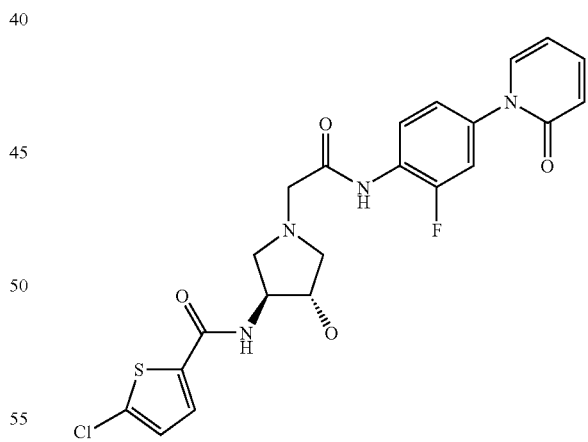

32.2 A solution of 100 mg 5-chloro-thiophene-2-carboxylic acid ((S)-1-{[2-fluoro-4-(2-oxo-2-pyridin-1-yl)-phenylcarbamoyl]-methyl}-4-oxo-pyrrolidin-3-yl)-amide in 10 ml MeOH was treated with 1.58 g ammonium acetate and 14 mg NaBH₃CN. The reaction mixture was stirred at r.t. overnight, then concentrated and taken up in CH₂Cl₂. The solids were filtered off. The filtrate was concentrated to leave the crude product which was isolated by column chromatography (silica gel, gradient: CH₂Cl₂->CH₂Cl₂/MeOH 4:1) to give 8 mg 5-chloro-thiophene-2-carboxylic acid ((S)-4-amino-1-

{[2-fluoro-4-(2-oxo-2-pyridin-1-yl)-phenylcarbamoyl]-methyl}-pyrrolidin-3-yl)-amide as off-white solid. MS 490.1 ([M+H]$^+$)

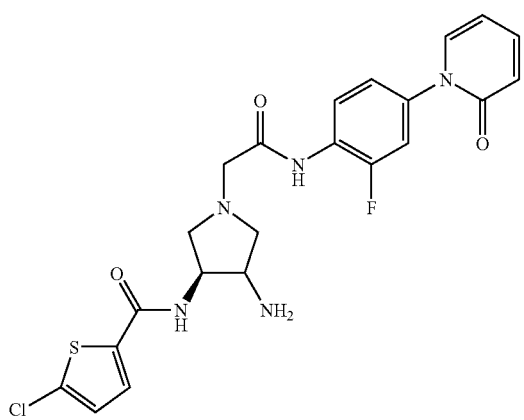

Example 33

A solution of 50 mg 5-chloro-thiophene-2-carboxylic acid ((S)-1-{[2-fluoro-4-(2-oxo-2-pyridin-1-yl)-phenylcarbamoyl]-methyl}-4-oxo-pyrrolidin-3-yl)-amide (example 32.1) in 2 ml THF was treated with 0.04 ml dimethylamine solution (33% in EtOH) and cooled to 0° C. The reaction mixture was brought to pH 5 by the addition of AcOH. Then, 7 mg of NaBH$_3$CN were added. The reaction mixture was stirred at r.t. overnight, then concentrated. The crude product was isolated by column chromatography (silica gel, gradient: CH$_2$Cl$_2$->CH$_2$Cl$_2$/MeOH 9:1) to give 14 mg 5-chloro-thiophene-2-carboxylic acid ((S)-4-dimethylamino-1-{[2-fluoro-4-(2-oxo-2-pyridin-1-yl)-phenylcarbamoyl]-methyl}-pyrrolidin-3-yl)-amide as white solid. MS 518.5 ([M+H]$^+$)

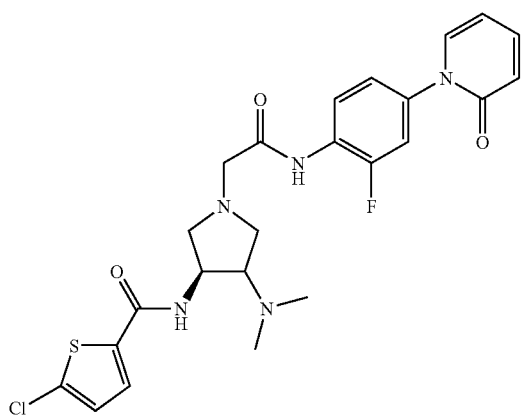

Example 34

In analogy to example 33 ((S)-1-{[2-fluoro-4-(2-oxo-2-pyridin-1-yl)-phenylcarbamoyl]-methyl}-4-oxo-pyrrolidin-3-yl)-amide (example 32.1) was reacted with 2,2-difluoro ethylamine to give 5-chloro-thiophene-2-carboxylic acid ((S)-4-(2,2-difluoro-ethylamino)-1-{[2-fluoro-4-(2-oxo-2-pyridin-1-yl)-phenylcarbamoyl]-methyl}-pyrrolidin-3-yl)-amide as light yellow amorphous solid. MS 552.3 ([M−H]$^−$)

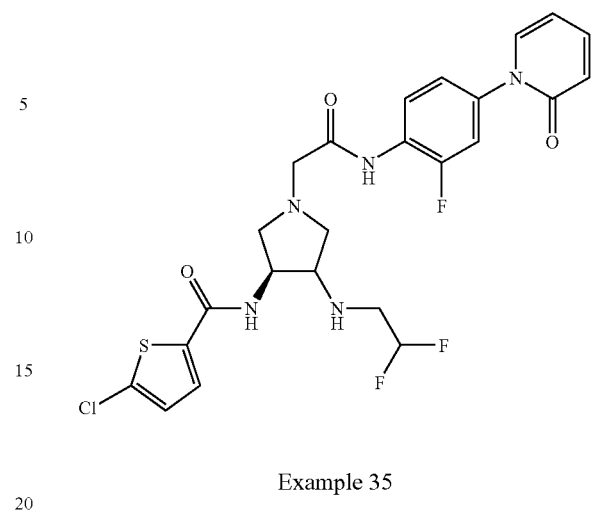

Example 35

35.1 Using the same procedure as described in example 32.1 (3S,4S)-3-[(5-chloro-thiophene-2-carbonyl)-amino]-4-hydroxy-pyrrolidine-1-carboxylic acid tert-butyl ester (example 22.4) was converted to (S)-3-[(5-chloro-thiophene-2-carbonyl)-amino]-4-oxo-pyrrolidine-1-carboxylic acid tert-butyl ester. Light yellow solid. MS 345.0 ([M+H]$^+$)

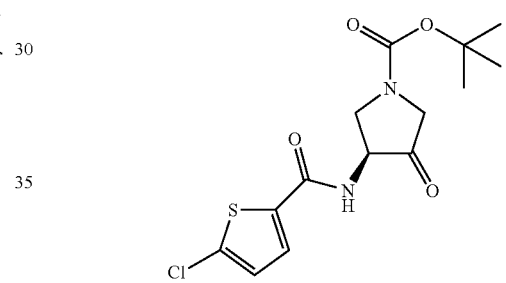

35.2 A solution of 500 mg (S)-3-[(5-chloro-thiophene-2-carbonyl)-amino]-4-oxo-pyrrolidine-1-carboxylic acid tert-butyl ester in 20 ml EtOH was treated with 155 mg ammonium chloride, 0.49 ml Hünig's base and 0.86 ml tetraisopropyl orthotitanate. The reaction mixture was stirred for 5 hrs at 40° C. Then it was cooled to 0° C., treated with 110 mg NaBH$_4$ and stirred at r.t. overnight. The mixture was diluted with EtOAc and washed with H$_2$O. The organic layer was dried over MgSO$_4$, filtered and concentrated. The crude product was purified by column chromatography (silica gel, gradient: CH$_2$Cl$_2$->CH$_2$Cl$_2$/MeOH 9:1) to give 180 mg (S)-3-amino-4-[(5-chloro-thiophene-2-carbonyl)-amino]-pyrrolidine-1-carboxylic acid tert-butyl ester as yellow solid. MS 344.3 ([M−H]$^−$)

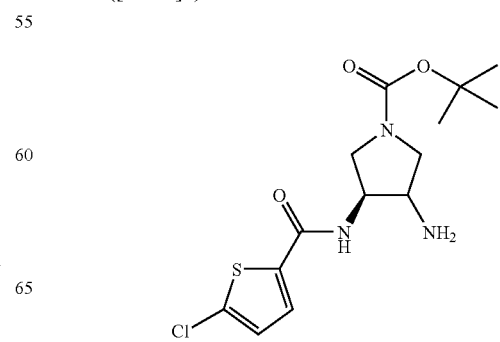

35.3 In analogy to example 20.2 (S)-3-amino-4-[(5-chloro-thiophene-2-carbonyl)-amino]-pyrrolidine-1-carboxylic acid tert-butyl ester was reacted with methane sulfonylchloride to give (S)-3-[(5-chloro-thiophene-2-carbonyl)-amino]-4-methanesulfonylamino-pyrrolidine-1-carboxylic acid tert-butyl ester. White solid. MS 424.0 ([M+H]$^+$)

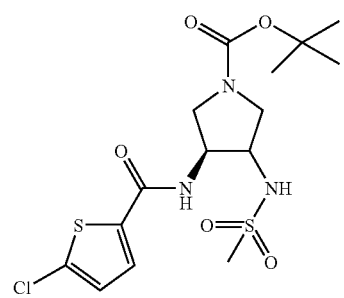

35.4 In analogy to examples 17.4 and 17.5 (S)-3-[(5-chloro-thiophene-2-carbonyl)-amino]-4-methanesulfonylamino-pyrrolidine-1-carboxylic acid tert-butyl ester was converted to 5-chloro-thiophene-2-carboxylic acid ((S)-1-{[2-fluoro-4-(2-oxo-2H-pyridin-1-yl)-phenylcarbamoyl]-methyl}-4-methanesulfonylamino-pyrrolidin-3-yl)-amide. Off-white solid. MS 568.2 ([M+H]$^+$)

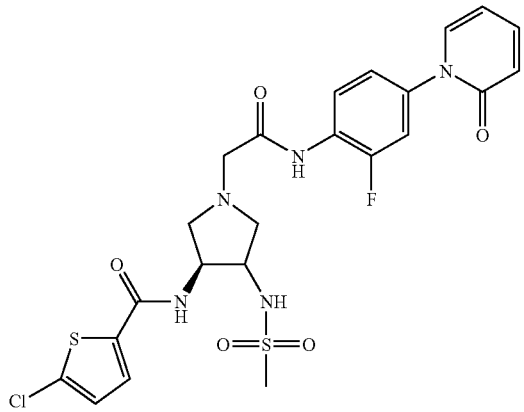

Example 36

In analogy to example 35.3 and 35.4 (S)-3-amino-4-[(5-chloro-thiophene-2-carbonyl)-amino]-pyrrolidine-1-carboxylic acid tert-butyl ester (example 35.2) was reacted with acetyl chloride and then converted to 5-chloro-thiophene-2-carboxylic acid ((S)-4-acetylamino-1-{[2-fluoro-4-(2-oxo-2H-pyridin-1-yl)-phenylcarbamoyl]-methyl}-pyrrolidin-3-yl)-amide. Off-white solid. MS 532.0 ([M+H]$^+$)

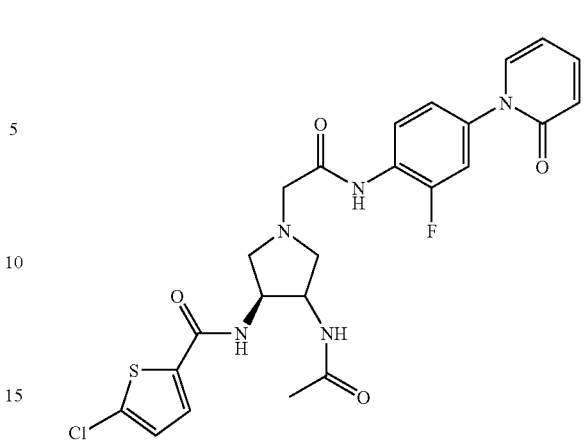

Example 37

37.1 To stirred, cooled (−78° C.) solution of 695 mg (3S, 4S)-3-azido-4-hydroxy-pyrrolidine-1-carboxylic acid tert-butyl ester (example 22.2) in 5 ml CH$_2$Cl$_2$ under an argon atmosphere were added 2.69 g bis(2-methoxyethyl)aminosulphur trifluoride (50% solution in THF). The dry ice bath was removed and the mixture was allowed to warm to r.t. and stirring was continued for 22 h. The mixture was poured into 10% aq. Na$_2$CO$_3$. The organic phase was washed with brine, dried (MgSO$_4$), filtered and concentrated. The crude product was purified by chromatography (silica gel; gradient: cyclohexane->cyclohexane/EtOAc 3:2) to give 424 mg (S)-3-azido-4-fluoro-pyrrolidine-1-carboxylic acid tert-butyl ester as light yellow oil. MS 409.0 ([M+H]$^+$)

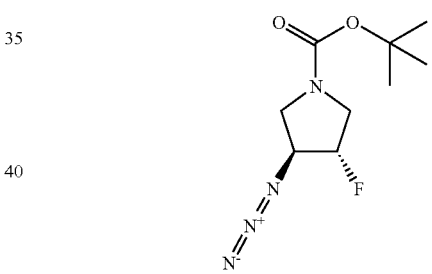

37.2 Using analogous procedures as described in examples 22.3-22.6 (S)-3-azido-4-fluoro-pyrrolidine-1-carboxylic acid tert-butyl ester was converted to 5-chloro-thiophene-2-carboxylic acid ((S)-4-fluoro-1-{[2-fluoro-4-(2-oxo-2H-pyridin-1-yl)-phenylcarba-moyl]-methyl}-pyrrolidin-3-yl)-amide. White solid. MS 493.3 ([M+H]$^+$)

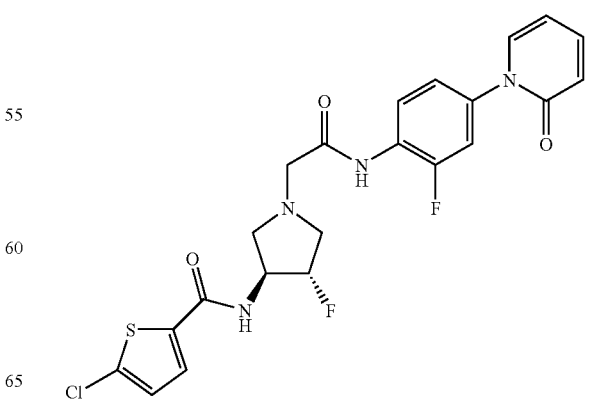

Example 38

38.1 A solution of 530 mg (3S,4S)-3-azido-4-hydroxy-pyrrolidine-1-carboxylic acid tert-butyl ester (example 22.2) in 5 ml pyridine was cooled to 0° C. under an argon atmosphere and treated with 664 mg 4-toluenesulfonyl chloride. The mixture was slowly warmed to room temperature and stirred for 6 hrs. The pyridine was distilled off. The residue was taken up in $CH_2Cl_2$ and 10% aq. $Na_2CO_3$. The organic phase was washed with $H_2O$ and brine, dried over $MgSO_4$, filtered and concentrated. The crude product was purified by column chromatography (silica gel, gradient: cyclohexane-> cyclohexane/EtOAc 7:3) to give 628 mg (3S,4S)-3-azido-4-(toluene-4-sulfonyloxy)-pyrrolidine-1-carboxylic acid tert-butyl ester as viscous yellow oil. MS 405.3 ([M+Na]$^+$)

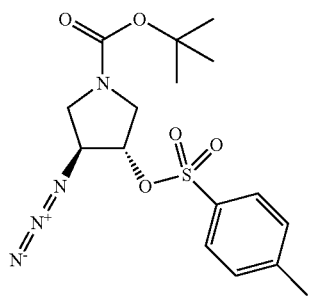

38.2 A solution of 440 mg (3S,4S)-3-azido-4-(toluene-4-sulfonyloxy)-pyrrolidine-1-carboxylic acid tert-butyl ester in 8.6 ml 1M tetrabutylammonium fluoride solution in THF was stirred overnight at r.t. The reaction mixture was concentrated. The crude product was isolated by column chromatography (silica gel, gradient: cyclohexane->cyclohexane/EtOAc 1:1) to give 150 mg (3S,4R)-3-azido-4-fluoro-pyrrolidine-1-carboxylic acid tert-butyl ester as colorless liquid. MS 230 ([M])

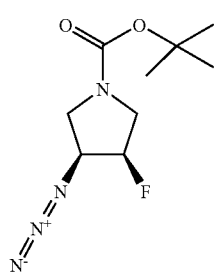

38.3 Using analogous procedures as described in examples 22.3-22.6 (3S,4R)-3-azido-4-fluoro-pyrrolidine-1-carboxylic acid tert-butyl ester was converted to 5-chloro-thiophene-2-carboxylic acid ((3S,4R)-4-fluoro-1-{[2-fluoro-4-(2-oxo-2-pyridin-1-yl)-phenylcarbamoyl]-methyl}-pyrrolidin-3-yl)-amide. White solid. MS493.4 ([M+H]$^+$)

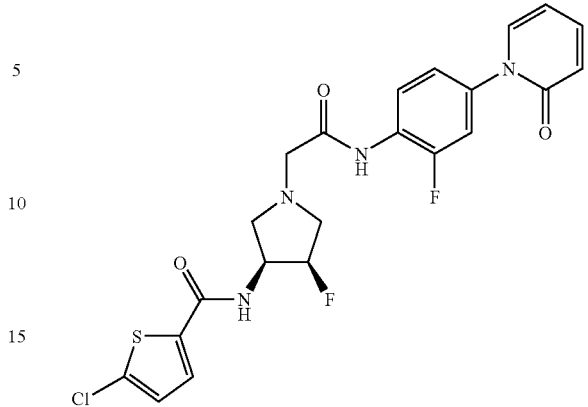

Example 39

39.1 Using general procedure A 5-chloro-thiophene-2-carboxylic acid ((3S,4S)-4-hydroxy-pyrrolidin-3-yl)-amide hydrochloride (example 22.5) was reacted with bromoacetic acid ethylester to give {(3S,4S)-3-[(5-chloro-thiophene-2-carbonyl)-amino]-4-hydroxy-pyrrolidin-1-yl}-acetic acid ethyl ester. Light yellow solid. MS 333.3 ([M+H]$^+$)

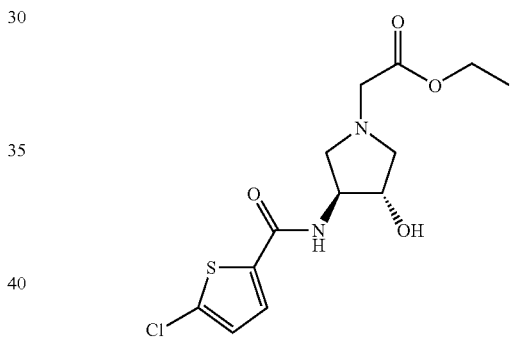

39.2 Using the same procedure as described in example 32.1 {(3S,4S)-3-[(5-chloro-thiophene-2-carbonyl)-amino]-4-hydroxy-pyrrolidin-1-yl}-acetic acid ethyl ester was converted to {(S)-3-[(5-chloro-thiophene-2-carbonyl)-amino]-4-oxo-pyrrolidin-1-yl}-acetic acid ethyl ester. Amorphous gum. MS 333.1 ([M+H]$^+$)

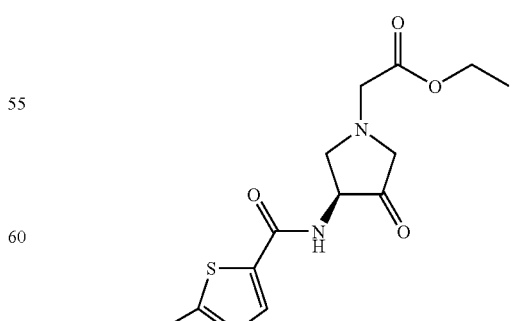

39.3 To a cooled (0° C.), stirred suspension of 44 mg potassium tert-butylate in 3 ml THF under an argon atmosphere were added 149 mg methyltriphenylphosphonium bromide. The yellow slurry was then stirred for 1 h 30, slowly warming up to room temperature. A solution of 100 mg {(S)-3-[(5-chloro-thiophene-2-carbonyl)-amino]-4-oxo-pyrrolidin-1-yl}-acetic acid ethyl ester in 2 ml THF was then added. The mixture was heated to reflux and stirred for 2 hrs. The mixture (dark brown slurry) was cooled to r.t., diluted with EtOAc, washed with sat. aq. $NH_4C_1$, $H_2O$ and brine, dried over $MgSO_4$, filtered and concentrated. The crude product was purified by column chromatography (silica gel, gradient: $CH_2Cl_2$->$CH_2Cl_2$/MeOH 95:5) to give 76 mg {(R)-3-[(5-chloro-thiophene-2-carbonyl)-amino]-4-methylene-pyrrolidin-1-yl}-acetic acid ethyl ester (contaminated with 43 w % triphenylphosphin oxide). Amorphous gum. MS 329.0 ([M+H]$^+$)

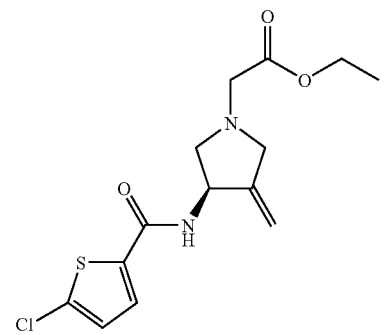

39.4 Using general procedure F {(R)-3-[(5-chloro-thiophene-2-carbonyl)-amino]-4-methylene-pyrrolidin-1-yl}-acetic acid ethyl ester was reacted with 1-(4-amino-3-fluoro-phenyl)-1H-pyridin-2-one (CAS 536747-52-1, prepared according to WO 2003045912) to give 5-chloro-thiophene-2-carboxylic acid ((R)-1-{[2-fluoro-4-(2-oxo-2H-pyridin-1-yl)-phenylcarbamoyl]-methyl}-4-methylene-pyrrolidin-3-yl)-amide. Yellow solid. MS 487.2 ([M+H]$^+$)

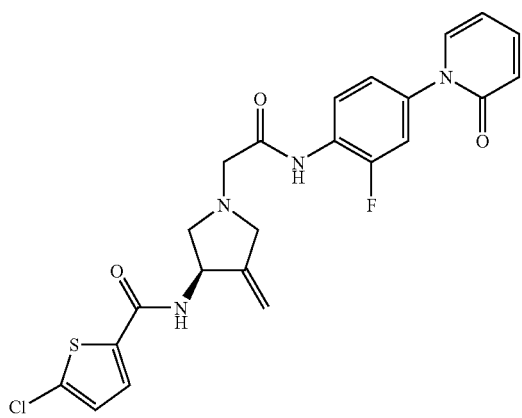

Example 40

40.1 (3R,4R)-Pyrrolidine-1,3,4-tricarboxylic acid 1-tert.-butyl ester 3-ethyl ester (CAS 595556-31-3 5 g; 17 mmol) was dissolved in toluene (50 ml), triethylamine (2.43 ml; 17 mmol) and diphenylphosphoryl azide (3.77 ml; 17 mmol) were added. The reaction mixture was stirred at 80° C. for 30 min. After that 2-(trimethylsilyl)ethanol (12.41 ml; 87 mmol) was added and the reaction mixture was stirred at 90° C. for 14 h. The reaction mixture was evaporated, dissolved in ethyl acetate and extracted with aqueous $Na_2CO_3$ and aqueous HCl (1N). The organic layers were combined and dried over $Na_2SO_4$. Flash chromatography over silica gel using DCM/MeOH/NH$_3$ as eluent yielded 4.6 g (65.6%) (3S,4R)-4-(2-trimethylsilanyl-ethoxycarbonylamino)-pyrrolidine-1,3-dicarboxylic acid 1-tert-butyl ester 3-ethyl ester. MS 403.5 [M+H$^+$].

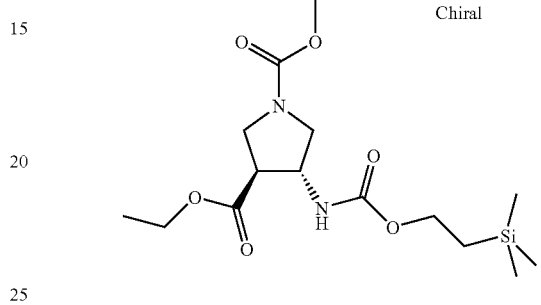

40.2 (3S,4R)-4-(2-Trimethylsilanylethoxycarbonylamino)-pyrrolidine-1,3-dicarboxylic acid 1-tert-butyl ester 3-ethyl ester (1.4 g; 3 mmol) is dissolved in acetonitrile (15 ml) and TBAF (1.372 g; 4 mmol) is added under an argon atmosphere. The mixture is stirred for 18 h at 50° C. 5-Chlorothiophene-2-carboxylic acid (1.272 g; 8 mmol) is dissolved in THF (10 ml), N-methyl morpholine (0.86 ml; 8 mmol) followed by isobutyl chloroformate (1.03 ml; 8 mmol) is added at 0° C. to this solution. After 30 min stirring at 25° C. this solution is added to the reaction mixture above. After 18 h at 25° C. additional 0.5 equivalents of activated 5-chloro-thiophene-2-carboxylic acid is added. The whole mixture is stirred for 3 d at 25° C., evaporated to dryness, dissolved in DCM/THF and washed with 1N aq. HCl solution, 10% aq. $Na_2CO_3$ solution. The organic phase is dried over $Na_2SO_4$. Flash chromatography over silica gel using DCM/MeOH/NH$_3$ as eluent yielded 0.522 g (37.2%) (3S,4R)-4-[(5-chloro-thiophene-2-carbonyl)-amino]-pyrrolidine-1,3-dicarboxylic acid 1-tert-butyl ester 3-ethyl ester. Light brown oil. MS 403.5 [M+H$^+$].

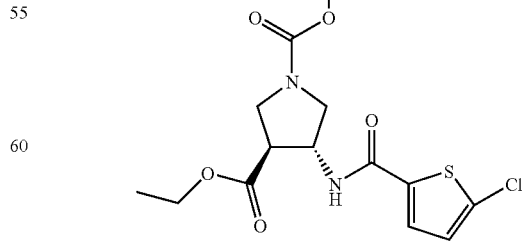

40.3 Using general procedure B (3S,4R)-4-[(5-Chloro-thiophene-2-carbonyl)-amino]-pyrrolidine-1,3-dicarboxylic acid 1-tert-butyl ester 3-ethyl ester was converted into (3S,4R)-4-[(5-chloro-thiophene-2-carbonyl)-amino]-pyrrolidine-3-carboxylic acid ethyl ester hydrochloride. Light yellow solid. MS 303.4 [M+H⁺].

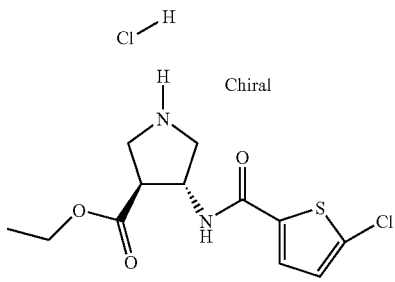

40.4 Using general procedure A with THF as solvent (3S,4R)-4-[(5-chloro-thiophene-2-carbonyl)-amino]-pyrrolidine-3-carboxylic acid ethyl ester hydrochloride was reacted with 2-bromo-[2-fluoro-4-(2-oxopyridin-1-yl)-phenyl]-acetamide to give (3S,4R)-4-[(5-chloro-thiophene-2-carbonyl)-amino]-1-{[2-fluoro-4-(2-oxo-2H-pyridin-1-yl)-phenyl-carbamoyl]-methyl}-pyrrolidine-3-carboxylic acid ethyl ester. Light brown solid. MS 547.2 [M+H⁺].

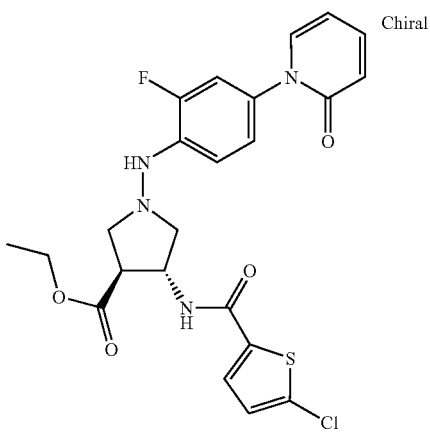

Example 41

(3S,4R)-4-[(5-Chloro-thiophene-2-carbonyl)-amino]-1-{[2-fluoro-4-(2-oxo-2H-pyridin-1-yl)-phenylcarbamoyl]-methyl}-pyrrolidine-3-carboxylic acid ethyl ester (example 40.4; 0.11 g) is dissolved in THF/water (1:1; 3 ml) and LiOH hydrate (9 mg) is added to the suspension. The mixture is stirred for 2 h at 25° C. The solvent is evaporated to dryness to obtain 0.102 g (95%) lithium (3S,4R)-4-[(5-chloro-thiophene-2-carbonyl)-amino]-1-{[2-fluoro-4-(2-oxo-2H-pyridin-1-yl)-phenylcarbamoyl]-methyl}-pyrrolidine-3-carboxylate. White solid. MS 519.3 [M+H⁺].

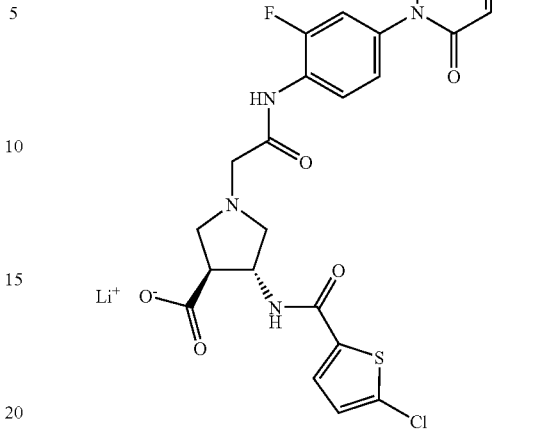

Example 42

Lithium (3S,4R)-4-[(5-chloro-thiophene-2-carbonyl)-amino]-1-{[2-fluoro-4-(2-oxo-2H-pyridin-1-yl)-phenylcarbamoyl]-methyl}-pyrrolidine-3-carboxylate (example 41; 0.09 g) is dissolved in THF/DMF (1:1; 3 ml) and CDI (0.083 g) is added. The mixture is stirred for 1 h at 25° C., after that 2-(methylamino)-ethanol (0.03 ml) is added. The reaction mixture is stirred for 18 h at 25° C. and evaporated to dryness followed by flash chromatography over silica gel using DCM/MeOH/NH₃ as eluent to yield 0.033 g (33.4%) (3S,4R)-4-[(5-chloro-thiophene-2-carbonyl)-amino]-1-{[2-fluoro-4-(2-oxo-2H-pyridin-1-yl)-phenylcarbamoyl]-methyl}-pyrrolidine-3-carboxylic acid (2-hydroxy-ethyl)-methyl-amide. White solid. MS 576.5 [M+H⁺].

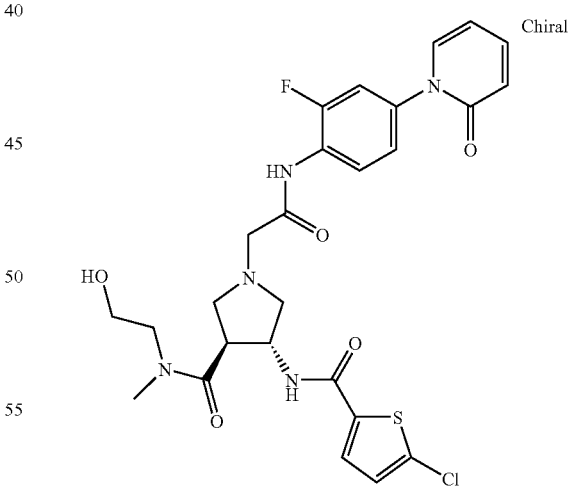

Example 43

The preparation of (3S,4R)-4-[(5-chloro-thiophene-2-carbonyl)-amino]-1-{[2-fluoro-4-(2-oxo-2H-pyridin-1-yl)-phenylcarbamoyl]-methyl}-pyrrolidine-3-carboxylic acid (2,2-difluoro-ethyl)-amide is analogous to example 42 using 2,2-difluoroethylamine. White solid. MS 582.3 [M+H⁺].

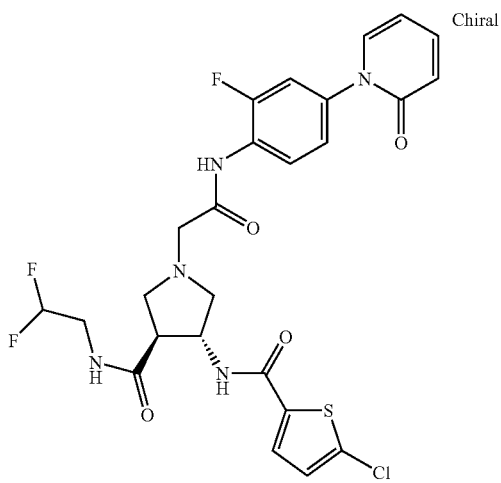

Example 44

(3S,4R)-4-[(5-chloro-thiophene-2-carbonyl)-amino]-1-{[2-fluoro-4-(2-oxo-2H-pyridin-1-yl)-phenylcarbamoyl]-methyl}-pyrrolidine-3-carboxylic acid ethyl ester (example 40.4; 1.2 g) is dissolved in ethanol (12 ml) under Ar-atmosphere. NaBH$_4$ (4 equivalents) is added and the mixture is stirred for 18 h at 25° C. After that additional NaBH$_4$ (5 equivalents) is added and the reaction mixture is stirred for further 24 h at 25° C. Further NaBH$_4$ (11 equivalents) is added and the reaction mixture is stirred for 72 h at 25° C. to give 80% conversion of the ester to the alcohol. After that the reaction mixture is evaporated to dryness followed by flash chromatography over silica gel using DCM/MeOH/NH$_3$ as eluent to yield 0.435 g (39.3%) 5-chloro-thiophene-2-carboxylic acid ((3R,4S)-1-{[2-fluoro-4-(2-oxo-2H-pyridin-1-yl)-phenylcarbamoyl]-methyl}-4-hydroxy-methyl-pyrrolidin-3-yl)-amide. Pale yellow solid. MS 505.3 [M+H$^+$].

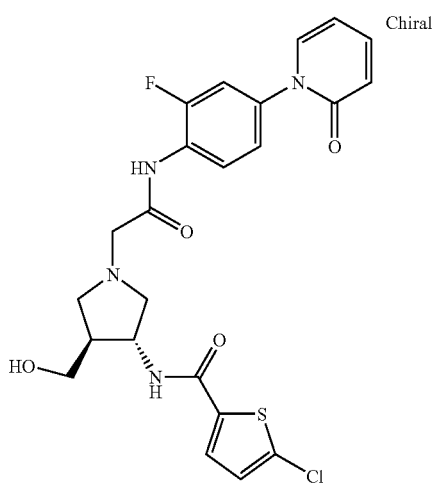

Example 45

5-Chloro-thiophene-2-carboxylic acid ((3R,4S)-1-{[2-fluoro-4-(2-oxo-2H-pyridin-1-yl)-phenylcarbamoyl]-methyl}-4-hydroxymethyl-pyrrolidin-3-yl)-amide (example 44; 2.0 g) is dissolved in dichloromethane (20 ml) under an argon atmosphere. Pyridine (0.48 ml) is dropped to this solution followed by mesylchloride (0.46 ml) at 0° C. The reaction mixture is stirred at 0° C. for 1 h. After that the reaction mixture is stirred at 25° C. for 48 h until conversion is complete. The reaction mixture is treated with SiO$_2$ and evaporated to dryness followed by flash chromatography over silica gel using DCM/MeOH/NH$_3$ as eluent to yield 1.75 g (75.8%) of methanesulfonic acid (3S,4R)-4-[(5-chloro-thiophene-2-carbonyl)-amino]-1-{[2-fluoro-4-(2-oxo-2H-pyridin-1-yl)-phenylcarbamoyl]-methyl}-pyrrolidin-3-ylmethyl ester. Off-white solid. MS 583.2 [M+H$^+$].

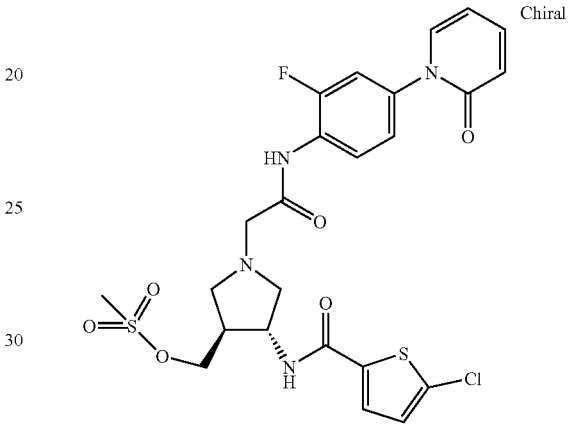

Example 46

Methanesulfonic acid (3S,4R)-4-[(5-chloro-thiophene-2-carbonyl)-amino]-1-{[2-fluoro-4-(2-oxo-2H-pyridin-1-yl)-phenylcarbamoyl]-methyl}-pyrrolidin-3-ylmethyl ester (example 45; 50 mg) and azettidine (24 mg) are dissolved in DMF (1 ml) in a sealed tube. The reaction mixture is stirred for 72 h at 25° C. and purified with preparative HPLC to yield 16 mg (34.3%) 5-chloro-thiophene-2-carboxylic acid ((3R, 4S)-4-azetidin-1-ylmethyl-1-{[2-fluoro-4-(2-oxo-2H-pyridin-1-yl)-phenylcarbamoyl]-methyl}-pyrrolidin-3-yl)-amide diformiate as colorless gum. MS 544.3 [M+H$^+$].

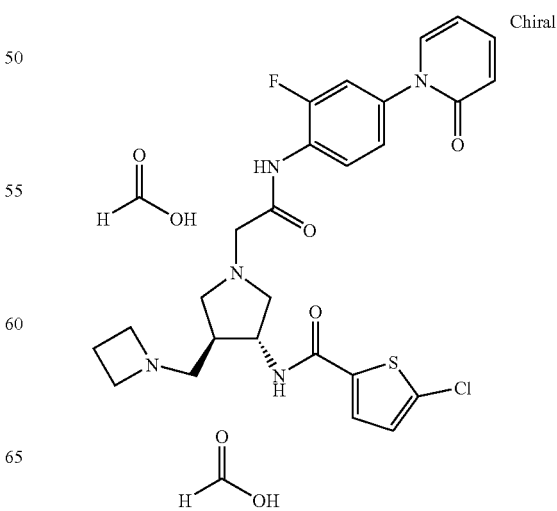

Example 47

5-Chloro-thiophene-2-carboxylic acid ((3R,4S)-4-cyclopropylaminomethyl-1-{[2-fluoro-4-(2-oxo-2H-pyridin-1-yl)-phenylcarbamoyl]-methyl}-pyrrolidin-3-yl)-amide formiate was prepared according to the methods described for example 46 to yield 28 mg (30.0%) as light yellow solid. MS 544.3 [M+H$^+$].

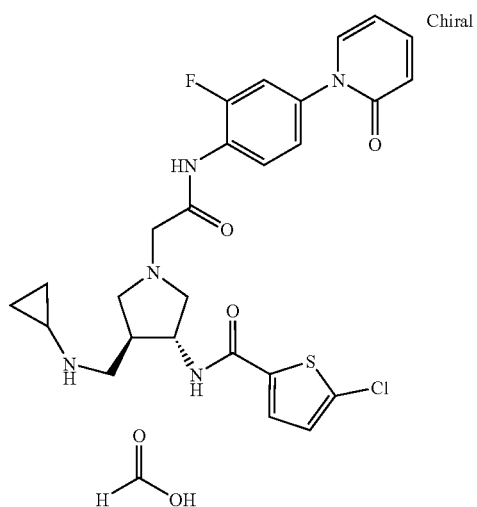

Example 48

5-Chloro-thiophene-2-carboxylic acid ((3R,4S)-4-cyclobutylaminomethyl-1-{[2-fluoro-4-(2-oxo-2H-pyridin-1-yl)-phenylcarbamoyl]-methyl}-pyrrolidin-3-yl)-amide diformiate was prepared according to the methods described for example 46 to yield 39 mg (40.7%) as colorless amorphous solid. MS 558.2 [M+H$^+$].

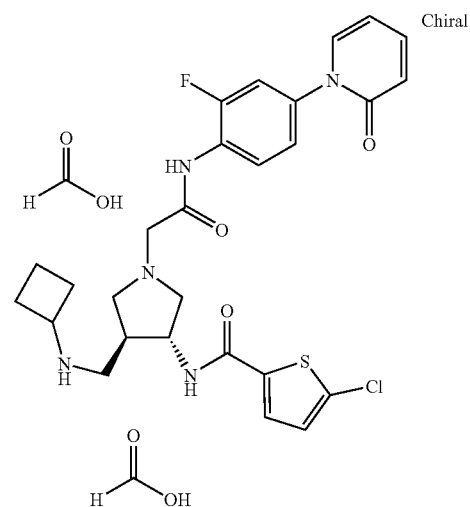

Example 49

5-Chloro-thiophene-2-carboxylic acid ((3R,4S)-4-[(cyclopropylmethyl-amino)-methyl]-1-{[2-fluoro-4-(2-oxo-2H-pyridin-1-yl)-phenylcarbamoyl]-methyl}-pyrrolidin-3-yl)-amide formiate was prepared according to the methods described for example 46 to yield 39 mg (40.7%) as light yellow amorphous solid. MS 558.2 [M+H$^+$].

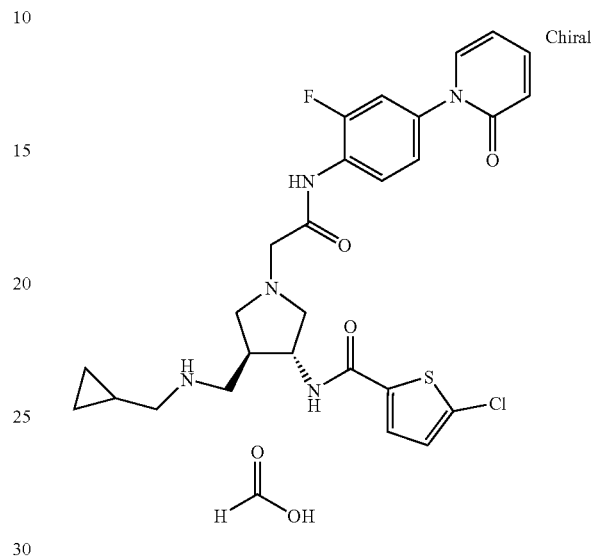

Example 50

(3R,4R)-4-[2-Fluoro-4-(2-oxo-2H-pyridin-1-yl)-phenylcarbamoyl]-pyrrolidine-3-carboxylic acid ethyl ester hydrochloride (0.315 g; synthesis described in EP04101265.9 example 28 step 3) is suspended in acetonitrile (10 ml) and K$_2$CO$_3$ (0.425 g) is added as solid. 2-Bromo-N-(5-chloro-2-pyridinyl)-acetamide (0.23 g) is added and the reaction mixture is stirred at 25° C. for 18 h. After that the mixture is heated for 3 h to 80° C., cooled to 25° C. and filtered. The filtrate is evaporated to dryness followed by flash chromatography over silica gel using DCM/MeOH/NH$_3$ as eluent to yield 0.203 g (46.3%) (3R,4R)-1-[(5-chloro-pyridin-2-ylcarbamoyl)-methyl]-4-[2-fluoro-4-(2-oxo-2H-pyridin-1-yl)-phenylcarbamoyl]-pyrrolidine-3-carboxylic acid ethyl ester. White solid. MS 542.3 [M+H$^+$].

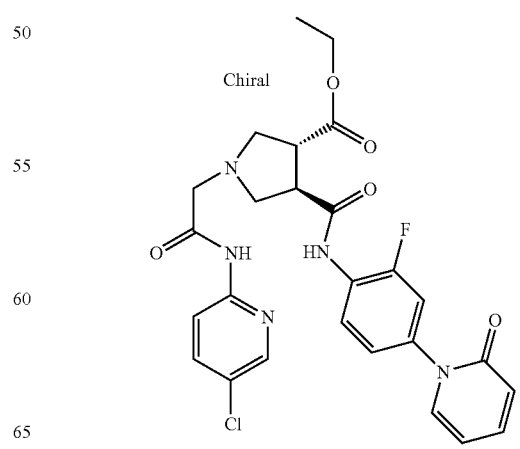

Example 51

Lithium (3R,4R)-1-[(5-chloro-pyridin-2-ylcarbamoyl)-methyl]-4-[2-fluoro-4-(2-oxo-2H-pyridin-1-yl)-phenylcarbamoyl]-pyrrolidine-3-carboxylate is prepared from (3R,4R)-1-[(5-chloro-pyridin-2-ylcarbamoyl)-methyl]-4-[2-fluoro-4-(2-oxo-2H-pyridin-1-yl)-phenylcarbamoyl]-pyrrolidine-3-carboxylic acid ethyl ester according to example 41. White solid. MS 514.3 [M+H$^+$].

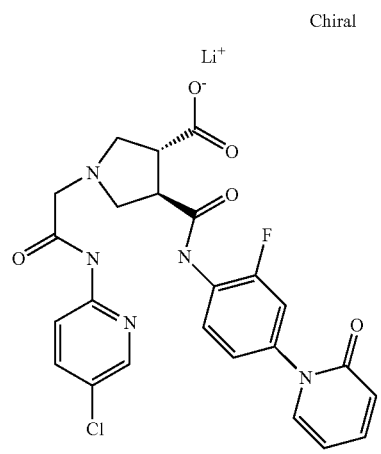

Example 52 (Reference)

1-[(5-Chloro-pyridin-2-yl-carbamoyl)-methyl]-pyrrolidine-3-carboxylic acid[2-fluoro-4-(2-oxo-2H-pyridin-1-yl)-phenyl]-amide is prepared from commercially available 3-carboxy-1-Boc-pyrrolidine according to general methods A, B and C to yield 0.054 mg (14%) as light brown solid. MS 470.4 [M+H$^+$].

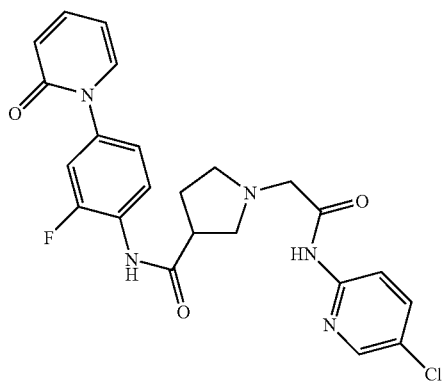

Example 53 (Reference)

N-{(R)-1-[(5-chloro-pyridin-2-ylcarbamoyl)-methyl]-pyrrolidin-3-yl}-2-fluoro-4-(2-oxo-2H-pyridin-1-yl)-benzamide is prepared from commercially available (3R)-3-(tert-butoxycarbonylamino)pyrrolidine according to general methods A, B and D to yield 0.054 mg (14%) as light brown solid. MS 470.4 [M+H$^+$].

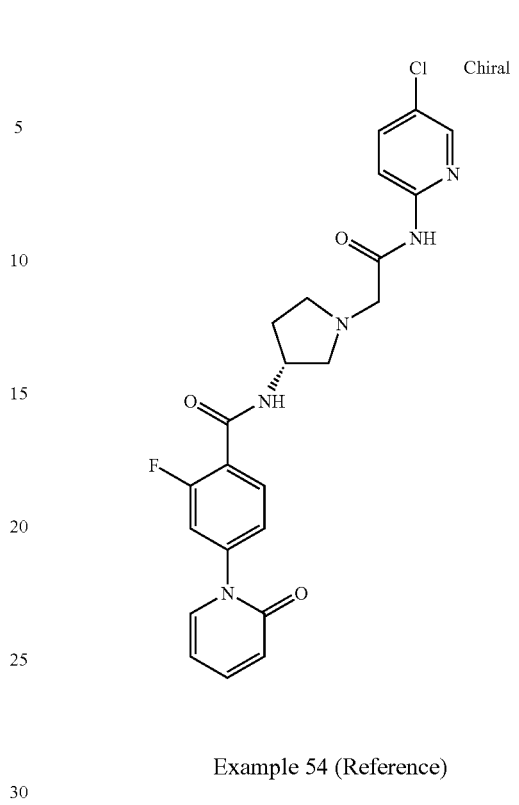

Example 54 (Reference)

50.1 Using general procedure E, (R)-3-aminomethyl-1-N-tert-butoxycarbonyl-pyrrolidine was coupled with 5-chlorothiophene-2-carboxylic acid to give (R)-3-{[(5-chlorothiophene-2-carbonyl)-amino]-methyl}-pyrrolidine-1-carboxylic acid tert-butyl ester. Brown oil. MS 345.0 ([M+H]$^+$)

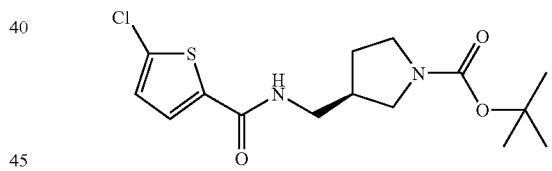

50.2 Using general procedure C, (R)-3-{[(5-chlorothiophene-2-carbonyl)-amino]-methyl}-pyrrolidine-1-carboxylic acid tert-butyl ester was converted to 5-chlorothiophene-2-carboxylic acid ((S)-1-pyrrolidin-3-ylmethyl)-amide trifluoro acetate. Pale brown oil. MS 245.4 ([M+H]$^+$)

50.3 Using general method G, 1-(4-amino-3-fluoro-phenyl)-1H-pyridin-2-one (prepared according to WO 2003045912) was activated with 4-nitrophenyl chloroformate to give [2-fluoro-4-(2-oxo-2H-pyridin-1-yl)-phenyl]-carbamic acid 4-nitro-phenyl ester. Pale pink solid.

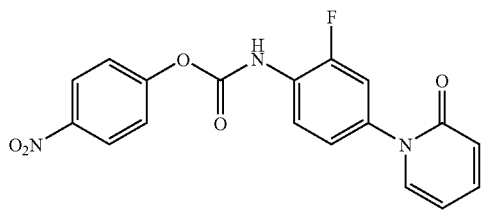

50.4 Using general method H, 5-chloro-thiophene-2-carboxylic acid ((S)-1-pyrrolidin-3-ylmethyl)-amide trifluoroacetate was reacted with [2-fluoro-4-(2-oxo-2H-pyridin-1-yl)-phenyl]-carbamic acid 4-nitro-phenyl ester to give (R)-3-{[(5-chloro-thiophene-2-carbonyl)-amino]-methyl}-pyrrolidine-1-carboxylic acid[2-fluoro-4-(2-oxo-2H-pyridin-1-yl)-phenyl]-amide. White solid. MS 475.0 ([M+H]$^+$)

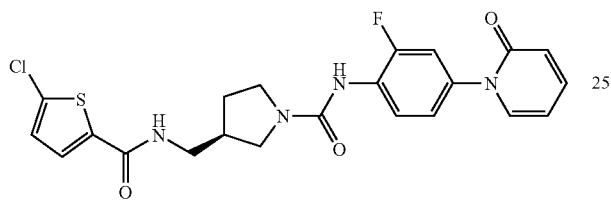

Example 55 (Reference)

The enantiomer (R)-3-{[(5-chloro-thiophene-2-carbonyl)-amino]-methyl}-pyrrolidine-1-carboxylic acid[2-fluoro-4-(2-oxo-2H-pyridin-1-yl)-phenyl]-amide was prepared according to examples 54.1-54.4 starting with (R)-3-aminomethyl-1-N-tert-butoxycarbonyl-pyrrolidine. Pale yellow solid. MS 475.0 ([M+H]$^+$)

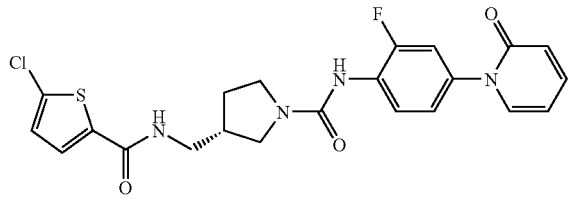

Example 56 (Reference)

56.1 Using general procedure E, (R)-3-aminomethyl-1-N-tert-butoxycarbonyl-pyrrolidine was coupled with 5-bromothiophene-2-carboxylic acid to give (R)-3-{[(5-bromo-thiophene-2-carbonyl)-amino]-methyl}-pyrrolidine-1-carboxylic acid tert-butyl ester. Yellow oil. MS 389.0 ([M+H]$^+$)

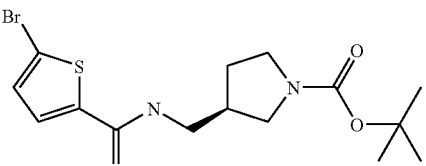

56.2 Using general procedure C, (R)-3-{[(5-bromo-thiophene-2-carbonyl)-amino]-methyl}-pyrrolidine-1-carboxylic acid tert-butyl ester was converted to 5-bromo-thiophene-2-carboxylic acid ((S)-1-pyrrolidin-3-ylmethyl)-amide trifluoroacetate. Yellow oil. MS 288.9 ([M+H]$^+$)

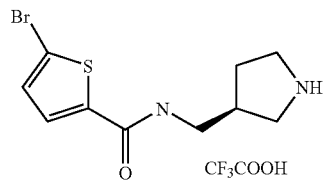

56.3 Using general method H. 5-bromo-thiophene-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-{[(5-bromo-thiophene-2-carbonyl)-amino]-methyl}-pyrrolidine-1-carboxylic acid[2-fluoro-4-(2-oxo-2H-pyridin-1-yl)-phenyl]-amide. White solid. MS 521.3 ([M+H]$^+$)

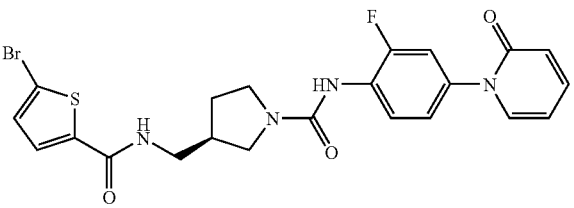

Example 57 (Reference)

57.1 Using general procedure E, (R)-3-aminomethyl-1-N-tert-butoxycarbonyl-pyrrolidine was coupled with 5-bromo-4-methyl-thiophene-2-carboxylic acid (prepared according to M. Nemec et al., Collection of Czechoslovak Chemical Communications, 1974, 39, 3527) to give (R)-3-{[(5-bromo-4-methyl-thiophene-2-carbonyl)-amino]-methyl}-pyrrolidine-1-carboxylic acid tert-butyl ester. White solid. MS 403.3 ([M−H]$^-$)

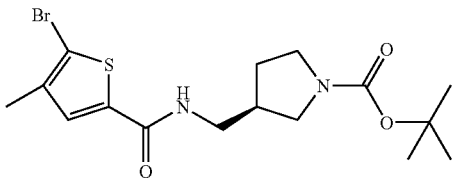

57.2 Using general procedure C, (R)-3-{[(5-bromo-4-methyl-thiophene-2-carbonyl)-amino]-methyl}-pyrrolidine-1-carboxylic acid tert-butyl ester was converted to 5-bromo-4-methyl-thiophene-2-carboxylic acid ((S)-1-pyrrolidin-3-ylmethyl)-amide trifluoro acetate. Colorless oil. MS 301.0 ([M−H]⁻)

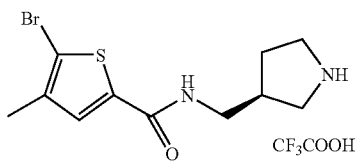

57.3 Using general method H, 5-bromo-4-methyl-thiophene-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-{[(5-bromo-4-methyl-thiophene-2-carbonyl)-amino]-methyl}-pyrrolidine-1-carboxylic acid[2-fluoro-4-(2-oxo-2H-pyridin-1-yl)-phenyl]-amide. White solid. MS 530.8 ([M−H]⁻)

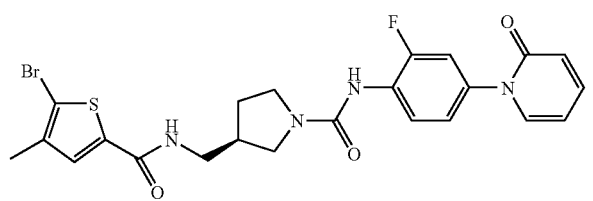

Example 58 (Reference)

58.1 Using general procedure E, (R)-3-aminomethyl-1-N-tert-butoxycarbonyl-pyrrolidine was coupled with 4,5-dibromothiophene-2-carboxylic acid to give (R)-3-{[(4,5-dibromo-thiophene-2-carbonyl)-amino]-methyl}-pyrrolidine-1-carboxylic acid tert-butyl ester. White solid. MS 466.9 ([M−H]⁻)

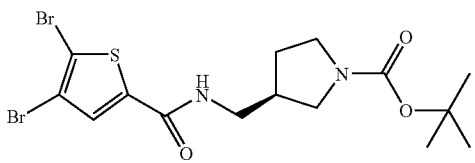

58.2 Using general procedure C, (R)-3-{[(4,5-dibromo-thiophene-2-carbonyl)-amino]-methyl}-pyrrolidine-1-carboxylic acid tert-butyl ester was converted to 4,5-dibromo-thiophene-2-carboxylic acid ((S)-1-pyrrolidin-3-ylmethyl)-amide trifluoroacetate. Pale yellow oil. MS 349.9 ([M+H]⁺)

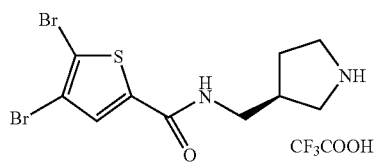

58.3 Using general method H, 4,5-dibromo-thiophene-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-{[(4,5-dibromo-thiophene-2-carbonyl)-amino]-methyl}-pyrrolidine-1-carboxylic acid[2-fluoro-4-(2-oxo-2H-pyridin-1-yl)-phenyl]-amide. Pale yellow solid. MS 598.8 ([M+H]⁺)

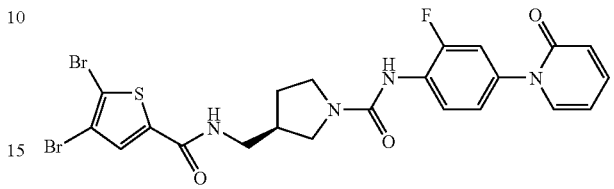

Example 59 (Reference)

59.1 Using general procedure E, (R)-3-aminomethyl-1-N-tert-butoxycarbonyl-pyrrolidine was coupled with 5-bromo-furan-2-carboxylic acid to give (R)-3-{[(5-bromo-furan-2-carbonyl)-amino]-methyl}-pyrrolidine-1-carboxylic acid tert-butyl ester. Pale yellow solid. MS373.1 ([M−H]⁻)

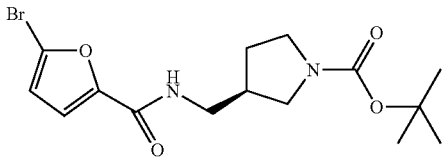

59.2 Using general procedure C, (R)-3-{[(5-bromo-furan-2-carbonyl)-amino]-methyl}-pyrrolidine-1-carboxylic acid tert-butyl ester was converted to 5-bromo-furan-2-carboxylic acid ((S)-1-pyrrolidin-3-ylmethyl)-amide trifluoro acetate. Orange oil. MS 273.1 ([M+H]⁺) Br

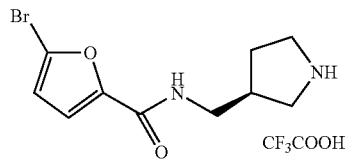

59.3 Using general method H, 5-bromo-furan-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-{[(5-bromo-furan-2-carbonyl)-amino]-methyl}-pyrrolidine-1-carboxylic acid[2-fluoro-4-(2-oxo-2H-pyridin-1-yl)-phenyl]-amide. White solid. MS 504.9 ([M+H]⁺)

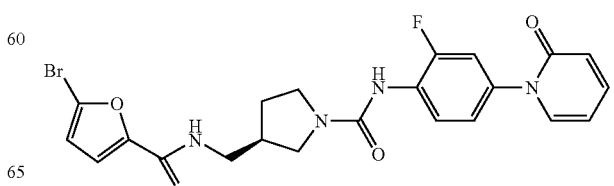

Example 60 (Reference)

60.1 Using general procedure E, (R)-3-aminomethyl-1-N-tert-butoxycarbonyl-pyrrolidine was coupled with 4,5-dibromo-1H-pyrrole-2-carboxylic acid to give (R)-3-{[(4,5-dibromo-1H-pyrrole-2-carbonyl)-amino]-methyl}-pyrrolidine-1-carboxylic acid tert-butyl ester. Pale yellow solid. MS449.9 ([M−H]⁻)

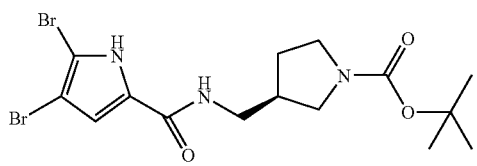

60.2 Using general procedure C, (R)-3-{[(4,5-dibromo-1H-pyrrole-2-carbonyl)-amino]-methyl}-pyrrolidine-1-carboxylic acid tert-butyl ester was converted to 4,5-dibromo-1H-pyrrole-2-carboxylic acid ((S)-1-pyrrolidin-3-ylmethyl)-amide trifluoroacetate. Red oil. MS 349.9 ([M−H]⁻)

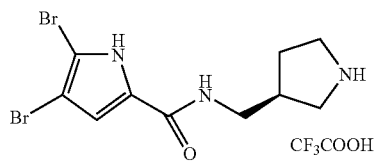

60.3 Using general method H, 4,5-dibromo-1H-pyrrole-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give 4,5-dibromo-1H-pyrrole-2-carboxylic acid {(R)-1-[2-fluoro-4-(2-oxo-2H-pyridin-1-yl)-phenylcarbamoyl]-pyrrolidin-3-ylmethyl}-amide. White solid. MS 582.1 ([M+H]⁺)

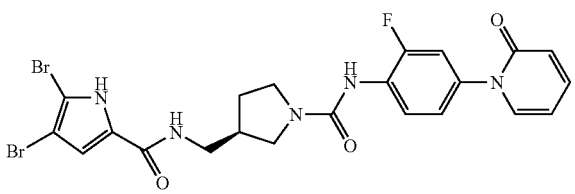

Example 61 (Reference)

61.1 Using general procedure E, (R)-3-aminomethyl-1-N-tert-butoxycarbonyl-pyrrolidine was coupled with 2-chloro-thiazole-4-carboxylic acid (prepared according to R. Walsh et al. Chimica Therapeutica, 1973, 8, 199) to give (R)-3-{[(2-chloro-thiazole-4-carbonyl)-amino]-methyl}-pyrrolidine-1-carboxylic acid tert-butyl ester. White solid. MS 343.9 ([M−H]⁻)

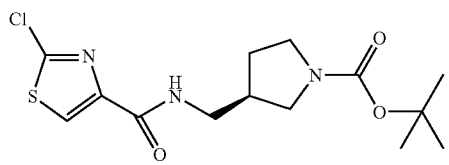

61.2 Using general procedure C, (R)-3-{[(2-chloro-thiazole-4-carbonyl)-amino]-methyl}-pyrrolidine-1-carboxylic acid tert-butyl ester was converted to 2-chloro-thiazole-4-carboxylic acid ((S)-1-pyrrolidin-3-ylmethyl)-amide trifluoro acetate. Pale yellow oil. MS 246.1 ([M+H]⁺)

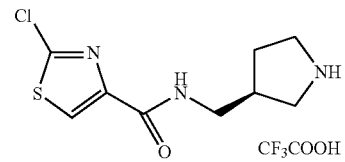

61.3 Using general method H, 2-chloro-thiazole-4-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give 2-chloro-thiazole-4-carboxylic acid {(R)-1-[2-fluoro-4-(2-oxo-2H-pyridin-1-yl)-phenylcarbamoyl]-pyrrolidin-3-ylmethyl}-amide. White solid. MS 476.0 ([M+H]⁺)

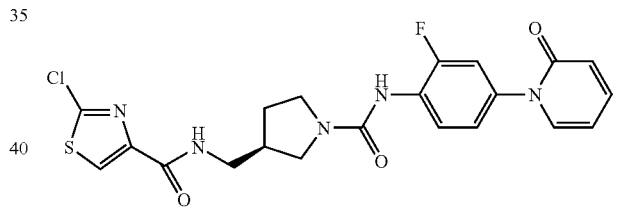

Example 62 (Reference)

62.1 Using general procedure E, (R)-3-aminomethyl-1-N-tert-butoxycarbonyl-pyrrolidine was coupled with 4-chloro-benzoic acid to give (R)-3-[(4-chloro-benzoylamino)-methyl]-pyrrolidine-1-carboxylic acid tert-butyl ester. Yellow oil. MS 339.3 ([M+H]⁺)

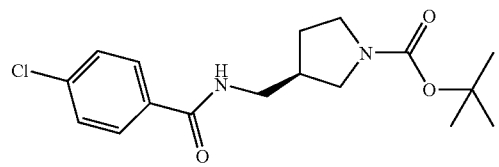

62.2 Using general procedure C, (R)-3-[(4-chloro-benzoylamino)-methyl]-pyrrolidine-1-carboxylic acid tert-butyl ester was converted to 4-chloro-N—(S)-1-pyrrolidin-3-ylmethyl-benzamide trifluoro acetate. Yellow oil. MS 239.3 ([M+H]⁺)

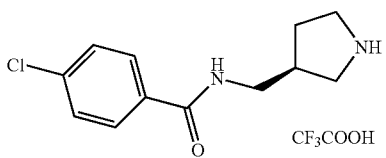

62.3 Using general method H, 4-chloro-N—(S)-1-pyrrolidin-3-ylmethyl-benzamide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-[(4-chloro-benzoylamino)-methyl]-pyrrolidine-1-carboxylic acid[2-fluoro-4-(2-oxo-2H-pyridin-1-yl)-phenyl]-amide. White solid. MS 469.0 ([M+H]$^+$)

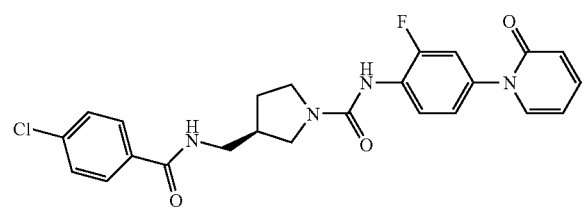

Example 63 (Reference)

63.1 Using general procedure E, (R)-3-aminomethyl-1-N-tert-butoxycarbonyl-pyrrolidine was coupled with 6-chloro-nicotinic acid to give (R)-3-{[(6-chloro-pyridine-3-carbonyl)-amino]-methyl}-pyrrolidine-1-carboxylic acid tert-butyl ester. Yellow oil. MS 340.1 ([M+H]$^+$)

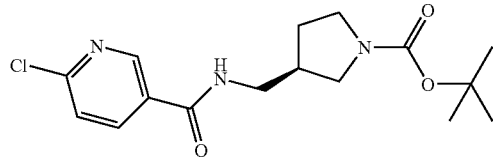

63.2 Using general procedure C, (R)-3-{[(6-chloro-pyridine-3-carbonyl)-amino]-methyl}-pyrrolidine-1-carboxylic acid tert-butyl ester was converted to 6-chloro-N—(S)-1-pyrrolidin-3-ylmethyl-nicotinamide trifluoro acetate. Yellow oil. MS 240.3 ([M+H]$^+$)

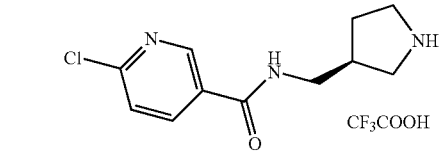

63.3 Using general method H, 6-chloro-N—(S)-1-pyrrolidin-3-ylmethyl-nicotinamide trifluoro acetate was reacted with [2-fluoro-4-(2-oxo-2H-pyridin-1-yl)-phenyl]-carbamic acid 4-nitro-phenyl ester (prepared according to example 54.3) to give 6-chloro-N-{(R)-1-[2-fluoro-4-(2-oxo-2H-pyridin-1-yl)-phenylcarbamoyl]-pyrrolidin-3-ylmethyl}-nicotinamide. White solid. MS 470.1 ([M+H]$^+$)

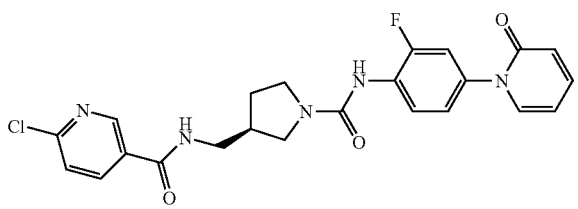

Example 64 (Reference)

64.1 Using general procedure E, (R)-3-aminomethyl-1-N-tert-butoxycarbonyl-pyrrolidine was coupled with 4-methoxy-benzoic acid to give (R)-3-[(4-methoxy-benzoylamino)-methyl]-pyrrolidine-1-carboxylic acid tert-butyl ester. Yellow oil. MS 335.1 ([M+H]$^+$)

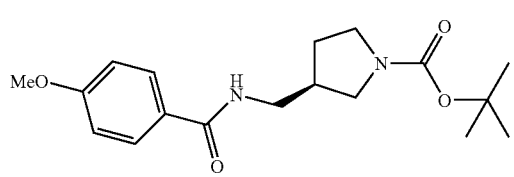

64.2 Using general procedure C, (R)-3-[(4-methoxy-benzoylamino)-methyl]-pyrrolidine-1-carboxylic acid tert-butyl ester was converted to 4-methoxy-N—(S)-1-pyrrolidin-3-ylmethyl-benzamide trifluoro acetate. Yellow oil. MS 235.1 ([M+H]$^+$)

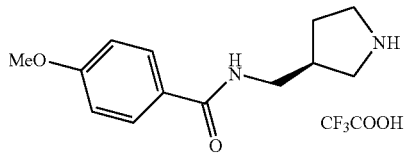

64.3 Using general method H, 4-methoxy-N—(S)-1-pyrrolidin-3-ylmethyl-benzamide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-[(4-methoxy-benzoylamino)-methyl]-pyrrolidine-1-carboxylic acid[2-fluoro-4-(2-oxo-2H-pyridin-1-yl)-phenyl]-amide. White solid. MS 465.0 ([M+H]$^+$)

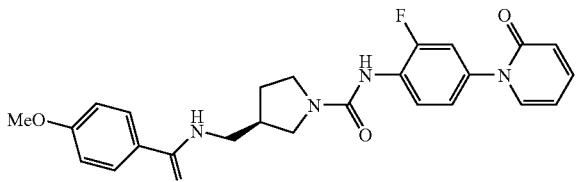

Example 65 (Reference)

65.1 Using general procedure E, (R)-3-aminomethyl-1-N-tert-butoxycarbonyl-pyrrolidine was coupled with 6-chloro-benzo[b]thiophene-2-carboxylic acid (prepared according to WO 2001007436) to give (R)-3-{[(6-chloro-benzo[b]thiophene-2-carbonyl)-amino]-methyl}-pyrrolidine-1-carboxylic acid tert-butyl ester. White solid. MS 392.9 ([M−H]⁻)

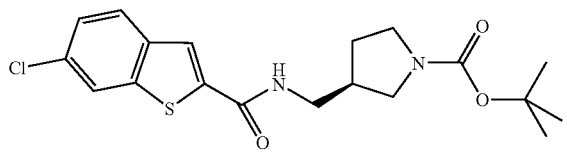

65.2 Using general procedure C, (R)-3-{[(6-chloro-benzo[b]thiophene-2-carbonyl)-amino]-methyl}-pyrrolidine-1-carboxylic acid tert-butyl ester was converted to 6-chloro-benzo[b]thiophene-2-carboxylic acid ((S)-1-pyrrolidin-3-ylmethyl)-amide trifluoro acetate. Colorless oil. MS 293.1 ([M−H]⁻)

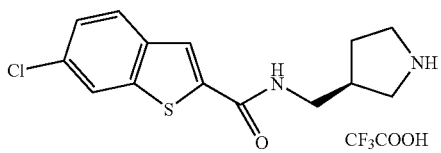

65.3 Using general method H, 6-chloro-benzo[b]thiophene-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-{[(6-chloro-benzo[b]thiophene-2-carbonyl)-amino]-methyl}-pyrrolidine-1-carboxylic acid[2-fluoro-4-(2-oxo-2H-pyridin-1-yl)-phenyl]-amide. White solid. MS 523.2 ([M−H]⁻)

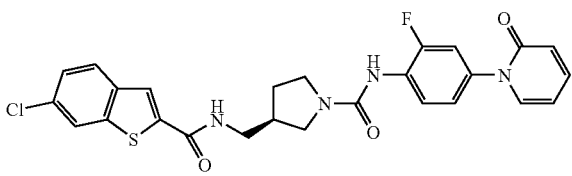

Example 66 (Reference)

66.1 Using general procedure E, (R)-3-aminomethyl-1-N-tert-butoxycarbonyl-pyrrolidine was coupled with 5-chloro-benzo[b]thiophene-2-carboxylic acid to give (R)-3-{[(5-chloro-benzo[b]thiophene-2-carbonyl)-amino]-methyl}-pyrrolidine-1-carboxylic acid tert-butyl ester. White solid. MS 392.9 ([M−H]⁻)

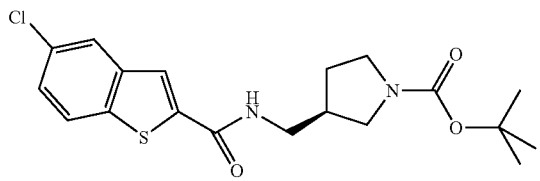

66.2 Using general procedure C, (R)-3-{[(5-chloro-benzo[b]thiophene-2-carbonyl)-amino]-methyl}-pyrrolidine-1-carboxylic acid tert-butyl ester was converted to 5-chloro-benzo[b]thiophene-2-carboxylic acid ((S)-1-pyrrolidin-3-ylmethyl)-amide trifluoro acetate. Pale yellow oil. MS 293.0 ([M−H]⁻)

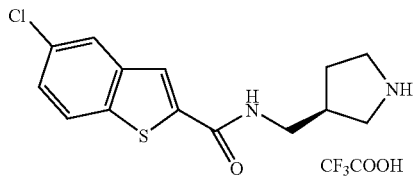

66.3 Using general method H, 5-chloro-benzo[b]thiophene-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-{[(5-chloro-benzo[b]thiophene-2-carbonyl)-amino]-methyl}-pyrrolidine-1-carboxylic acid[2-fluoro-4-(2-oxo-2H-pyridin-1-yl)-phenyl]-amide. Pale yellow solid. MS 523.0 ([M−H]⁻)

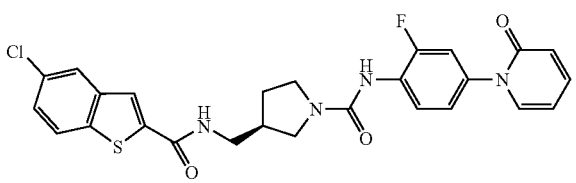

Example 67 (Reference)

67.1 Using general procedure E, (R)-3-aminomethyl-1-N-tert-butoxycarbonyl-pyrrolidine was coupled with 5-chloro-benzofuran-2-carboxylic acid to give (R)-3-{[(5-chloro-benzofuran-2-carbonyl)-amino]-methyl}-pyrrolidine-1-carboxylic acid tert-butyl ester. White solid. MS377.3 ([M−H]⁻)

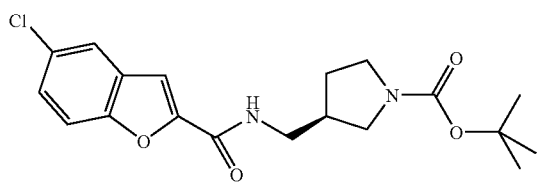

67.2 Using general procedure C, (R)-3-{[(5-chloro-benzofuran-2-carbonyl)-amino]-methyl}-pyrrolidine-1-carboxylic acid tert-butyl ester was converted to 5-chloro-benzofuran-2-carboxylic acid ((S)-1-pyrrolidin-3-ylmethyl)-amide trifluoro acetate. Pale yellow oil. MS 277.1 ([M−H]⁻)

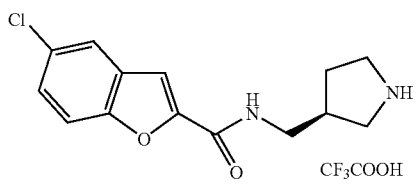

67.3 Using general method H, 5-chloro-benzofuran-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-{[(5-chloro-benzofuran-2-carbonyl)-amino]-methyl}-pyrrolidine-1-carboxylic acid[2-fluoro-4-(2-oxo-2H-pyridin-1-yl)-phenyl]-amide. Pale yellow solid. MS 507.0 ([M−H]⁻)

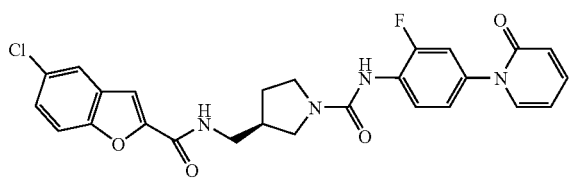

Example 68 (Reference)

68.1 Using general procedure E, (R)-3-aminomethyl-1-N-tert-butoxycarbonyl-pyrrolidine was coupled with 6-chloro-1H-indole-2-carboxylic acid to give (R)-3-{[(6-chloro-1H-indole-2-carbonyl)-amino]-methyl}-pyrrolidine-1-carboxylic acid tert-butyl ester. Pale yellow solid. MS376.1 ([M−H]⁻)

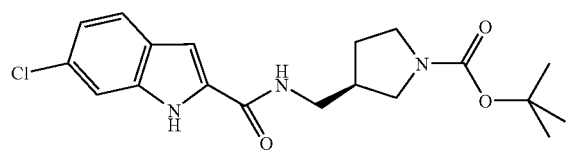

68.2 Using general procedure C, (R)-3-{[(6-chloro-1H-indole-2-carbonyl)-amino]-methyl}-pyrrolidine-1-carboxylic acid tert-butyl ester was converted to 6-chloro-1H-indole-2-carboxylic acid ((S)-1-pyrrolidin-3-ylmethyl)-amide trifluoro acetate. Pale yellow solid. MS 276.0 ([M−H]⁻)

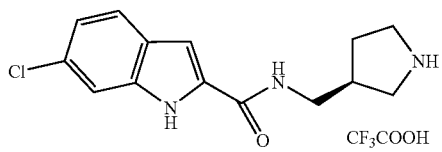

68.3 Using general method H, 6-chloro-1H-indole-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give 6-chloro-1H-indole-2-carboxylic acid {(R)-1-[2-fluoro-4-(2-oxo-2H-pyridin-1-yl)-phenylcarbamoyl]-pyrrolidin-3-ylmethyl}-amide. Pale yellow solid. MS 506.1 ([M−H]⁻)

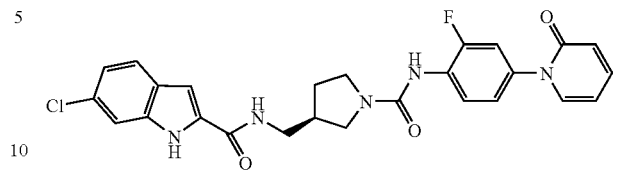

Example 69 (Reference)

69.1 Using general procedure E, (R)-3-aminomethyl-1-N-tert-butoxycarbonyl-pyrrolidine was coupled with 5-chloro-1H-indole-2-carboxylic acid to give (R)-3-{[(5-chloro-1H-indole-2-carbonyl)-amino]-methyl}-pyrrolidine-1-carboxylic acid tert-butyl ester. Pale yellow solid. MS 376.4 ([M−H]⁻)

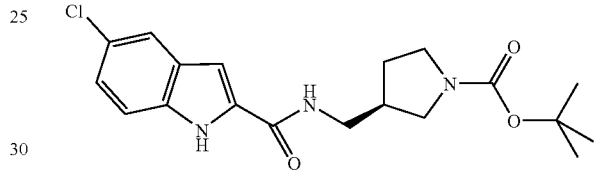

69.2 Using general procedure C, (R)-3-{[(5-chloro-1H-indole-2-carbonyl)-amino]-methyl}-pyrrolidine-1-carboxylic acid tert-butyl ester was converted to 5-chloro-1H-indole-2-carboxylic acid ((S)-1-pyrrolidin-3-ylmethyl)-amide trifluoro acetate. Pale yellow solid. MS 276.0 ([M−H])

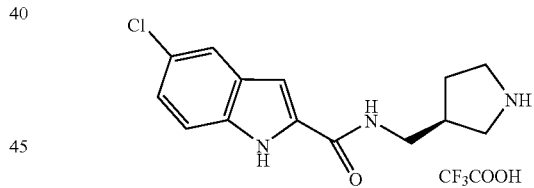

69.3 Using general method H, 5-chloro-1H-indole-2-carboxylic acid ((S)-1-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give 5-chloro-1H-indole-2-carboxylic acid {(R)-1-[2-fluoro-4-(2-oxo-2H-pyridin-1-yl)-phenylcarbamoyl]-pyrrolidin-3-ylmethyl}-amide. Pale yellow solid. MS 506.1 ([M−H]⁻)

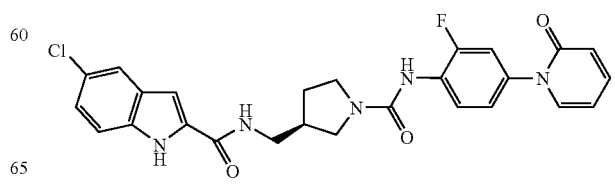

Example 70 (Reference)

70.1 Using general method G, 1-(4-amino-3-methyl-phenyl)-1H-pyridin-2-one (prepared according to WO 2003045912) was activated with 4-nitrophenyl chloroformate to give [2-methyl-4-(2-oxo-2H-pyridin-1-yl)-phenyl]-carbamic acid 4-nitro-phenyl ester. Pale grey solid.

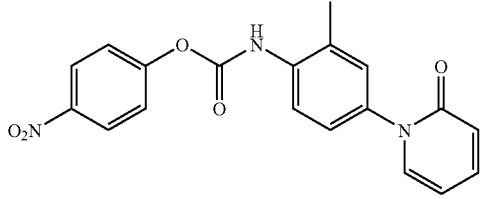

70.2 Using general method H, 5-chloro-thiophene-2-carboxylic acid ((S)-1-pyrrolidin-3-ylmethyl)-amide trifluoro acetate was reacted with [2-methyl-4-(2-oxo-2H-pyridin-1-yl)-phenyl]-carbamic acid 4-nitro-phenyl ester to give (R)-3-{[(5-chloro-thiophene-2-carbonyl)-amino]-methyl}-pyrrolidine-1-carboxylic acid[2-methyl-4-(2-oxo-2H-pyridin-1-yl)-phenyl]-amide. White solid. MS 471.1 ([M+H]$^+$)

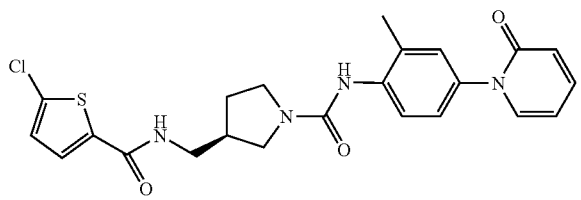

Example 71 (Reference)

71.1 Using general method G, 1-(4-amino-3-fluoro-phenyl)-1H-pyrazin-2-one (prepared according to WO 2003045912) was activated with 4-nitrophenyl chloroformate to give [2-fluoro-4-(2-oxo-2H-pyrazin-1-yl)-phenyl]-carbamic acid 4-nitro-phenyl ester. Pale yellow solid.

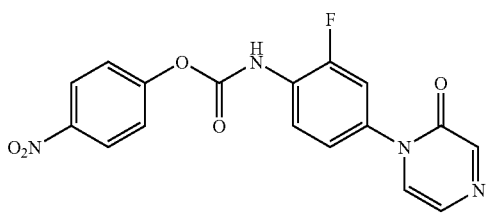

71.2 Using general method H, 5-chloro-thiophene-2-carboxylic acid ((S)-1-pyrrolidin-3-ylmethyl)-amide trifluoro acetate was reacted with [2-fluoro-4-(2-oxo-2H-pyrazin-1-yl)-phenyl]-carbamic acid 4-nitro-phenyl ester to give (R)-3-{[(5-chloro-thiophene-2-carbonyl)-amino]-methyl}-pyrrolidine-1-carboxylic acid[2-fluoro-4-(2-oxo-2H-pyrazin-1-yl)-phenyl]-amide. White solid. MS 476.0 ([M+H]$^+$)

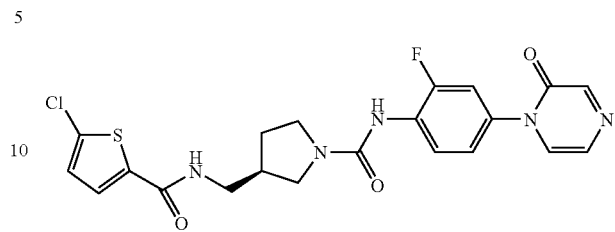

Example 72 (Reference)

72.1 Using general method G, 4-(4-amino-3-fluoro-phenyl)-morpholin-3-one (prepared according to WO 2003045912) was activated with 4-nitrophenyl chloroformate to give [2-fluoro-4-(3-oxo-morpholin-4-yl)-phenyl]-carbamic acid 4-nitro-phenyl ester. White solid.

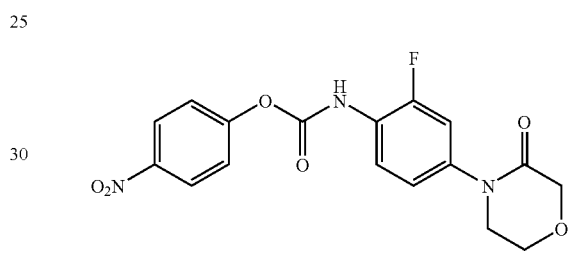

72.2 Using general method H. 5-chloro-thiophene-2-carboxylic acid ((S)-1-pyrrolidin-3-ylmethyl)-amide trifluoro acetate was reacted with [2-fluoro-4-(3-oxo-morpholin-4-yl)-phenyl]-carbamic acid 4-nitro-phenyl ester to give (R)-3-{[(5-chloro-thiophene-2-carbonyl)-amino]-methyl}-pyrrolidine-1-carboxylic acid[2-fluoro-4-(3-oxo-morpholin-4-yl)-phenyl]-amide. White solid. MS 481.3 ([M+H]$^+$)

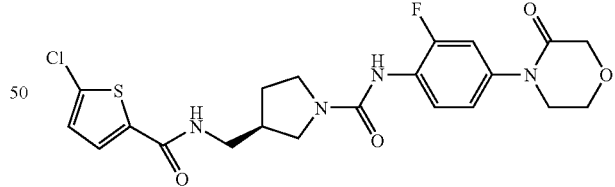

Example 73 (Reference)

73.1 To a solution of 10.96 g of 4-bromo-2-fluoro-benzoic acid in 40 ml of DMSO was added subsequently 6.67 g of 2-hydroxypyridine, 1.10 g of 8-hydroxyquinoline, 1.43 g of Cu(I)I and 7.61 g of $K_2CO_3$ and the mixture was heated to 150° C. for 18 h. The suspension was diluted with water, filtered, the residue was washed with AcOEt, triturated with MeOH, filtered and dried to give 5.77 g of 2-fluoro-4-(2-oxo-2H-pyridin-1-yl)-benzoic acid. MS: 234.1 (M+H)$^+$

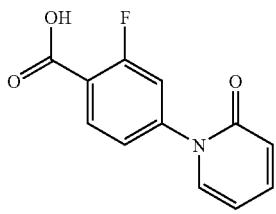

73.2 Using general method E, rac-5-chloro-thiophene-2-carboxylic acid-1-pyrrolidin-3-ylmethyl)-amide trifluoro acetate (prepared according to example 54.1-54.2) was reacted with 2-fluoro-4-(2-oxo-2H-pyridin-1-yl)-benzoic acid to give rac-5-chloro-thiophene-2-carboxylic acid {1-[2-fluoro-4-(2-oxo-2H-pyridin-1-yl)-benzoyl]-pyrrolidin-3-yl-methyl}-amide. White solid. MS 460.3 ([M+H]⁺)

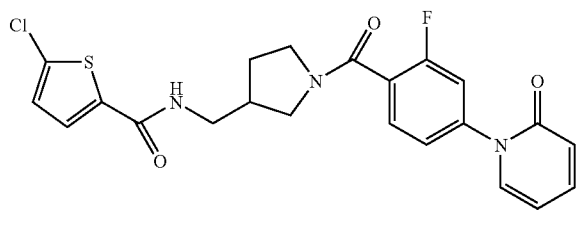

Example 74 (Reference)

74.1 Using the method described in example 73.1, 1,4-diiodobenzene was reacted with 2-hydroxypyridine to give 1-(4-iodo-phenyl)-1H-pyridin-2-one. Pale yellow solid. MS: 298.1 (M+H)⁺

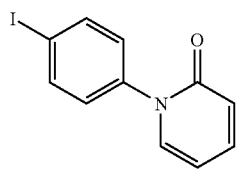

74.2 According to M. Hepperle et al. (Tetrahedron Letters, 2002, 43, 3359), a mixture of rac-5-chloro-thiophene-2-carboxylic acid-1-pyrrolidin-3-ylmethyl)-amide (27 mg, prepared according to example 54.1-54.2) and 1-(4-iodo-phenyl)-1H-pyridin-2-one (30 mg), in toluene (0.5 ml) and THF (0.25 ml) was treated with rac-2,2'-bis-(diphenylphosphino)-1,1'-binaphtaline (4 mg), tris-(dibenzylideneacetone)-dipalladium chloroform complex (2.5 mg) and a solution of NaOt-Bu (17 mg) in THF (0.25 ml) and heated to reflux temperature for 5 h. The mixture was partitioned between 1 N HCl and AcOEt, the organic layer was dried and evaporated. The crude material was purified by preparative thin layer chromatography on silica using CH₂Cl₂/MeOH (9:1) to give rac-5-chloro-thiophene-2-carboxylic acid {1-[4-(2-oxo-2H-pyridin-1-yl)-phenyl]-pyrrolidin-3-ylmethyl}-amide. Yellow oil. MS 414.0 ([M+H]⁺)

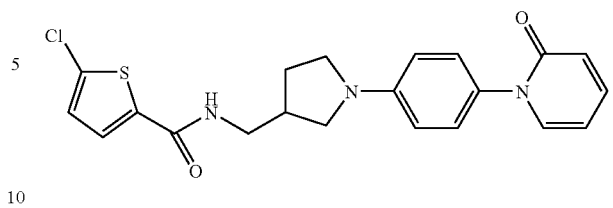

Example 75 (Reference)

75.1 Using general procedure E, rac-2-aminomethyl-1-N-tert-butoxycarbonyl-pyrrolidine was coupled with 5-chlorothiophene-2-carboxylic acid to give rac-2-{[(5-chloro-thiophene-2-carbonyl)-amino]-methyl}-pyrrolidine-1-carboxylic acid tert-butyl ester. Brown oil. MS 345.0 ([M+H]⁺)

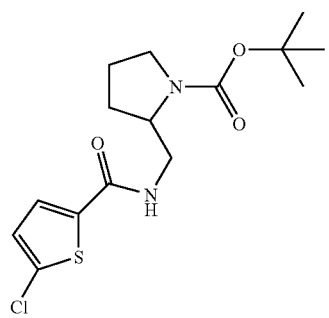

75.2 Using general procedure C, rac-2-{[(5-chloro-thiophene-2-carbonyl)-amino]-methyl}-pyrrolidine-1-carboxylic acid tert-butyl ester was converted to rac-5-chloro-thiophene-2-carboxylic acid (pyrrolidin-2-ylmethyl)-amide trifluoro acetate. Red oil. MS 245.4 ([M+H]⁺)

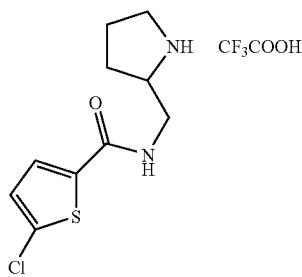

75.3 Using general method H, rac-5-chloro-thiophene-2-carboxylic acid (pyrrolidin-2-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give rac-2-{[(5-chloro-thiophene-2-carbonyl)-amino]-methyl}-pyrrolidine-1-carboxylic acid[2-fluoro-4-(2-oxo-2H-pyridin-1-yl)-phenyl]-amide. Pale yellow solid. MS 475.1 ([M+H]⁺)

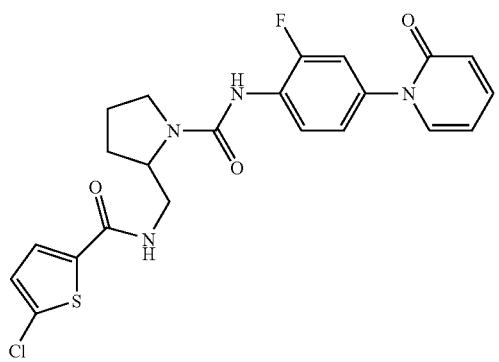

Example 76 (Reference)

Using general method H, rac-5-chloro-thiophene-2-carboxylic acid (pyrrolidin-2-ylmethyl)-amide trifluoro acetate (example 75.2) was reacted with 2-fluoro-4-(2-oxo-2H-pyridin-1-yl)-benzoic acid (prepared according to example 54.1) to give rac-5-chloro-thiophene-2-carboxylic acid {1-[2-fluoro-4-(2-oxo-2H-pyridin-1-yl)-benzoyl]-pyrrolidin-2-ylmethyl}-amide. White solid. MS 460.0 ([M+H]$^+$)

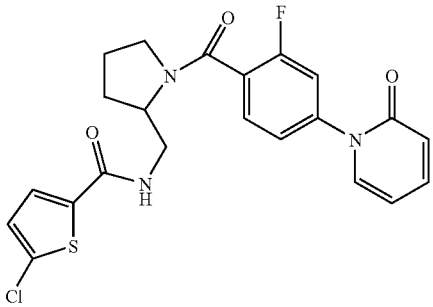

Example 77

77.1 Using general procedure H, (3S,4S)-(4-trifluoromethyl-pyrrolidin-3-ylmethyl)-carbamic acid tert-butyl ester (H. Fukui et al., Bioorganic & Medicinal Chemistry Letters, 1998, 8, 2833) was coupled with [2-fluoro-4-(2-oxo-2H-pyridin-1-yl)-phenyl]-carbamic acid 4-nitro-phenyl ester (prepared according to example 54.3) to give {(3R,4S)-1-[2-fluoro-4-(2-oxo-2H-pyridin-1-yl)-phenylcarbamoyl]-4-trifluoromethyl-pyrrolidin-3-ylmethyl}-carbamic acid tert-butyl ester. Orange oil. MS 499.3 ([M+H]$^+$)

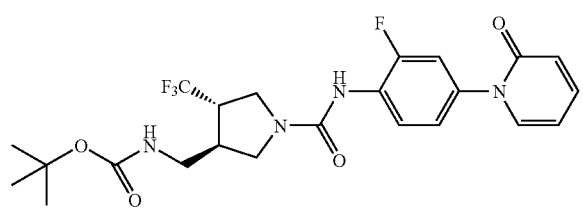

77.2 Using general method C, {(3R,4S)-1-[2-fluoro-4-(2-oxo-2H-pyridin-1-yl)-phenylcarbamoyl]-4-trifluoromethyl-pyrrolidin-3-ylmethyl}-carbamic acid tert-butyl ester was converted to (3R,4S)-3-aminomethyl-4-trifluoromethyl-pyrrolidine-1-carboxylic acid [2-fluoro-4-(2-oxo-2H-pyridin-1-yl)-phenyl]-amide trifluoro acetate. Red oil. MS 399.1 ([M+H]$^+$)

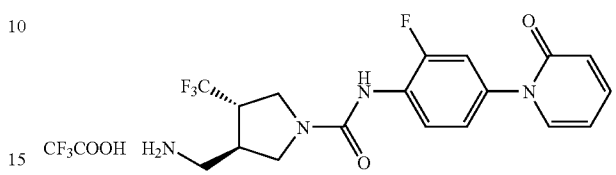

77.3 Using general method E, (3R,4S)-3-aminomethyl-4-trifluoromethyl-pyrrolidine-1-carboxylic acid[2-fluoro-4-(2-oxo-2H-pyridin-1-yl)-phenyl]-amide trifluoro acetate was coupled with 5-chlorothiophene-2-carboxylic acid to give (3R,4S)-3-{[(5-chloro-thiophene-2-carbonyl)-amino]-methyl}-4-trifluoromethyl-pyrrolidine-1-carboxy-lic acid[2-fluoro-4-(2-oxo-2H-pyridin-1-yl)-phenyl]-amide. White solid. MS 443.0 ([M+H]$^+$)

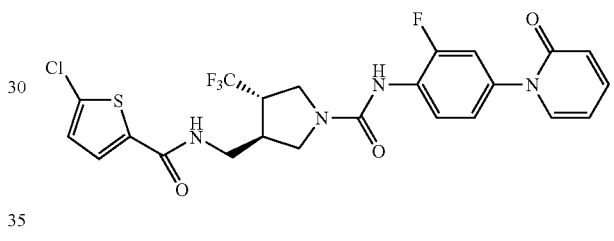

Example 78

The enantiomer (3S,4R)-3-{[(5-chloro-thiophene-2-carbonyl)-amino]-methyl}-4-trifluoromethyl-pyrrolidine-1-carboxylic acid[2-fluoro-4-(2-oxo-2H-pyridin-1-yl)-phenyl]-amide was prepared according to examples 77.1-77.3 starting with (3R,4R)-(4-trifluoromethyl-pyrrolidin-3-ylmethyl)-carbamic acid tert-butyl ester (H. Fukui et al., Bioorganic & Medicinal Chemistry Letters, 1998, 8, 2833). Pale yellow solid. MS 543.2 ([M+H]$^+$)

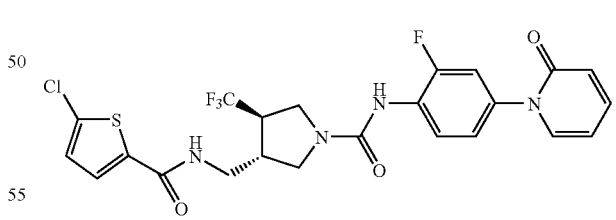

Example 79

79.1 To a solution of 17.1 g (98.2% GC purity) of trans, rac-3-cyano-4-hydroxy-pyrrolidine-1-carboxylic acid tert-butyl ester (prepared according to C. Y. Hong et al. (Bioorganic Medicinal Chemistry Letters, 2003, 13, 4399), by D. J. Kim et al. (Journal of Medicinal Chemistry, 1997, 40, 3584) or by S. U. Hansen & M. Bols (Acta Chemica Scandinavica, 1997, 52, 1214)) in 765 ml of t-butylmethyl ether and 85 ml of vinyl acetate was added 21.3 g of Lipase AK (Amano Enzyme Inc.) and the suspension was stirred at 22° C. until ca. 54% conversion (as calculated from the ee-values of substrate and product according to C. J. Sih et al. (J. Am. Chem. Soc., 1982, 104, 7294)) was reached. The enzyme was filtered off, the filtrate evaporated in vacuo and the residual oil chromatographed on 400 g silicagel (0.040-0.063 mm; dichloromethane/diethyl ether 9:1→3:1) to give the formed optically enriched (S,S)-3-acetoxy-4-cyano-pyrrolidine-1-carboxylic acid tert-butyl ester (10.7 g; 84% ee, optically further enriched in example 60.2) and the retained (R,R)-3-cyano-4-hydroxy-pyrrolidine-1-carboxylic acid tert-butyl ester (6.9 g). Analytics: +EI-MS: 213.3 (M+H$^+$); [α]$_D$=+1.20° (c=1.00, CHCl$_3$); 97.8% ee (GC on BGB-176; 30 m×0.25 mm; H$_2$; 90 kPa; 130° C. to 200° C. with 2° C./min; inj. 200° C.).

79.2 The optically enriched (S,S)-3-acetoxy-4-cyano-pyrrolidine-1-carboxylic acid tert-butyl ester (10.4 g, 84% ee) was dissolved in 500 ml of t-butylmethyl ether (slow). The solution was emulsified under vigorous stirring with 4 l of 0.1M NaCl, 3.7 mM sodium phosphate buffer pH 7.0. Hydrolysis was started by adding 750 mg of Chirazyme L-2 (Roche Applied Sciences) and the pH was kept at 7.0 by the controlled addition of 0.1 M NaOH-solution

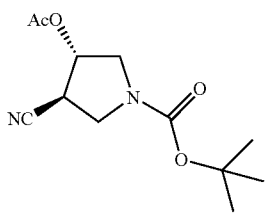

(pH-stat) under vigorous stirring at r.t. After a consumption of 51.3 ml 0.1M NaOH-solution (after 91 h) the reaction mixture was extracted with 4 l and 2×3 l of dichloromethane (uncomplete phase separation due to intermediate phase). The combined organic phases were concentrated and the residual oil chromatographed on 150 g silicagel (0.040-0.063 mm; dichloromethane/diethyl ether 9:1) to give the retained optically further enriched (S,S)-3-acetoxy-4-cyano-pyrrolidine-1-carboxylic acid tert-butyl ester (8.1 g). Analytics: +EI-MS: 255 (M+H$^+$); [α]$_D$=−11.88° (c=1.02, CHCl$_3$); 98.7% ee (GC on BGB-176; 30 m×0.25 mm; H$_2$; 90 kPa; 130° C. to 200° C. with 2° C./min; inj. 200° C.).

79.3 A suspension of (3S,4S)-3-acetoxy-4-cyano-pyrrolidine-1-carboxylic acid tert-butyl ester (89 mg) in 10 ml of AcOEt and 0.2 ml of chloroform, 0.2 ml of AcOH and 4 mg of PtO$_2$ was hydrogenated at 22° C. and atmospheric pressure for 16 h. The suspension was filtered and the filtrate evaporated to give (3S,4R)-3-acetoxy-4-aminomethyl-pyrrolidine-1-carboxylic acid tert-butyl ester acetate. Colorless semisolid. MS 259.3 ([M+H]$^+$)

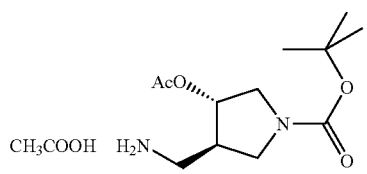

79.4 Using general procedure E, (3S,4R)-3-acetoxy-4-aminomethyl-pyrrolidine-1-carboxylic acid tert-butyl ester acetate was coupled with 5-chlorothiophene-2-carboxylic acid to give (3S,4R)-3-acetoxy-4-{[(5-chloro-thiophene-2-carbonyl)-amino]-methyl}-pyrrolidine-1-carboxylic acid tert-butyl ester. Brown oil. MS 347.0 ([M-iso-butene+H]$^+$)

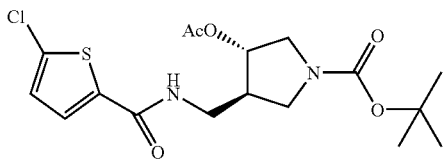

79.5 A solution of (3S,4R)-3-acetoxy-4-{[(5-chloro-thiophene-2-carbonyl)-amino]-methyl}-pyrrolidine-1-carboxylic acid tert-butyl ester (20 mg) in 1 ml of a 2M NH$_3$ solution in MeOH was stirred at 22° C. for 1 h and evaporated to give (3R,4S)-3-{[(5-chloro-thiophene-2-carbonyl)-amino]-methyl}-4-hydroxy-pyrrolidine-1-carboxylic acid tert-butyl ester. Pale brown oil. MS 305.1 ([M-isobutene+H]$^+$)

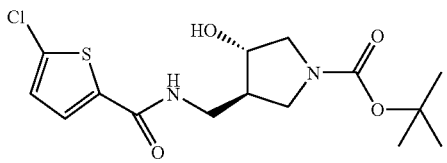

79.6 Using general method C, (3R,4S)-3-{[(5-chloro-thiophene-2-carbonyl)-amino]-methyl}-4-hydroxy-pyrrolidine-1-carboxylic acid tert-butyl ester was converted to (3S,4S)-5-chloro-thiophene-2-carboxylic acid (4-hydroxy-pyrrolidin-3-ylmethyl)-amide trifluoro acetate. Yellow oil. MS 261.0 ([M+H]$^+$)

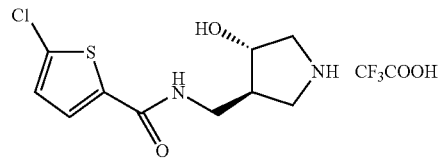

79.7 Using general method H, to (3S,4S)-5-chloro-thiophene-2-carboxylic acid (4-hydroxy-pyrrolidin-3-ylmethyl)-amide trifluoro acetate was reacted with [2-fluoro-4-(2-oxo-2H-pyridin-1-yl)-phenyl]-carbamic acid 4-nitrophenyl ester (prepared according to example 54.3) to give (3R,4S)-3-{[(5-chloro-thiophene-2-carbonyl)-amino]-methyl}-4-hydroxy-pyrrolidine-1-carboxylic acid[2-fluoro-4-(2-oxo-2H-pyridin-1-yl)-phenyl]-amide. Colorless solid. MS 491.0 ([M+H]$^+$)

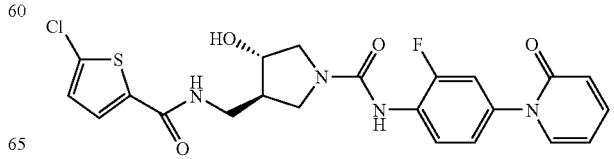

Example 80

80.1 A solution of (3S,4S)-3-acetoxy-4-cyano-pyrrolidine-1-carboxylic acid tert-butyl ester (1.00 g, prepared according to example 79.2) in 10 ml of a 2M $NH_3$ solution in MeOH was stirred at 22° C. for 1 h and evaporated. The residue was chromatographed on silica (heptane/AcOEt, 2.5:1) to give (3S,4S)-3-cyano-4-hydroxy-pyrrolidine-1-carboxylic acid tert-butyl ester. Colorless solid. MS 213.3 ([M+H]$^+$)

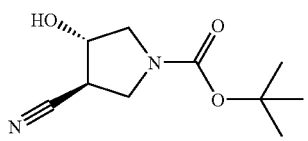

80.2 A suspension of (3S,4S)-3-cyano-4-hydroxy-pyrrolidine-1-carboxylic acid tert-butyl ester (212 mg) in 10 ml of THF and 2.32 g of $Ag_2O$ and 0.62 ml of $CH_3I$ was heated in a sealed tube to 50° C. for 16 h. The suspension was filtered and the filtrate chromatographed on silica (heptane/AcOEt, 3:1) to give 161 mg of (3S,4S)-3-cyano-4-methoxy-pyrrolidine-1-carboxylic acid tert-butyl ester. Colorless oil. MS 171.4 ([M-isobutene+H]$^+$)

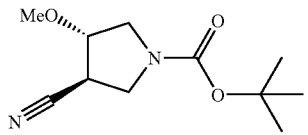

80.3 A suspension of (3S,4S)-3-cyano-4-methoxy-pyrrolidine-1-carboxylic acid tert-butyl ester (150 mg) in 15 ml of EtOH, 0.3 ml of chloroform, 0.38 ml of AcOH and 8 mg of $PtO_2$ was hydrogenated at 22° C. and atmospheric pressure for 16 h. The suspension was filtered and the filtrate evaporated to give 188 mg of (3R,4S)-3-aminomethyl-4-methoxy-pyrrolidine-1-carboxylic acid tert-butyl ester acetate. Colorless semisolid. MS 231.3 ([M+H]$^+$)

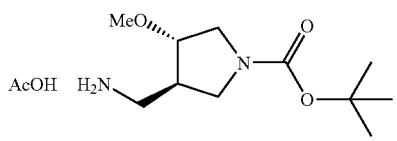

80.4 Using general procedure E, (3R,4S)-3-aminomethyl-4-methoxy-pyrrolidine-1-carboxylic acid tert-butyl ester acetate was coupled with 5-chlorothiophene-2-carboxylic acid to give (3R,4S)-3-{[(5-chloro-thiophene-2-carbonyl)-amino]-methyl}-4-methoxy-pyrrolidine-1-carboxylic acid tert-butyl ester. Colorless foam. MS 318.9 ([M-isobutene+H]$^+$)

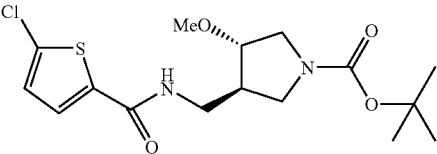

80.5 Using general method C, (3R,4S)-3-{[(5-chloro-thiophene-2-carbonyl)-amino]-methyl}-4-methoxy-pyrrolidine-1-carboxylic acid tert-butyl ester was converted to 5-chloro-thiophene-2-carboxylic acid ((3S,4S)-4-methoxy-pyrrolidin-3-ylmethyl)-amide trifluoro acetate. Pale yellow oil. MS 275.1 ([M+H]$^+$)

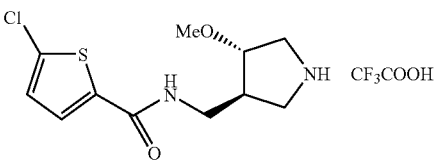

80.6 Using general method H, 5-chloro-thiophene-2-carboxylic acid ((3S,4S)-4-methoxy-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (3R,4S)-3-{[(5-chloro-thiophene-2-carbonyl)-amino]-methyl}-4-methoxy-pyrrolidine-1-carboxylic acid[2-fluoro-4-(2-oxo-2H-pyridin-1-yl)-phenyl]-amide. Pale yellow solid. MS 505.1 ([M+H]$^+$)

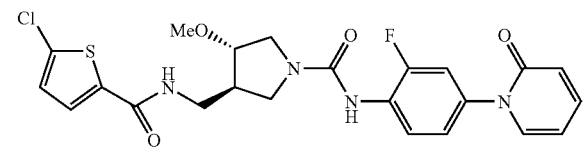

Example 81

81.1 To a solution of (3R,4S)-3-{[(5-chloro-thiophene-2-carbonyl)-amino]-methyl}-4-hydroxy-pyrrolidine-1-carboxylic acid tert-butyl ester (600 mg, prepared according to example 79.5) in 10 ml of $CH_2Cl_2$ was added at 5° C. 2.30 ml of $NEt_3$ and 1.59 g of $SO_3$-pyridine complex, the solution was warmed to 22° C. and stirring was continued for 3 h. The mixture was washed with aqueous $NH_4Cl$, the organic layer was dried and evaporated. The residue was chromatographed on silica (heptane/AcOEt, 2:1) to give 435 mg of (R)-3-{[(5-chloro-thiophene-2-carbonyl)-amino]-methyl}-4-oxo-pyrrolidine-1-carboxylic acid tert-butyl ester. Pale yellow solid. MS 303.0 ([M-isobutene+H]$^+$)

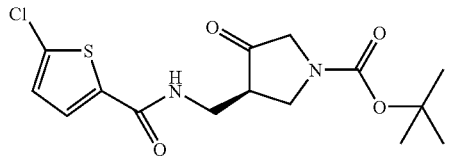

81.2 Using general method C, (R)-3-1{[(5-chloro-thiophene-2-carbonyl)-amino]-methyl}-4-oxo-pyrrolidine-1-carboxylic acid tert-butyl ester was converted to 5-chloro-thiophene-2-carboxylic acid ((S)-4-oxo-pyrrolidin-3-ylmethyl)-amide trifluoro acetate. Green oil. MS 259.0 ([M+H]⁺)

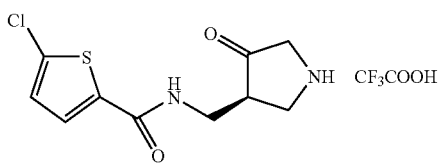

81.3 Using general method H, 5-chloro-thiophene-2-carboxylic acid ((S)-4-oxo-pyrrolidin-3-ylmethyl)-amide trifluoro acetate was reacted with [2-fluoro-4-(2-oxo-2H-pyridin-1-yl)-phenyl]-carbamic acid 4-nitro-phenyl ester (prepared according to example 54.3) to give (R)-3-{[(5-chloro-thiophene-2-carbonyl)-amino]-methyl}-4-oxo-pyrrolidine-1-carboxylic acid[2-fluoro-4-(2-oxo-2H-pyridin-1-yl)-phenyl]-amide. Pale brown solid. MS 489.0 ([M+H]⁺)

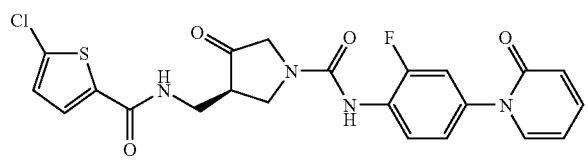

Example 82

To a solution of (R)-3-{[(5-chloro-thiophene-2-carbonyl)-amino]-methyl}-4-oxo-pyrrolidine-1-carboxylic acid[2-fluoro-4-(2-oxo-2H-pyridin-1-yl)-phenyl]-amide (example 81.3; 50 mg) in 2 ml of THF was added at 22° C. 12 mg of NaBH₄ and stirring was continued for 1.5 h. The mixture was partitioned between 1 N HCl and AcOEt, the organic layer was washed with brine, dried and evaporated to give (3R,4R)-3-{[(5-chloro-thiophene-2-carbonyl)-amino]-methyl}-4-hydroxy-pyrrolidine-1-carboxylic acid[2-fluoro-4-(2-oxo-2H-pyridin-1-yl)-phenyl]-amide. White solid. MS491.3 ([M+H]⁺)

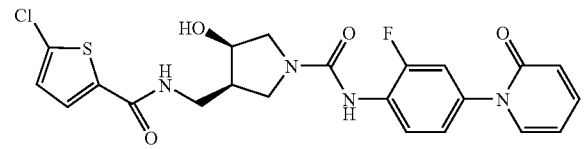

Example 83

A solution of the (R)-3-{[(5-chloro-thiophene-2-carbonyl)-amino]-methyl}-4-oxo-pyrrolidine-1-carboxylic acid [2-fluoro-4-(2-oxo-2H-pyridin-1-yl)-phenyl]-amide (120 mg, example 81.3) and 12 ml of THF saturated with methylamine was treated at 5° C. with 3.5 ml of AcOH until pH=6 and the mixture was warmed to 22° C. After 1.5 h, the mixture was treated with 24 mg of Na(CN)BH₃ and stirring was continued for 2.5 h. The mixture was diluted with 5 ml of water, the pH was adjusted to 14 using 3 N NaOH and the solution was extracted with THF. The organic layer was dried and evaporated to give (R)-3-{[(5-chloro-thiophene-2-carbonyl)-amino]-methyl}-4-methylamino-pyrrolidine-1-carboxylic acid[2-fluoro-4-(2-oxo-2H-pyridin-1-yl)-phenyl]-amide. Colorless foam. MS 504.0 ([M+H]⁺)

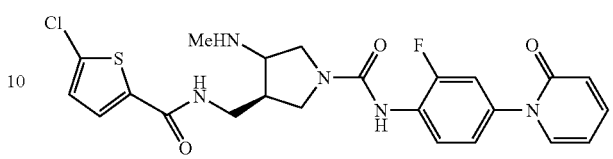

Example 84

To a solution of (R)-3-{[(5-chloro-thiophene-2-carbonyl)-amino]-methyl}-4-methylamino-pyrrolidine-1-carboxylic acid[2-fluoro-4-(2-oxo-2H-pyridin-1-yl)-phenyl]-amide (example 83; 25 mg) in 0.8 ml of CH₃CN and 19-II of N,N-diisopropylethylamine was added at 22° C. 6 mg of methyl-chloroformate and stirring was continued for 3 h. The mixture was diluted with 0.5 ml of MeOH, evaporated and the residue was chromatographed on silica (AcOEt/MeOH, 15:1) to give {(R)-4-1{[(5-chloro-thiophene-2-carbonyl)-amino]-methyl}-1-[2-fluoro-4-(2-oxo-2H-pyridin-1-yl)-phenyl-carbamoyl]-pyrrolidin-3-yl}-methyl-carbamic acid methyl ester. Colorless solid. MS 562.0 ([M+H]⁺)

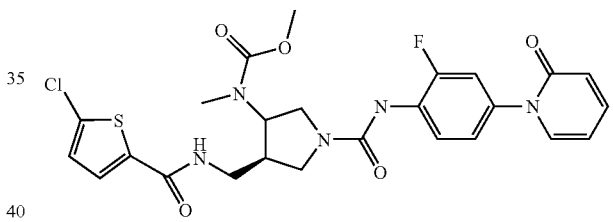

Example 85

To a solution of (R)-3-{[(5-chloro-thiophene-2-carbonyl)-amino]-methyl}-4-methylamino-pyrrolidine-1-carboxylic acid[2-fluoro-4-(2-oxo-2H-pyridin-1-yl)-phenyl]-amide (example 83; 26 mg) in 0.8 ml of CH₃CN and 22 μl of N,N-diisopropylethylamine was added at 22° C. 6 μl of methane-sulfonylchloride and stirring was continued for 3 h. The mixture was diluted with 0.5 ml of MeOH, evaporated and the residue was chromatographed on silica (AcOEt/MeOH, 15:1) to give (R)-3-{[(5-chloro-thiophene-2-carbonyl)-amino]-methyl}-4-(methanesulfonyl-methyl-amino)-pyrrolidine-1-carboxylic acid[2-fluoro-4-(2-oxo-2H-pyridin-1-yl)-phenyl]-amide. Colorless solid. MS 582.0 ([M+H]⁺)

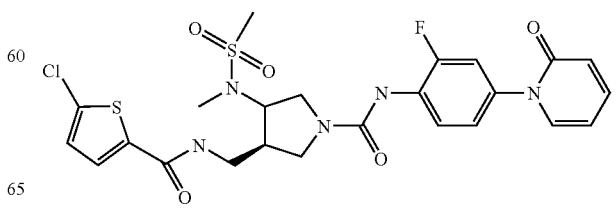

Example 86

In analogy to examples 17.3-17.5 (2S,4R)-4-[(5-chloro-thiophene-2-carbonyl)-amino]-2-methanesulfonyloxymethyl-pyrrolidine-1-carboxylic acid tert-butyl ester (examples 17.2) was reacted with morpholine and then converted to 5-chloro-thiophene-2-carboxylic acid ((3R,5S)-1-{[2-fluoro-4-(2-oxo-2H-pyridin-1-yl)-phenylcarbamoyl]-methyl}-5-morphoslin-4-ylmethyl-pyrrolidin-3-yl)-amide. Off-white amorphous solid. MS 574.0 ([M+H]$^+$)

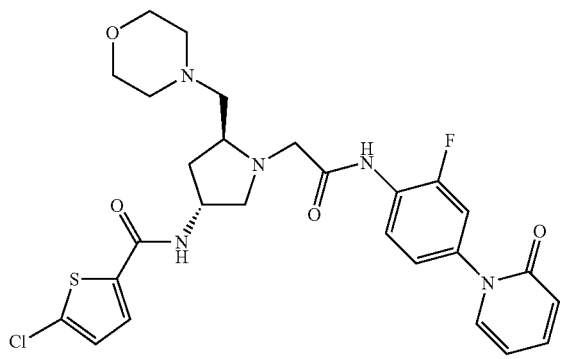

Example 87

In analogy to examples 17.3-17.5 (2S,4R)-4-[(5-chloro-thiophene-2-carbonyl)-amino]-2-methanesulfonyloxymethyl-pyrrolidine-1-carboxylic acid tert-butyl ester (example 17.2) was reacted with 3,3-difluoropyrrolidine and then converted to 5-chloro-thiophene-2-carboxylic acid ((3R,5S)-5-(3,3-difluoro-pyrrolidin-1-ylmethyl)-1-{[2-fluoro-4-(2-oxo-2H-pyridin-1-yl)-phenylcarbamoyl]-methyl}-pyrrolidin-3-yl)-amide. Light yellow amorphous solid. MS 594.3 ([M+H]$^+$)

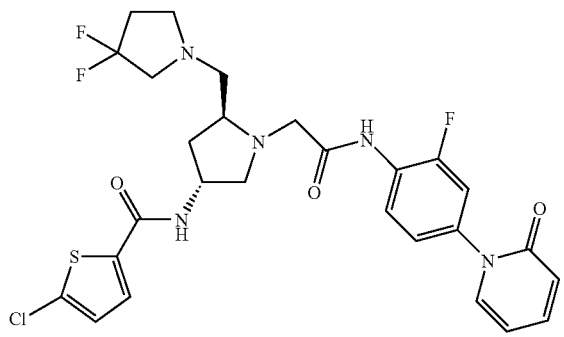

Example 88

In analogy to examples 17.3-17.5 (2S,4R)-4-[(5-chloro-thiophene-2-carbonyl)-amino]-2-methanesulfonyloxymethyl-pyrrolidine-1-carboxylic acid tert-butyl ester (example 17.2) was reacted with cyclopropylamine and then converted to 5-chloro-thiophene-2-carboxylic acid ((3R,5S)-5-cyclopropylaminomethyl-1-{[2-fluoro-4-(2-oxo-2H-pyridin-1-yl)-phenyl-carbamoyl]-methyl}-pyrrolidin-3-yl)-amide. Off-white amorphous solid. MS 544.2 ([M+H]$^+$)

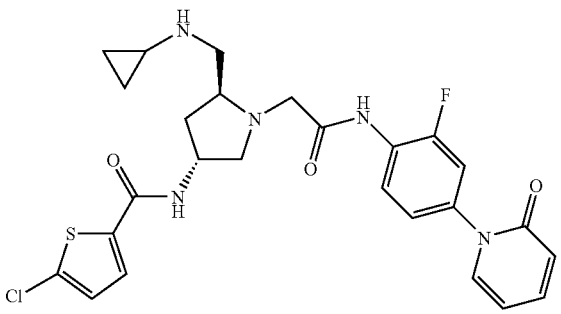

Example 89

89.1 To a stirred, cooled (0° C.) solution of 1.48 g (2S,4R)-4-[(5-chloro-thiophene-2-carbonyl)-amino]-2-hydroxymethyl-pyrrolidine-1-carboxylic acid tert-butyl ester (example 17.1) in 30 ml CH$_2$Cl$_2$/DMSO 1:1 under an argon atmosphere were added 5.7 ml triethylamine and 3.92 g SO$_3$-pyridine complex in one portion. The clear solution (slowly warming up to room temperature) was then stirred for 3 h. The mixture was diluted with EtOAc and washed with 1 N HCl. The aqueous phase was back extracted with EtOAc. The combined organics were washed with 1 N HCl, H$_2$O and brine, dried over MgSO$_4$, filtered and concentrated. The crude product was purified by chromatography (silica gel; cyclohexane/EtOAc 1:1) to give 985 mg (2S,4R)-4-[(5-chloro-thiophene-2-carbonyl)-amino]-2-formyl-pyrrolidine-1-carboxylic acid tert-butyl ester as white amorphous solid. MS 359.0 ([M+H]$^+$)

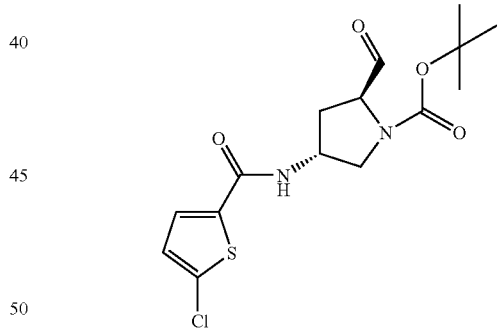

89.2 A mixture of 200 mg (2S,4R)-4-[(5-chloro-thiophene-2-carbonyl)-amino]-2-formyl-pyrrolidine-1-carboxylic acid tert-butyl ester, 90 mg 2,2-difluorethyl amine (solution in 1 ml THF) and 0.33 ml tetraisopropyl orthotitanate was stirred at r.t. for 1 h 30. The mixture was diluted with 1.5 ml ethanol and 35 mg NaBH$_3$CN was added. Stirring at r.t. was continued for 18 h. Then, 0.5 ml H$_2$O was added and stirring was continued for 30 min. The mixture was concentrated. The crude product was purified by column chromatography (silica gel; gradient: cyclohexane->cyclohexane/EtOAc 3:7) to give 105 mg (2S,4R)-4-[(5-chloro-thiophene-2-carbonyl)-amino]-2-[(2,2-difluoro-ethylamino)-methyl]-pyrrolidine-1-carboxylic acid tert-butyl ester as white amorphous solid. MS 424.0 ([M+H]$^+$)

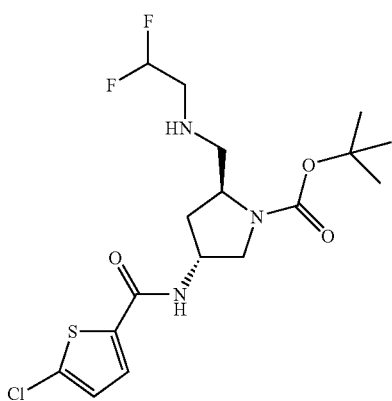

89.3 In analogy to examples 17.4 and 17.5 (2S,4R)-4-[(5-chloro-thiophene-2-carbonyl)-amino]-2-[(2,2-difluoro-ethylamino)-methyl]-pyrrolidine-1-carboxylic acid tert-butyl ester was converted to 5-chloro-thiophene-2-carboxylic acid ((3R,5S)-5-[(2,2-difluoro-ethylamino)-methyl]-1-{[2-fluoro-4-(2-oxo-2H-pyridin-1-yl)-phenylcarbamoyl]-methyl}-pyrrolidin-3-yl)-amide. Light yellow amorphous solid. MS 568.2 ([M+H]$^+$)

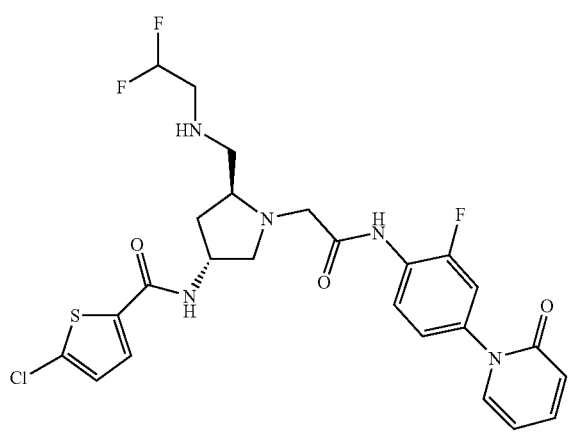

Example 90

90.1 To a stirred, cooled (0° C.) suspension of 55 mg NaH (55% dispersion in mineral oil) in 2 ml DMF under an argon atmosphere was added 84 mg 2,2-difluoroethanol (solution in 1 ml DMF). The ice bath was removed and stirring at r.t. was continued for 1 h. A solution of 150 mg (2S,4R)-4-[(5-chloro-thiophene-2-carbonyl)-amino]-2-methanesulfonyloxymethyl-pyrrolidine-1-carboxylic acid tert-butyl ester (example 17.2) in 2 ml DMF was then added. The mixture was heated to 80° C. and stirring at that temperature was continued for 21 h. The mixture was cooled to r.t., diluted with EtOAc and washed with H$_2$O. The aqueous phase was back extracted with EtOAc. The combined organics were washed with H$_2$O and brine, dried over MgSO$_4$, filtered and concentrated. The crude product was purified by column chromatography (silica gel; cyclohexane->cyclohexane/EtOAc 1:1) to give 12 mg (2S,4R)-4-[(5-chloro-thiophene-2-carbonyl)-amino]-2-(2,2-difluoro-ethoxymethyl)-pyrrolidine-1-carboxylic acid tert-butyl ester as colorless gum. MS 425.0 ([M+H]$^+$)

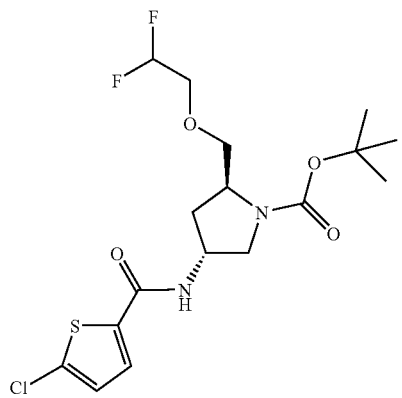

90.2 In analogy to examples 17.4 and 17.5 (2S,4R)-4-[(5-chloro-thiophene-2-carbonyl)-amino]-2-(2,2-difluoro-ethoxymethyl)-pyrrolidine-1-carboxylic acid tert-butyl ester was converted to 5-chloro-thiophene-2-carboxylic acid ((3R,5S)-5-(2,2-difluoro-ethoxymethyl)-1-{[2-fluoro-4-(2-oxo-2H-pyridin-1-yl)-phenylcarbamoyl]-methyl}-pyrrolidin-3-yl)-amide. Off-white solid. MS 569.2 ([M+H]$^+$)

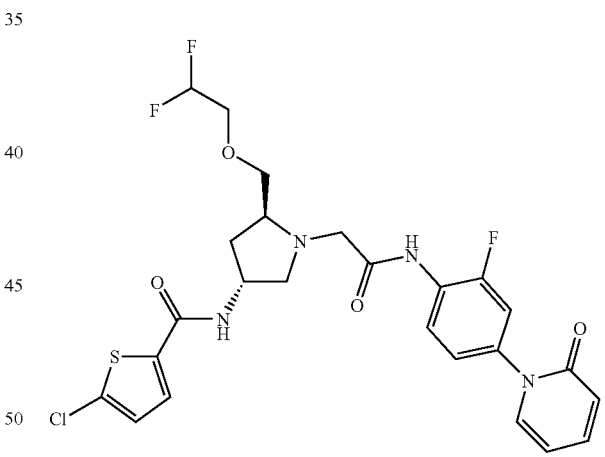

Example 91

91.1 To a stirred solution of 150 mg (2S,4R)-4-[(5-chloro-thiophene-2-carbonyl)-amino]-2-methanesulfonyloxymethyl-pyrrolidine-1-carboxylic acid tert-butyl ester (example 17.2) at r.t. in 3.3 ml DMF under an argon atmosphere was added 1.71 ml tetrabutylammonium fluoride solution (1 M in THF). The mixture was heated to 80° C. and stirring at that temperature was continued for 19 h. The mixture was cooled to r.t., diluted with EtOAc and washed with H$_2$O. The aqueous phase was back extracted with EtOAc. The combined organics were washed with H$_2$O and brine, dried over MgSO$_4$, filtered and concentrated. The crude product was purified by column chromatography (silica gel; cyclohexane->cyclohexane/EtOAc 1:1) to give 44 mg (2S,4R)-4-[(5-chloro-thiophene-2-carbonyl)-amino]-2-fluoromethyl-pyrrolidine-1-carboxylic acid tert-butyl ester as off-white amorphous solid. MS 361.0 ([M−H]⁻)

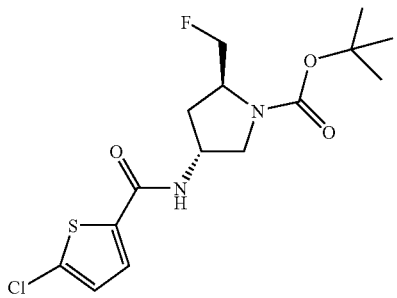

91.2 In analogy to examples 17.4 and 17.5 (2S,4R)-4-[(5-chloro-thiophene-2-carbonyl)-amino]-2-fluoromethyl-pyrrolidine-1-carboxylic acid tert-butyl ester was converted to 5-chloro-thiophene-2-carboxylic acid ((3R,5S)-5-fluoromethyl-1-{[2-fluoro-4-(2-oxo-2H-pyridin-1-yl)-phenylcarbamoyl]-methyl}-pyrrolidin-3-yl)-amide. Light yellow amorphous solid. MS 507.3 ([M+H]⁺)

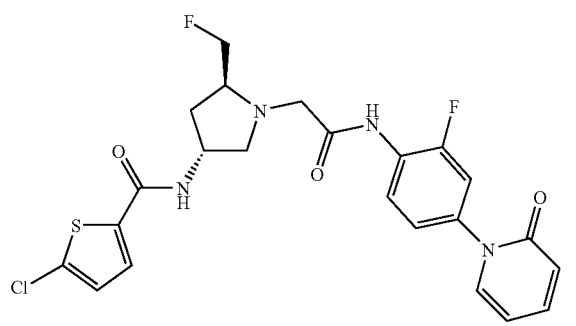

Example 92

In analogy to example 25.3 {(3S,4S)-3-[(5-chloro-thiophene-2-carbonyl)-amino]-4-methoxy-pyrrolidin-1-yl}-acetic acid ethyl ester (example 25.2) was reacted with 3-(4-amino-3-fluoro-phenyl)-oxazolidin-2-one (prepared from 2-fluoro-4-iodoaniline and 2-oxazolidinone in the presence of Cu(I)I, ethylenediamine and potassium phosphate in dioxane at 110° C.) to give 5-chloro-thiophene-2-carboxylic acid ((3S,4S)-1-{[2-fluoro-4-(2-oxo-oxazolidin-3-yl)-phenylcarbamoyl]-methyl}-4-methoxy-pyrrolidin-3-yl)-amide as yellow solid. MS 497.5 ([M+H]⁺)

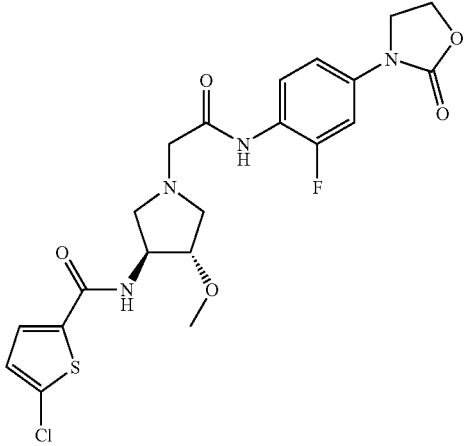

Example 93

In analogy to example 25.3 {(3S,4S)-3-[(5-chloro-thiophene-2-carbonyl)-amino]-4-methoxy-pyrrolidin-1-yl}-acetic acid ethyl ester (example 25.2) was reacted with 5-methyl-4,5,6,7-tetrahydro-thiazolo[5,4]pyridin-2-ylamine (CAS 17899-48-8) to give 5-chloro-thiophene-2-carboxylic acid {(3S,4S)-4-methoxy-1-[(5-methyl-4,5,6,7-tetrahydro-thiazolo[5,4]pyridin-2-ylcarbamoyl)-methyl]-pyrrolidin-3-yl}-amide as yellow solid. MS 470.5 ([M+H]⁺)

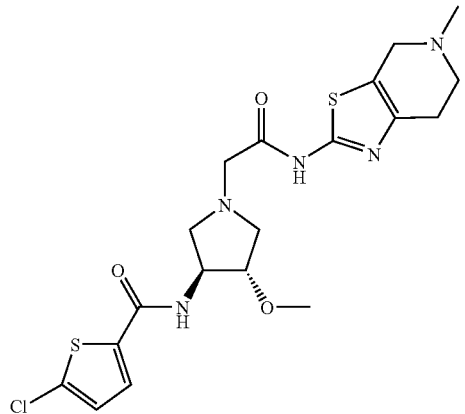

Example 94

94.1 In analogy to example 25.3 {(3S,4S)-3-[(5-chloro-thiophene-2-carbonyl)-amino]-4-methoxy-pyrrolidin-1-yl}-acetic acid ethyl ester (example 25.2) was reacted with 2-amino-6,7-dihydro-thiazolo[5,4]pyridine-5-carboxylic acid tert-butyl ester (CAS 365996-05-0) to give 2-(2-{(3S,4S)-3-[(5-chloro-thiophene-2-carbonyl)-amino]-4-methoxy-pyrrolidin-1-yl}-acetylamino)-6,7-dihydro-thiazolo[5,4-]pyridine-5-carboxylic acid tert-butyl ester as off-white solid. MS 556.3 ([M+H]⁺)

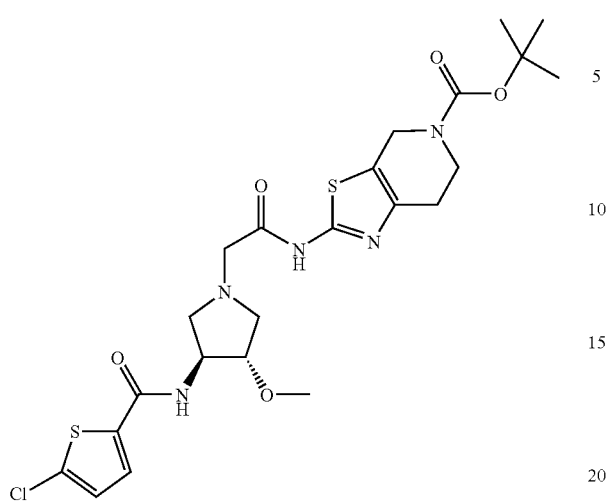

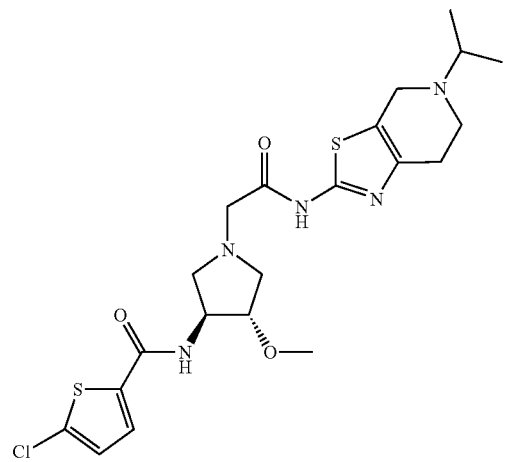

Example 95

94.2 According to general procedure B 2-(2-{(3S,4S)-3-[(5-chloro-thiophene-2-carbonyl)-amino]-4-methoxy-pyrrolidin-1-yl}-acetylamino)-6,7-dihydro-thiazolo[5,4-]pyridine-5-carboxylic acid tert-butyl ester was converted to 5-chloro-thiophene-2-carboxylic acid {(3S,4S)-4-methoxy-1-[(4,5,6,7-tetrahydro-thiazolo[5,4]pyridin-2-ylcarbamoyl)-methyl]-pyrrolidin-3-yl}-amide dihydrochloride. Off-white solid. MS 456.4 ([M+H]$^+$)

In analogy to example 94.3 5-chloro-thiophene-2-carboxylic acid {(3S,4S)-4-methoxy-1-[(4,5,6,7-tetrahydro-thiazolo[5,4]pyridin-2-ylcarbamoyl)-methyl]-pyrrolidin-3-yl}-amide dihydrochloride (example 94.2) was reacted with 1-(bromomethyl)cyclopropane to give 5-chloro-thiophene-2-carboxylic acid {(3S,4S)-1-[(5-cyclopropylmethyl-4,5,6,7-tetrahydro-thiazolo[5,4]pyridin-2-ylcarbamoyl)-methyl]-4-methoxy-pyrrolidin-3-yl}-amide. Yellow solid. MS 510.5 ([M+H]$^+$)

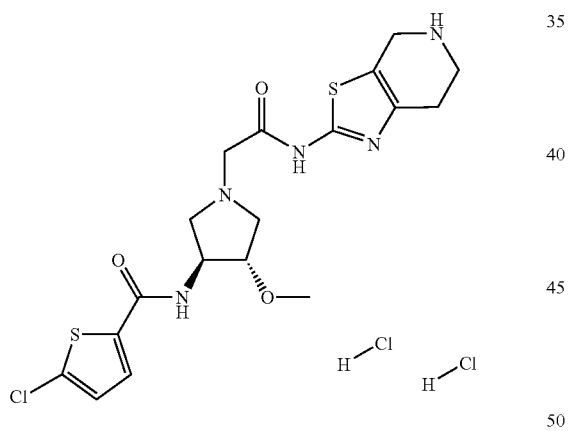

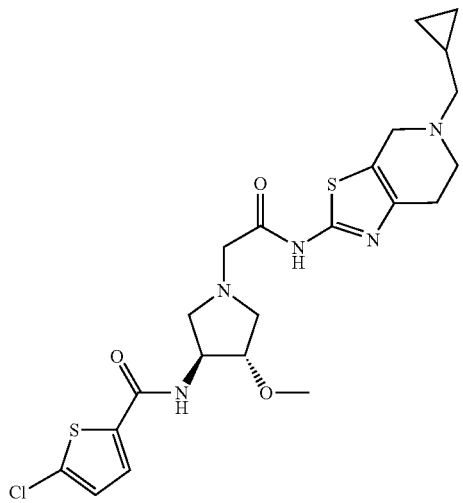

94.3 A suspension of 60 mg 5-chloro-thiophene-2-carboxylic acid {(3S,4S)-4-methoxy-1-[(4,5,6,7-tetrahydro-thiazolo[5,4]pyridin-2-ylcarbamoyl)-methyl]-pyrrolidin-3-yl}-amide dihydrochloride in 3 ml THF was treated with 0.03 ml TEA and 0.01 ml 2-iodopropane. After stirring at r.t. overnight, the reaction mixture was again treated with 0.03 ml TEA and 0.03 ml 2-iodopropane and heated to 70° C. overnight. Then, it was concentrated. The crude product was purified by column chromatography (silica gel; gradient: CH$_2$Cl$_2$->CH$_2$Cl$_2$/MeOH 9:1) to give 51 mg 5-chloro-thiophene-2-carboxylic acid {(3S,4S)-1-[(5-isopropyl-4,5,6,7-tetrahydro-thiazolo[5,4]pyridin-2-ylcarbamoyl)-methyl]-4-methoxy-pyrrolidin-3-yl}-amide as yellow solid. MS 498.4 ([M+H]$^+$)

Example 96

96.1 A suspension of 210 mg NaH (55% in mineral oil) in 3 ml DMF was treated at 0° C. with 1.0 g (3S,4S)-3-azido-4-hydroxy-pyrrolidine-1-carboxylic acid tert-butyl ester in 6 ml DMF. The reaction mixture was stirred at 0° C. for 90 min, then it was cooled to 0° C. A solution of 0.53 ml ethyl bromoacetate was added dropwise. The reaction mixture was slowly warmed to r.t., stirred overnight, then heated for 1 hr at 50° C. After cooling to r.t. the mixture was taken up in EtOAc and washed with H$_2$O. The combined organics were dried over MgSO$_4$, filtrated and concentrated. The crude product was purified by column chromatography (silica gel; cyclohexane->cyclohexane/EtOAc 3:2) to give 584 mg (3S,4S)-3-azido-4-ethoxycarbonylmethoxy-pyrrolidine-1-carboxylic acid tert-butyl ester as yellow liquid. MS 315.2 ([M+H]$^+$)

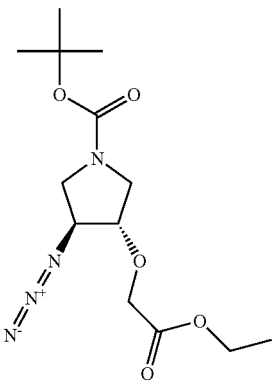

96.2 In analogy to examples 22.3-22.6 (3S,4S)-3-azido-4-ethoxycarbonylmethoxy-pyrrolidine-1-carboxylic acid tert-butyl ester was converted to ((3S,4S)-4-[(5-chloro-thiophene-2-carbonyl)-amino]-1-{[2-fluoro-4-(2-oxo-pyridin-1-yl)-phenylcarbamoyl]-methyl}-pyrrolidin-3-yloxy)-acetic acid ethyl ester. White amorphous solid. MS 577.5 ([M+H]$^+$)

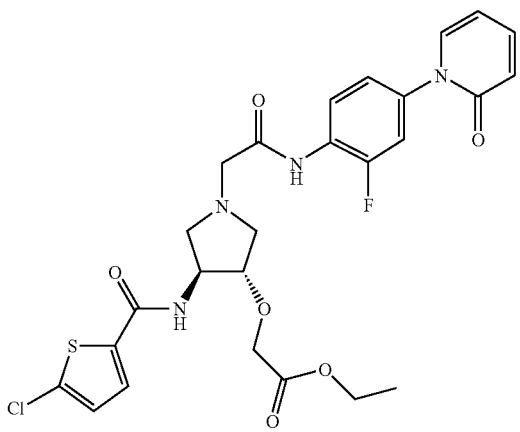

Example 97

A solution of 359 mg ((3S,4S)-4-[(5-chloro-thiophene-2-carbonyl)-amino]-1-{[2-fluoro-4-(2-oxo-pyridin-1-yl)-phenylcarbamoyl]-methyl}-pyrrolidin-3-yloxy)-acetic acid ethyl ester (example 96.2) in 10 ml THF was treated with 1.24 ml 1N NaOH and stirred for 5 hrs at r.t. The reaction mixture was concentrated. The crude product was purified by chromatography (silica gel; gradient: CH$_2$Cl$_2$->CH$_2$Cl$_2$/MeOH 7:3) to give 279 mg ((3S,4S)-4-[(5-chloro-thiophene-2-carbonyl)-amino]-1-{[2-fluoro-4-(2-oxo-pyridin-1-yl)-phenylcarbamoyl]-methyl}-pyrrolidin-3-yloxy)-acetic acid as white solid. MS 549.3 ([M+H]$^+$)

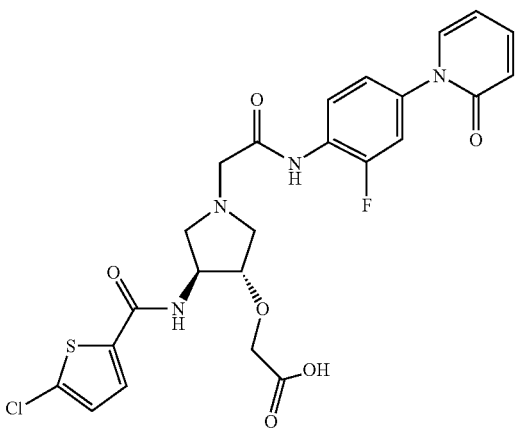

Example 98

A solution of 50 mg ((3S,4S)-4-[(5-chloro-thiophene-2-carbonyl)-amino]-1-{[2-fluoro-4-(2-oxo-pyridin-1-yl)-phenylcarbamoyl]-methyl}-pyrrolidin-3-yloxy)-acetic acid (example 97) in 1 ml DMF was treated with 264 mg ammonium chloride, 21 mg EDCI, 3 mg DMAP and 0.04 ml TEA. The reaction mixture was stirred over night at r.t., then concentrated. The crude product was isolated by column chromatography (silica gel; gradient: CH$_2$Cl$_2$->CH$_2$Cl$_2$/MeOH 4:1) to give 23 mg 5-chloro-thiophene-2-carboxylic acid ((3S,4S)-4-carbamoylmethoxy-1-{[2-fluoro-4-(2-oxo-pyridin-1-yl)-phenylcarba-moyl]-methyl}-pyrrolidin-3-yl)-amide as white solid. MS 548.0 ([M+H]$^+$)

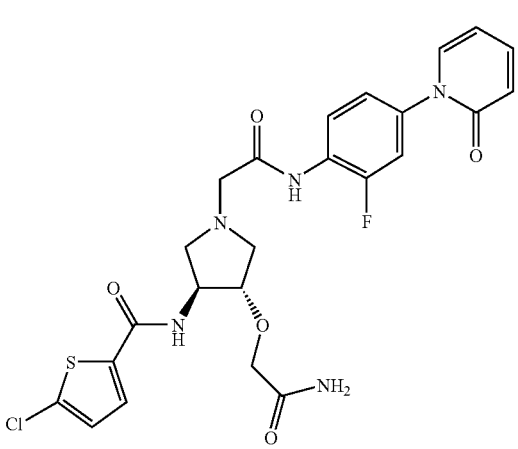

Example 99

According to general procedure D ((3S,4S)-4-[(5-chloro-thiophene-2-carbonyl)-amino]-1-{[2-fluoro-4-(2-oxo-pyridin-1-yl)-phenylcarbamoyl]-methyl}-pyrrolidin-3-yloxy)-acetic acid (example 97) was reacted with cyclopropylamine to give 5-chloro-thiophene-2-carboxylic acid ((3S,4S)-4-cyclopropylcarbamoylmethoxy-1-{[2-fluoro-4-(2-oxo-pyridin-1-yl)-phenylcarbamoyl]-methyl}-pyrrolidin-3-yl)-amide. White solid. MS588.5 ([M+H]$^+$)

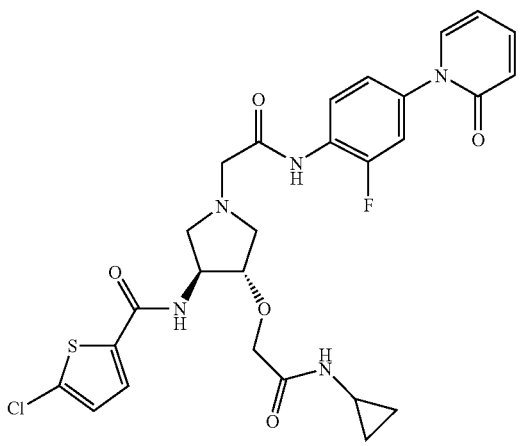

Example 100

According to general procedure D ((3S,4S)-4-[(5-chloro-thiophene-2-carbonyl)-amino]-1-{[2-fluoro-4-(2-oxo-pyridin-1-yl)-phenylcarbamoyl]-methyl}-pyrrolidin-3-yloxy)-acetic acid (example 97) was reacted with dimethylamine hydrochloride to give 5-chloro-thiophene-2-carboxylic acid ((3S,4S)-4-dimethylcarbamoylmethoxy-1-{[2-fluoro-4-(2-oxo-pyridin-1-yl)-phenylcarbamoyl]-methyl}-pyrrolidin-3-yl)-amide. Off-white solid. MS576.3 ([M+H]$^+$)

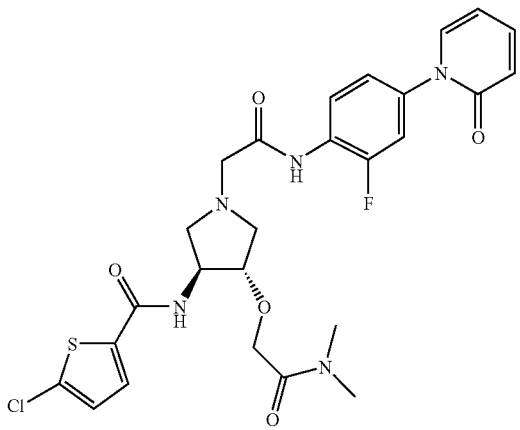

Example 101

101.1 To a stirred, cooled (0° C.) solution of 3.18 g N-benzyl-N-(methoxymethyl)trimethyl-silylmethylamine (CAS 93102-05-7) in 30 ml CH$_2$Cl$_2$ under an argon atmosphere was added dropwise a solution of 1.69 g (E)-3-cyclopropyl-acrylic acid methyl ester (CAS 59939-11-6; J. Org. Chem. 1990, 55(10), 3097) in 15 ml CH$_2$Cl$_2$ over a period of 20 min. Then a solution of 0.1 ml TFA in 5 ml CH$_2$Cl$_2$ was added dropwise within 10 min. When addition was complete, the mixture (slowly warming up to room temperature) was stirred overnight. Then, the mixture was diluted with CH$_2$Cl$_2$, washed with sat. aq. NaHCO$_3$ and brine, dried over MgSO$_4$, filtered and concentrated. The crude product was isolated by chromatography (silica gel; (gradient: cyclohexane->cyclohexane/EtOAc 7:3) to give 1.14 g (3RS,4RS)-1-benzyl-4-cyclopropyl-pyrrolidine-3-carboxylic acid methyl ester as light yellow oil. MS 260.3 ([M+H]$^+$)

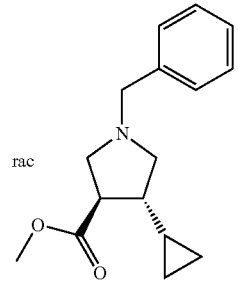

101.2 To a stirred solution of 1.13 g (3RS,4RS)-1-benzyl-4-cyclopropyl-pyrrolidine-3-carboxylic acid methyl ester at r.t. in 10 ml methanol under an argon atmosphere was added 113 mg 10% Pd/C. The mixture was then stirred at r.t. under a hydrogen atmosphere overnight. The catalyst was filtered off and rinsed with methanol. The filtrate was concentrated to leave 630 mg (3RS,4RS)-4-cyclopropyl-pyrrolidine-3-carboxylic acid methyl ester as a light yellow oil. MS170.3 ([M+H]$^+$)

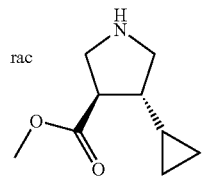

101.3 To a stirred, cooled (0° C.) solution of 625 mg (3RS,4RS)-4-cyclopropyl-pyrrolidine-3-carboxylic acid methyl ester in 6 ml dichloromethane under an argon atmosphere were added 0.51 ml triethylamine and 0.30 ml pyridine. To this was added a solution of 806 mg Boc$_2$O in 4 ml CH$_2$Cl$_2$ over a period of 10 min. The ice bath was removed and stirring at r.t. was continued overnight. The mixture was diluted with CH$_2$Cl$_2$, washed with 0.5 N HCl, H2O and brine, dried over MgSO$_4$, filtered and concentrated. The crude product was purified by column chromatography (silica gel; cyclohexane-> cyclohexane/EtOAc 3:1) to give 635 mg (3RS,4RS)-4-cyclopropyl-pyrrolidine-1,3-dicarboxylic acid 1-tert-butyl ester 3-methyl ester as colorless viscous oil. MS 292.1 ([M+H]$^+$)

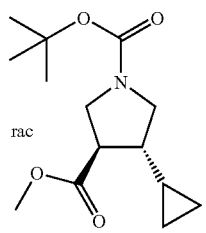

101.4 To a stirred solution of 630 mg (3RS,4RS)-4-cyclopropyl-pyrrolidine-1,3-dicarboxylic acid 1-tert-butyl ester 3-methyl ester at r.t. in 5 ml ethanol under an argon atmosphere was added 4.7 ml 1 N NaOH. The mixture was then stirred for 4 h, then concentrated, dissolved in 5 ml H₂O, acidified to pH 1 by the addition of 1 N HCl, and extracted with EtOAc. The combined organics were washed with H₂O and brine, dried over MgSO₄, filtered and concentrated to leave the crude product as a colorless gum which turned to an off-white solid after standing one night at room temperature: 497 mg (3RS,4RS)-4-cyclopropyl-pyrrolidine-1,3-dicarboxylic acid 1-tert-butyl ester. MS 254.1 ([M−H]⁻)

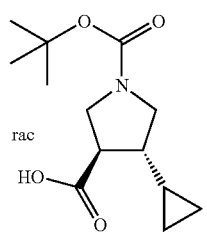

101.5 To a stirred solution of 200 mg (3RS,4RS)-4-cyclopropyl-pyrrolidine-1,3-dicarboxylic acid 1-tert-butyl ester at 80° C. in 2 ml dioxane under an argon atmosphere were added 0.20 ml diphenylphosphoryl azide and 0.16 ml N-ethyldiisopropylamine. Stirring at 80° C. was continued for 4 hrs. Then, the hot mixture was poured onto 15 ml 1 N KOH and the product was extracted with EtOAc. The aqueous phase was back extracted with EtOAc. The combined organics were washed with H₂O and brine, dried over MgSO₄, filtered and concentrated. The crude product was purified by column chromatography (silica gel; gradient: CH₂Cl₂->CH₂Cl₂/MeOH 9:1) to give 34 mg (3RS,4SR)-3-amino-4-cyclopropyl-pyrrolidine-1-carboxylic acid tert-butyl ester as light brown gum. MS 227.3 ([M+H]⁺)

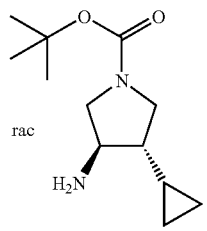

101.6 In analogy to example 11 (3RS,4SR)-3-amino-4-cyclopropyl-pyrrolidine-1-carboxylic acid tert-butyl ester was converted to 5-chloro-thiophene-2-carboxylic acid ((3RS,4SR)-4-cyclopropyl-1-{[2-fluoro-4-(2-oxo-2H-pyridin-1-yl)-phenylcarbamoyl]-methyl}-pyrrolidin-3-yl)-amide. Off-white amorphous solid. MS 515.3 ([M+H]⁺)

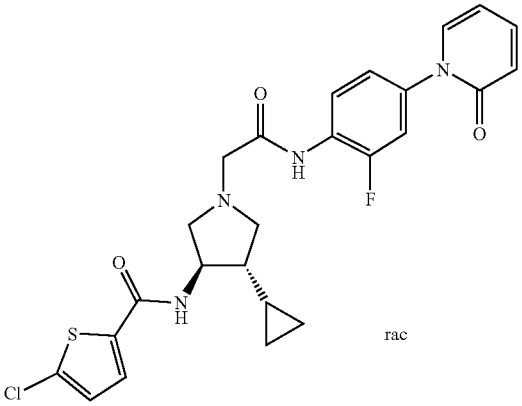

Example 102

102.1 In analogy to example 101.1 ethyl crotonate and N-benzyl-N-(methoxymethyl)tri-methylsilylmethylamine (CAS 93102-05-7) were reacted to give (3RS,4RS)-1-benzyl-4-methyl-pyrrolidine-3-carboxylic acid ethyl ester. Light yellow solid. MS 248.3 ([M+H]⁺)

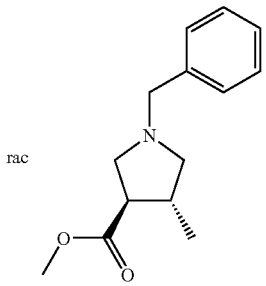

102.2 In analogy to examples 101.2-101.6 (3RS,4RS)-1-benzyl-4-methyl-pyrrolidine-3-carboxylic acid ethyl ester was converted to 5-chloro-thiophene-2-carboxylic acid ((3RS,4SR)-1-{[2-fluoro-4-(2-oxo-pyridin-1-yl)-phenylcarbamoyl]-methyl}-4-methyl-pyrrolidin-3-yl)-amide. White solid. MS 489.4 ([M+H]⁺)

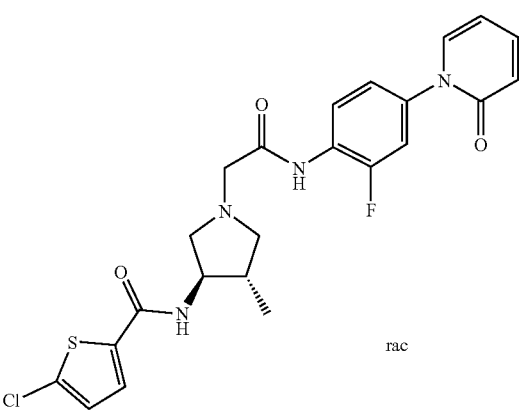

Example 103

103.1 In analogy to example 101.1 ethyl cinnamate and N-benzyl-N-(methoxymethyl)tri-methylsilylmethylamine (CAS 93102-05-7) were reacted to give (3RS,4SR)-1-benzyl-4-phenyl-pyrrolidine-3-carboxylic acid ethyl ester. Light yellow liquid. MS 310.1 ([M+H]⁺)

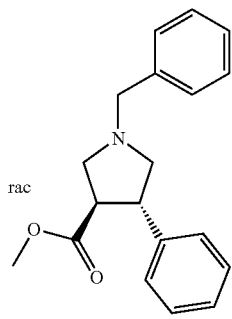

103.2 In analogy to examples 101.2-101.6 (3RS,4SR)-1-benzyl-4-phenyl-pyrrolidine-3-carboxylic acid ethyl ester was converted to 5-chloro-thiophene-2-carboxylic acid ((3RS,4SR)-1-{[2-fluoro-4-(2-oxo-pyridin-1-yl)-phenylcarbamoyl]-methyl}-4-phenyl-pyrrolidin-3-yl)-amide. White solid. MS 551.2 ([M+H]⁺)

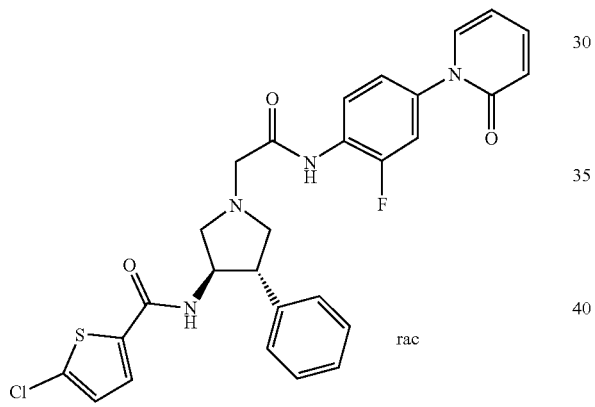

Example 104

104.1 In analogy to example 101.1 (E)-4-methyl-pent-2-enoic acid ethyl ester and N-benzyl-N-(methoxymethyl)tri-methylsilylmethylamine (CAS 93102-05-7) were reacted to give (3RS,4RS)-1-benzyl-4-isopropyl-pyrrolidine-3-carboxylic acid ethyl ester. Light yellow oil.

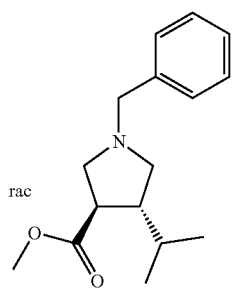

104.2 In analogy to examples 101.2-101.6 3RS,4RS)-1-benzyl-4-isopropyl-pyrrolidine-3-carboxylic acid ethyl ester was converted to 5-chloro-thiophene-2-carboxylic acid ((3RS,4SR)-1-{[2-fluoro-4-(2-oxo-pyridin-1-yl)-phenylcarbamoyl]-methyl}-4-isopropyl-pyrrolidin-3-yl)-amide. Off-white amorphous solid. MS 515.3 ([M+H]⁺)

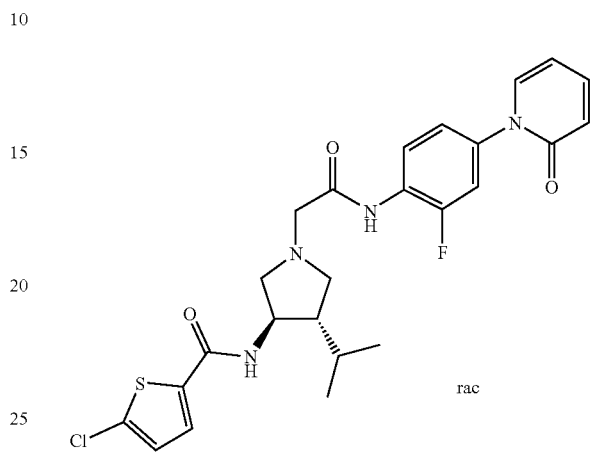

Example 105

105.1 In analogy to example 101.1 ((E)-5-(tert-butyl-dimethyl-silanyloxy)-pent-2-enoic acid methyl ester (CAS 688801-64-1) and N-benzyl-N-(methoxymethyl)tri-methylsilylmethylamine (CAS 93102-05-7) were reacted to give (3RS,4RS)-1-benzyl-4-[2-(tert-butyl-dimethyl-silanyloxy)-ethyl]-pyrrolidine-3-carboxylic acid methyl ester. Light yellow oil. MS 378.3 ([M+H]⁺)

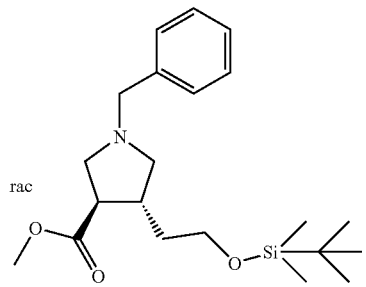

105.2 In analogy to examples 101.2-101.6 (3RS,4RS)-1-benzyl-4-[2-(tert-butyl-dimethyl-silanyloxy)-ethyl]-pyrrolidine-3-carboxylic acid methyl ester was converted to 5-chloro-thiophene-2-carboxylic acid [(3RS,4SR)-1-{[2-fluoro-4-(2-oxo-2H-pyridin-1-yl)-phenyl-carbamoyl]-methyl}-4-(2-hydroxy-ethyl)-pyrrolidin-3-yl]-amide. Off-white amorphous solid. MS 519.3 ([M+H]⁺)

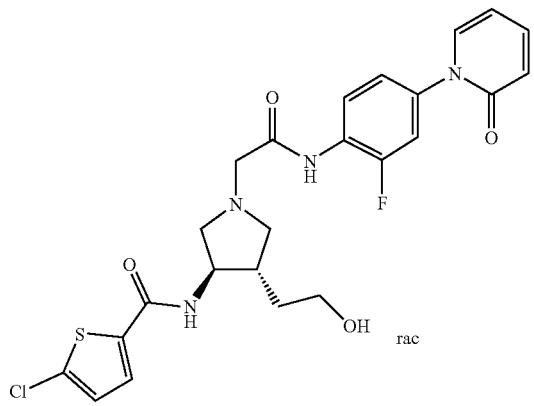

Example 106 (Reference)

106.1 3-(tert-Butoxycarbonylamino)pyrrolidine (2.5 g) was dissolved in acetonitrile (20 ml). DIEA (2.28 ml) was added followed by the addition of ethyl oxalylchlorid (1.49 g). The reaction mixture was stirred at 25° C. for 3 h. The reaction mixture was afterwards diluted with ethyl acetate (50 ml) extracted with aq. $Na_2CO_3$ solution (10%, 20 ml) and aq. HCl solution (1N, 20 ml). The organic phase was dried over $Na_2SO_4$, filtered and evaporated to dryness to yield (3-tert-butoxycarbonylamino-pyrrolidin-1-yl)-oxo-acetic acid ethyl ester (3.63 g) as dark red oil. MS 287.3 ([M+H]$^+$).

106.2 (3-tert-Butoxycarbonylamino-pyrrolidin-1-yl)-oxo-acetic acid ethyl ester (1.5 g) was dissolved in $CH_2Cl_2$ (7 ml) and TFA (7 ml) was added. The mixture was stirred at 25° C. for 3 h, evaporated to dryness to yield crude (3-amino-pyrrolidin-1-yl)-oxo-acetic acid ethyl ester trifluoroacetate as red brown oil (1.57 g). MS 187.3 ([M+H]$^+$)

106.3 5-Chloro-thiophene-2-carboxylic acid (0.94 g) was dissolved in THF (10 ml) and CDI (0.94 g) was added. This mixture was stirred at 25° C. for 30 min. A solution of (3-amino-pyrrolidin-1-yl)-oxo-acetic acid ethyl ester trifluoroacetate (1.57 g), dissolved in THF (10 ml) and DIEA (0.89 ml), is added to the reaction mixture. The obtained reaction mixture was stirred for 18 h at 25° C. Finally, the reaction mixture was evaporated to dryness. The crude product was purified by chromatography (silica gel; gradient: $CH_2Cl_2$ to $CH_2Cl_2$/MeOH 98:2) to give {3-[(5-chloro-thiophene-2-carbonyl)-amino]-pyrrolidin-1-yl}-oxo-acetic acid ethyl ester (1.9 g) as an orange oil. MS 331.3 ([M+H]$^+$, Cl-isotopes).

106.4 1-(4-Amino-3-fluoro-phenyl)-1H-pyridin-2-one (74 mg) was dissolved in toluene (5 ml) and treated with a solution of $AlMe_3$ in toluene (2M, 0.18 ml). The mixture was stirred for 2 h at 25° C. After that, a solution of {3-[(5-chloro-thiophene-2-carbonyl)-amino]-pyrrolidin-1-yl}-oxo-acetic acid ethyl ester in toluene (2 ml) was added to the reaction mixture. The whole mixture was stirred at 110° C. for 18 h and then cooled to 25° C. The mixture was then treated with acetic acid (0.07 ml) and filtrated. The filtrate was purified by preparative HPLC to yield 5-chloro-thiophene-2-carboxylic acid {1-[2-fluoro-4-(2-oxo-2H-pyridin-1-yl)-phenylaminooxalyl]-pyrrolidin-3-yl}-amide (20 mg) as yellow oil. MS 489.3 ([M+H]$^+$, Cl-isotopes).

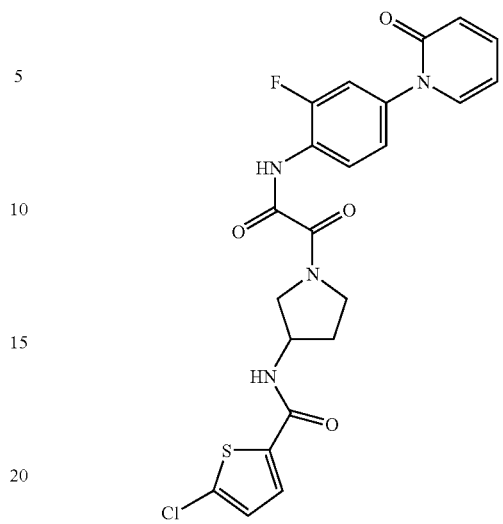

Example 107

107.1 Under an Ar atmosphere 1-benzyl-4-trifluoromethyl-pyrrolidine-3-carboxylic acid ethyl ester (10 g) (CAS152188-51-7P, synthesis described at Jean Pierre Begue et al. Tetrahedron Lett., 1993, 34(20), 3279-82) is dissolved in ethanol (100 ml). Acetic acid (0.19 ml), di-tert. butyl dicarbonate (7.6 g) and Pd/C (10%, 106 mg) were added to the solution. The argon atmosphere was changed to a hydrogen atmosphere. The mixture was stirred for 1 h at 25° C. and the hydrogen atmosphere was then refreshed. The mixture was afterwards stirred additional 7 h at 25° C., filtered then through a sartorius funnel and the filtrate was evaporated to dryness. The crude product as dissolved in THF (100 ml) and water (10 ml). DMAP (20 mg) was added to the solution and the mixture was stirred for 2 h at 25° C. After that the mixture was diluted with $CH_2Cl_2$ (100 ml) and extracted with water. The organic layer was dried over $Na_2SO_4$, filtered and evaporated to dryness to yield (3RS,4SR)-4-trifluoromethyl-pyrrolidine-1,3-dicarboxylic acid 1-tert-butyl ester 3-ethyl ester (9.76 g) as colorless oil. MS 312.3 ([M+H]$^+$).

107.2 (3RS,4SR)-4-Trifluoromethyl-pyrrolidine-1,3-dicarboxylic acid 1-tert-butyl ester 3-ethyl ester (9.76 g) was dissolved in THF/water (1:1 10 ml) and LiOH (0.826 g) was added to the emulsion. The mixture was stirred for 18 h at 25° C. The reaction mixture was then diluted with $CH_2Cl_2$ (50 ml) and treated with HCl (1N, 20 ml). The aqueous phase was extracted twice with $CH_2Cl_2$ (20 ml) and the combined organic layers were dried over $Na_2SO_4$, filtered and evaporated to dryness to yield (3RS,4SR)-4-trifluoromethyl-pyrrolidine-1,3-dicarboxylic acid 1-tert-butyl ester (5.8 g) as light yellow solid. MS 284.3 ([M+H]$^+$).

107.3 (3RS,4SR)-3-Trifluoromethyl-4-(2-trimethylsilanyl-ethoxycarbonylamino)-pyrro-lidine-1-carboxylic acid tert-butyl ester was prepared according to the methods described for example 40.1 to yield 3.1 g as a yellow oil. MS 399.5 ([M+H]$^+$).

107.4 (3S,4R)-3-[(5-Chloro-thiophene-2-carbonyl)-amino]-4-trifluoromethyl-pyrrolidine-1-carboxylic acid tert-butyl ester was prepared according to the methods described for example 40.2 to yield 1.3 g as a yellow foam. MS 399.3 ([M+H]$^+$, Cl-isotopes).

107.5 5-Chloro-thiophene-2-carboxylic acid ((3SR,4RS)-4-trifluoromethyl-pyrrolidin-3-yl)-amide; hydrochloride was prepared according to the methods described for example 40.3 to yield 0.98 g as a yellow foam. MS 299.3 ([M+H]+, Cl-isotopes).

107.6 5-Chloro-thiophene-2-carboxylic acid ((3SR,4RS)-1-{[2-fluoro-4-(2-oxo-2H-pyridin-1-yl)-phenylcarbamoyl]-methyl}-4-trifluoromethyl-pyrrolidin-3-yl)-amide was prepared according to the methods described for example 40.4 to yield 60 mg as a white solid. MS 543.2 ([M+H]), Cl-isotopes).

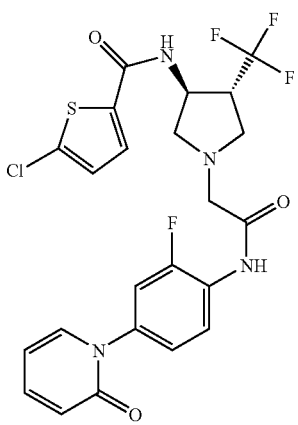

Example 108

5-Chloro-thiophene-2-carboxylic acid ((3RS,4RS)-1-{[4-(3-oxo-morpholin-4-yl)-phenylcarbamoyl]-methyl}-4-trifluoromethyl-pyrrolidin-3-yl)-amide was prepared starting from example 107.5 according to the methods described for examples 39.1 and 39.4 to yield 54 mg as a light yellow solid. MS 531.2 ([M+H]), Cl-isotopes).

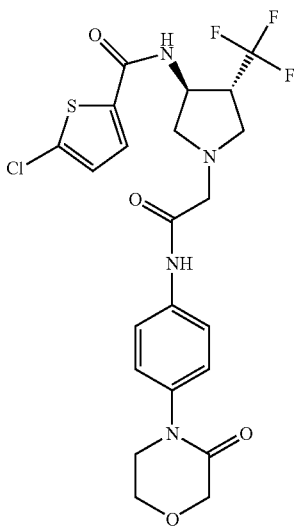

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed is:
1. A compound of formula (I):

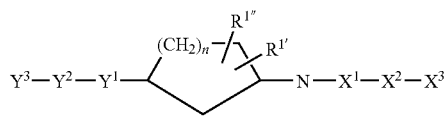

or a pharmaceutically acceptable salt thereof wherein:
$X^1$ is selected from the group consisting of —CHR$^2$—C(O)—NH— and —C(O)—NH—;
$X^2$ is phenylene optionally substituted by one or more substituents independently selected from the group consisting of: (1) $C_{1-6}$ alkyl, (2) $C_{3-7}$ cycloalkyl, (3) $C_{3-7}$ cycloalkyl-$C_{1-6}$ alkylene, (4) $C_{1-6}$ alkoxy, (5) halogen, (6) cyano, (7) nitro, (8) amino, (9) —CO—NH—$C_{1-6}$ alkyl, and (10) —CO—N($C_{1-6}$ alky)$_2$;
$X^3$ is pyridinyl or 2-oxo-2H-pyridin-1-yl wherein said pyridinyl or 2-oxo-2H-pyridin-1-yl is optionally substituted by one or more substituents independently selected from the group consisting of $C_{1-6}$ alkyl, $C_{1-6}$ alkoxy, halogen, cyano, nitro, amino, mono-$C_{1-6}$ alkyl substituted amino, di-$C_{1-6}$ alkyl substituted amino, mono-$C_{1-6}$ alkyl substituted amino-$C_{1-6}$ alkylene, di-$C_{1-6}$ alkyl substituted amino-$C_{1-6}$ alkylene, —SO$_2$-$C_{1-6}$ alkyl, —SO$_2$—NH$_2$, —SO$_2$—NH—$C_{1-6}$ alkyl and —SO$_2$—N($C_{1-6}$ alkyl)$_2$,
$R^2$ is selected from the group consisting of hydrogen and $C_{1-6}$ alkyl;
$Y^1$ is —NH—C(O)—;
$Y^2$ is thiophene optionally substituted by one or more substituents independently selected from the group consisting of: (1) $C_{1-6}$ alkyl, (2) $C_{3-7}$ cycloalkyl, (3) $C_{3-7}$ cycloalkyl-$C_{1-6}$ alkylene, (4) $C_{1-6}$ alkoxy, (5) halogen, (6) cyano, (7) nitro, (8) amino, (9) —CO—NH—$C_{1-6}$ alkyl, and (10) —CO—N($C_{1-6}$ alky)$_2$;
$Y^3$ is selected from the group consisting of hydrogen and phenyl, wherein said phenyl is optionally substituted by one or more substituents independently selected from the group consisting of $C_{1-6}$ alkyl, $C_{1-6}$ alkoxy, halogen, cyano, nitro, amino, mono-$C_{1-6}$ alkyl substituted amino, di-$C_{1-6}$ alkyl substituted amino, mono-$C_{1-6}$ alkyl substituted amino-$C_{1-6}$ alkylene, di-$C_{1-6}$ alkyl substituted amino-$C_{1-6}$ alkylene, —SO$_2$—$C_{1-6}$ alkyl, —SO$_2$—NH$_2$, —SO$_2$—NH—$C_{1-6}$ alkyl and —SO$_2$—N($C_{1-6}$ alkyl)$_2$, wherein one or two carbon atoms of said phenyl is optionally replaced with a carbonyl group;
$R^{1''}$ is selected from the group consisting of halogen, carboxyl, $C_{1-6}$ alkoxycarbonyl, hydroxy $C_{1-6}$ alkyl-NH—C(O)—, N($C_{1-6}$ alkyl)(hydroxy $C_{1-6}$ alkyl)—C(O)—, $C_{1-6}$ alkyl-NH—C(O)—, halo $C_{1-6}$ alkyl-NH—C(O)—, $C_{3-7}$ cycloalkyl-$C_{1-6}$ alkylene-NH—C(O)—, hydroxy $C_{1-6}$ alkyl, hydroxy, $C_{1-6}$ alkoxy, $C_{1-6}$ alkoxy-$C_{1-6}$ alkylene, halo $C_{1-6}$ alkoxy-$C_{1-6}$ alkylene, halo $C_{1-6}$ alkyl, halo $C_{1-6}$ alkoxy, $C_{1-6}$ alkyl-sulfonylamino-$C_{1-6}$ alkylene, ($C_{1-6}$ alkyl-sulfonyl) ($C_{1-6}$ alkyl)amino-$C_{1-6}$ alkylene, $C_{1-6}$ alkyl-carbonylamino-$C_{1-6}$ alkylene, hydroxy $C_{1-6}$ alkoxy-, amino, di-$C_{1-6}$ alkyl substituted amino, mono-$C_{1-6}$ alkyl substituted amino, di-$C_{1-6}$ alkyl substituted amino-$C_{1-6}$ alkylene, mono-$C_{1-6}$ alkyl substituted amino-$C_{1-6}$ alkylene, di-halo$C_{1-6}$ alkyl substituted amino, mono-halo$C_{1-6}$ alkyl substituted amino, $C_{3-7}$ cycloalkylamino-$C_{1-6}$ alkylene, ($C_{3-7}$ cycloalkyl)($C_{1-6}$ alkyl)amino-$C_{1-6}$ alkylene, $C_{1-6}$ alkylcarbonyl-$C_{1-6}$ alkylene, $C_{1-6}$ alkyl- sulfonylamino-, $C_{1-6}$ alkyl- carbonylamino-, ($C_{1-6}$ alkylcarbonyl)($C_{1-6}$ alkyl)amino-, ($C_{1-6}$ alkoxy-carbonyl) ($C_{1-6}$ alkyl)amino-, ($C_{1-6}$ alkyl-sulfonyl)($C_{1-6}$ alkyl)amino-, $C_{1-6}$ alkylsulfonyloxy-$C_{1-6}$ alkylene, and ($C_{1-6}$ alkylcarbonyl)($C_{1-6}$ alkyl)amino-$C_{1-6}$ alkylene;
or
$R^{1''}$ is selected from the group consisting of di-halo$C_{1-6}$ alkyl substituted amino-$C_{1-6}$ alkylene, mono-halo$C_{1-6}$ alkyl substituted amino-$C_{1-6}$ alkylene, $C_{1-6}$ alkyl, phenyl optionally substituted by one, two or three of the same or different halogen atoms, $C_{3-7}$ cycloalkyl optionally substituted by one, two or three of the same or different halogen atoms and Z-carbonyl-$C_{1-6}$ alkoxy-, in which Z is selected from the group consisting of hydroxy, $C_{1-6}$ alkoxy and NR'R", wherein R' and R" are independently selected from the group consisting of hydrogen, $C_{1-6}$ alkyl optionally substituted by one, two or three of the same or different halogen atoms, $C_{3-7}$ cycloalkyl optionally substituted by one, two or three of the same or different halogen atoms and $C_{3-7}$ cycloalkyl-$C_{1-6}$ alkylene optionally substituted by one, two or three of the same or different halogen atoms, wherein one or two carbon atoms of the phenyl in said phenyl optionally substituted by one, two or three of the same or different halogen atoms and one or two carbon atoms of the $C_{3-7}$ cycloalkyl in said $C_{3-7}$ cycloalkyl optionally substituted by one, two or three of the same or different halogen atoms and $C_{3-7}$ cycloalkyl-$C_{1-6}$ alkylene optionally substituted by one, two or three of the same or different halogen atoms are optionally replaced with a carbonyl group;

$R^{1'''}$ is hydrogen; or $R^{1'}$ and $R^{1'''}$ form, together with the carbon atom to which they are attached, a member selected from the group consisting of —C(=O)—, —C(=CH$_2$)—, and $C_{3-7}$ cycloalky;

$R^2$ is selected from the group consisting of hydrogen and $C_{1-6}$ alkyl; and n is 1.

2. A compound according to claim 1 wherein $X^1$ is selected from the group consisting of —CH$_2$—C(O)—NH— and —C(O)—NH—.

3. A compound according to claim 1 wherein $X^2$ is 1,4-phenylene optionally substituted by one or more substituents independently selected from the group consisting of $C_{1-6}$ alkyl and halogen.

4. A compound according to claim 3 wherein $X^2$ is 1,4-phenylene optionally substituted by one or more of the same or different halogen atoms.

5. A compound according to claim 4, wherein $X^2$ is 2-fluoro-1,4-phenylene.

6. A compound according to claim 1, wherein $X^3$ is pyridinyl.

7. A compound according to claim 1, wherein $X^3$ is 2-oxo-2H-pyridin-1-yl.

8. A compound according to claim 1 wherein $Y^2$ is thiophene optionally substituted by one or more substituents independently selected from the group consisting of halogen, $C_{1-6}$ alkyl and $C_{1-6}$ alkoxy.

9. A compound according to claim 8 wherein $Y^2$ is thiophene optionally substituted by one or more of the same or different halogen atoms.

10. A compound according to claim 1 wherein $Y^3$ is hydrogen.

11. A compound according to claim 10 wherein $Y^3$-$Y^2$- is 5-chloro-thiophen-2-yl.

12. A compound according to claim 1 wherein $R^{1'}$ is selected from the group consisting of hydroxy, $C_{1-6}$ alkoxy, mono-$C_{1-6}$ alkyl substituted amino, ($C_{1-6}$ alkylsulfonyl)($C_{1-6}$ alkyl)amino-, $C_{1-6}$ alkylsulfonyl-amino-, $C_{1-6}$ alkyl-carbonylamino-, ($C_{1-6}$ alkylcarbonyl)($C_{1-6}$ alkyl)amino- and $CF_3$.

13. A compound according to claim 1 selected from the group consisting of:

5-Chloro-thiophene-2-carboxylic acid ((3S ,4S)-1-{[2-fluoro-4-(2-oxo-2H-pyridin-1-yl)-phenylcarbamoyl]-methyl}-4-hydroxy-pyrrolidin-3-yl)-amide, 5-Chloro-thiophene-2-carboxylic acid ((3S ,4S)-1-{[2-fluoro-4-(2-oxo-2H-pyridin-1-yl)-phenylcarbamoyl]-methyl}-4-hydroxy-pyrrolidin-3-yl)-amide, 5-Chloro-thiophene-2-carboxylic acid ((3S ,4S)-4-methoxy-1-{[4-(2-oxo-2-pyridin-1-yl)-phenylcarbamoyl]-methyl}-pyrrolidin-3-yl)-amide, 5-Chloro-thiophene-2-carboxylic acid ((3S ,4S)-4-ethoxy-1-{[2-fluoro-4-(2-oxo-pyridin-1-yl)-phenylcarbamoyl]-methyl}-pyrrolidin-3-yl)-amide, and 5-Chloro-thiophene-2-carboxylic acid [(3S ,4S)-1-{[2-fluoro-4-(2-oxo-2H-pyridin-1-yl)-phenylcarbamoyl]-methyl}-4-(2-hydroxy-ethoxy)-pyrrolidin-3-yl]-amide.

14. A compound according to claim 1 which is 5-Chloro-thiophene-2-carboxylic acid ((3R,4S)-1-{[2-fluoro-4-(2-oxo-pyridin-1-yl)-phenylcarbamoyl]-methyl}-4-methyl-pyrrolidin-3-yl)-amide.

15. A pharmaceutical composition comprising a compound according to claim 1 and a pharmaceutically acceptable excipient.

* * * * *

UNITED STATES PATENT AND TRADEMARK OFFICE
CERTIFICATE OF CORRECTION

PATENT NO. : 7,820,699 B2  Page 1 of 1
APPLICATION NO. : 11/403973
DATED : October 26, 2010
INVENTOR(S) : Zbinden et al.

It is certified that error appears in the above-identified patent and that said Letters Patent is hereby corrected as shown below:

Claim 13, column 138, line 20, delete "methyl}-4-hydroxy" and insert -- methyl}-4-methoxy --

Signed and Sealed this

Twenty-first Day of December, 2010

David J. Kappos
*Director of the United States Patent and Trademark Office*